US007566533B2

(12) United States Patent
Jacobs et al.

(10) Patent No.: US 7,566,533 B2
(45) Date of Patent: Jul. 28, 2009

(54) CLINICALLY INTELLIGENT DIAGNOSTIC DEVICES AND METHODS

(75) Inventors: Alice A. Jacobs, Boston, MA (US); Vineet Gupta, Brookline, MA (US); Boris Nikolic, Charlestown, MA (US)

(73) Assignee: Intelligent Medical Devices, Inc., Cambridge, MA (US)

( * ) Notice: Subject to any disclaimer, the term of this patent is extended or adjusted under 35 U.S.C. 154(b) by 0 days.

(21) Appl. No.: 11/371,332

(22) Filed: Mar. 8, 2006

(65) Prior Publication Data
US 2006/0240453 A1 Oct. 26, 2006

Related U.S. Application Data

(60) Division of application No. 11/102,498, filed on Apr. 8, 2005, which is a continuation of application No. 09/996,056, filed on Nov. 27, 2001, now Pat. No. 6,905,816.

(60) Provisional application No. 60/253,284, filed on Nov. 27, 2000, provisional application No. 60/287,994, filed on May 1, 2001, provisional application No. 60/308,870, filed on Jul. 30, 2001.

(51) Int. Cl.
C12Q 1/70 (2006.01)
C12Q 1/68 (2006.01)
G01N 33/53 (2006.01)

(52) U.S. Cl. .................. 435/5; 435/6; 435/7.1
(58) Field of Classification Search ............... 435/6, 435/7.1; 536/24.3
See application file for complete search history.

(56) References Cited

U.S. PATENT DOCUMENTS

| | | | |
|---|---|---|---|
| 4,216,245 A | 8/1980 | Johnson | 427/2 |
| 4,315,907 A | 2/1982 | Fridlender et al. | 424/1 |
| 4,358,535 A | 11/1982 | Falkow et al. | 435/5 |
| 4,591,570 A | 5/1986 | Chang | 436/518 |
| 4,731,325 A | 3/1988 | Palva et al. | 435/6 |
| 4,829,010 A | 5/1989 | Chang | 422/58 |
| 5,055,397 A | 10/1991 | Michaels et al. | 435/9 |
| 5,093,236 A | 3/1992 | Gonzales-Prevatt et al. | 435/9 |
| 5,100,777 A | 3/1992 | Chang | 435/7.24 |
| 5,281,540 A | 1/1994 | Merkh et al. | 436/530 |
| 5,340,720 A | 8/1994 | Stetler | 435/7.4 |
| 5,384,263 A | 1/1995 | Kauvar | 436/518 |
| 5,445,934 A | 8/1995 | Fodor et al. | 435/6 |
| 5,486,452 A | 1/1996 | Gordon et al. | 435/5 |
| 5,538,856 A | 7/1996 | Levey et al. | 435/7.24 |
| 5,541,057 A | 7/1996 | Bogart et al. | 435/5 |
| 5,567,594 A | 10/1996 | Calenoff | 435/7.32 |
| 5,610,011 A * | 3/1997 | Smith et al. | 435/6 |
| 5,643,723 A | 7/1997 | Persing et al. | 435/6 |
| 5,658,802 A | 8/1997 | Hayes et al. | 436/518 |
| 5,719,063 A | 2/1998 | Block | 436/501 |
| 5,747,274 A | 5/1998 | Jackowski | 435/7.94 |
| 5,789,260 A | 8/1998 | Naparstek | 435/506 |
| 5,789,538 A | 8/1998 | Rabar et al. | 530/324 |
| 5,807,522 A | 9/1998 | Brown et al. | 422/50 |
| 5,830,637 A | 11/1998 | Frank et al. | 435/5 |
| 5,830,645 A * | 11/1998 | Pinkel et al. | 435/6 |
| 5,843,767 A | 12/1998 | Beattie | 435/287.1 |
| 5,858,804 A | 1/1999 | Zanzucchi et al. | 436/536 |
| 5,861,256 A | 1/1999 | Glass et al. | 435/6 |
| 5,874,219 A | 2/1999 | Rava et al. | 435/6 |
| 5,885,783 A | 3/1999 | Yoo et al. | 435/7.1 |
| 5,910,421 A | 6/1999 | Small, Jr. et al. | 435/19 |
| 5,912,340 A | 6/1999 | Kutyavin et al. | 536/24.5 |
| 5,935,780 A | 8/1999 | Naser | 435/6 |
| 5,981,180 A | 11/1999 | Chandler et al. | 435/6 |
| 5,981,734 A | 11/1999 | Mirzabekov et al. | 536/25.3 |
| 6,007,988 A | 12/1999 | Choo et al. | 435/6 |
| 6,013,431 A | 1/2000 | Söderlund et al. | 435/5 |
| 6,013,453 A | 1/2000 | Choo et al. | 435/6 |
| 6,013,460 A | 1/2000 | Levin | 435/7.1 |
| 6,083,763 A | 7/2000 | Balch | 436/518 |
| 6,110,426 A | 8/2000 | Shalon et al. | 422/68.1 |
| 6,117,643 A | 9/2000 | Simpson et al. | 435/7.1 |
| 6,121,004 A | 9/2000 | Pestronk | 435/7.1 |
| 6,140,466 A | 10/2000 | Barbas, III et al. | 530/350 |
| 6,159,473 A | 12/2000 | Watkins et al. | 424/195.1 |

(Continued)

FOREIGN PATENT DOCUMENTS

EP   0 874 242 A1   10/1988

(Continued)

OTHER PUBLICATIONS

Arenkov, (2000) Protein Microchips: Use for Immunoassay and Enzymatic Reactions, Analytic Biochemistry 278:123-131.

(Continued)

*Primary Examiner*—Kenneth R. Horlick
(74) *Attorney, Agent, or Firm*—Foley & Lardner, LLP; Michel Morency; Michael Yamauchi

(57) ABSTRACT

The invention relates to the clinically intelligent design of diagnostic devices (such as microarrays) and methods of making and using such devices in differential diagnoses of specific clinical symptoms or sets of symptoms. In one aspect, the devices include various probes used to perform parallel screening of a number of analytes. The probes are clustered on the devices based on known clinical presentations of symptoms associated with specific diseases and disorders.

24 Claims, 41 Drawing Sheets

U.S. PATENT DOCUMENTS

| | | |
|---|---|---|
| 6,218,122 B1 | 4/2001 | Friend et al. .................... 435/6 |
| 6,225,625 B1 | 5/2001 | Pirrung et al. ............... 250/302 |
| 6,242,180 B1 | 6/2001 | Chee ............................ 435/6 |
| 6,309,821 B1 | 10/2001 | Au-Young et al. ............ 435/6 |

FOREIGN PATENT DOCUMENTS

| | | |
|---|---|---|
| EP | 0 988 893 A1 | 9/1999 |
| WO | 98/29736 | 7/1988 |
| WO | 96/20951 | 7/1996 |
| WO | 96/32475 | 10/1996 |
| WO | 98/53059 | 11/1998 |
| WO | 99/45388 | 9/1999 |
| WO | 99/51621 | 10/1999 |
| WO | 99/51773 | 10/1999 |
| WO | 00/04382 | 1/2000 |
| WO | 00/04389 | 1/2000 |
| WO | 00/04390 | 1/2000 |
| WO | 00/27521 | 5/2000 |
| WO | 00/43552 | 7/2000 |
| WO | 00/50869 | 8/2000 |

OTHER PUBLICATIONS

Cheng et al., (1999) "A multiple Genotyping Assay for Candidate Markers of Cardiovascular Disease Risk" Genome Research, vol. 9:836-949.

Dobrowolski et al., "DNA Microarray Technology for Neonatal Screening", Acta Paediatr. Suppl., vol. 432:61-64 (1999).

Hingorani et al., (1999) Division of Labor—sequential ATP hydrolysis drives assembly of a DNA polymerase sliding clamp around DNA, The EMBO Journal, vol. 18, 18:5131-5144.

Onrust et al., (1995) "Assembly of a Chromosomal Replication . . . ,"Journal of Biol. Chem., 270(22):13348-13357.

Soong et al., Powering an Inorganic Nanodevice with a Biomolecular Motor, Science, vol. 290:1555-1558.

Yershov, (1996) DNA analysis and diagnostics on oligonucleotide microchips, Proc. Natl. Acad. Sci. USA, vol. 93:4913-4918.

Zhang et al., (2000) Strand invasion by mixed base PNAs and a PNA-peptide chimera, Nucleic Acids Research, vol. 28, 17:3332-3338.

"EZ-Rays Slide Kit for DNA Microarrays", Mosaic Technologies, (Brochure printed from Internet) (Jan. 2001).

* cited by examiner

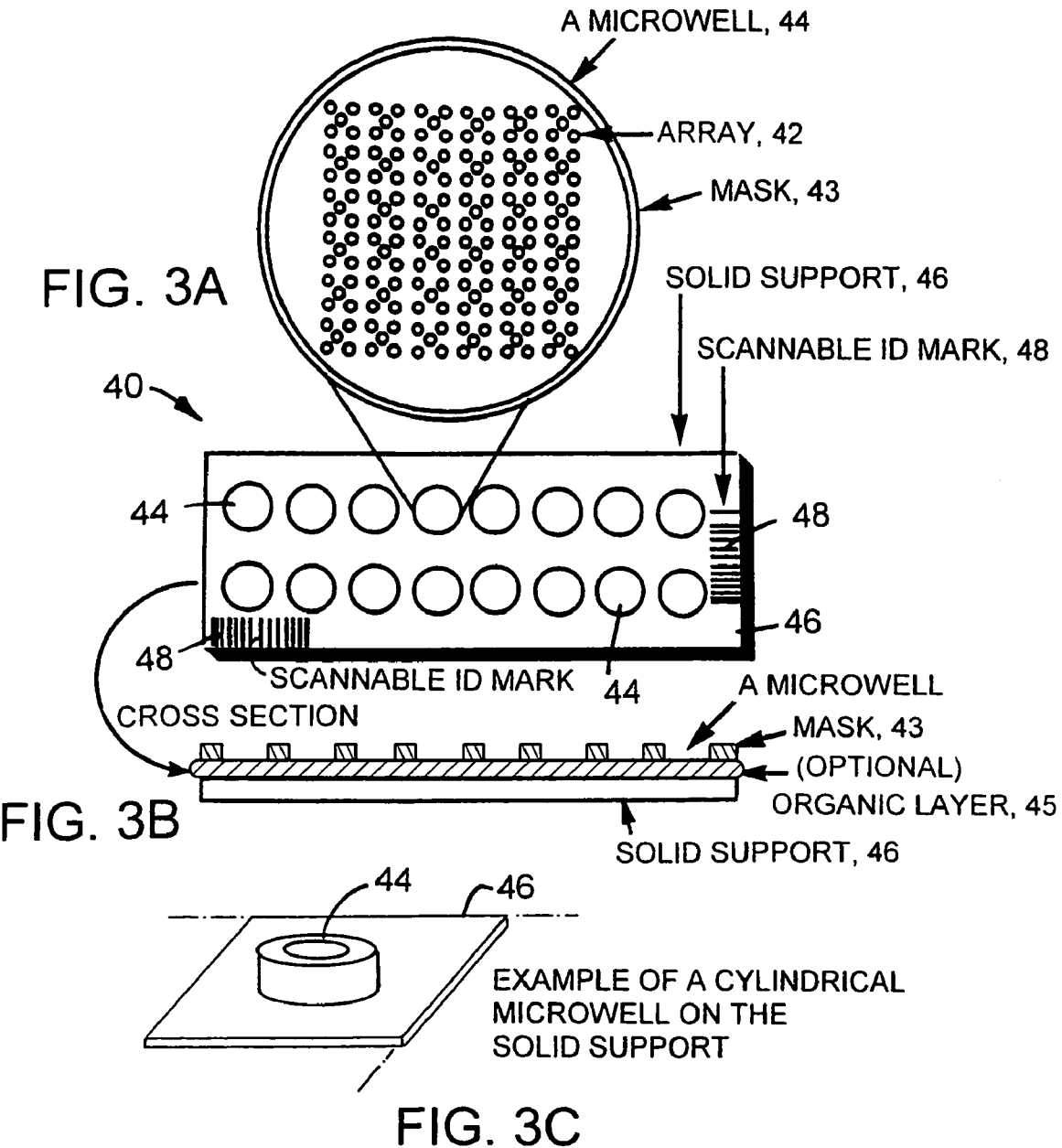

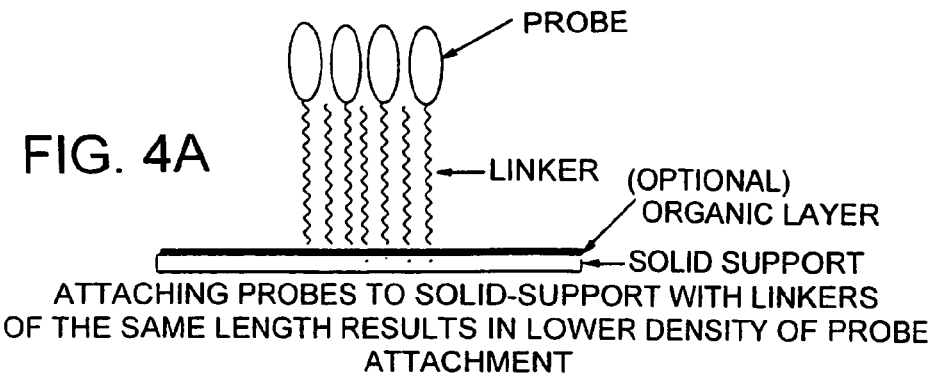

FIG. 4A
ATTACHING PROBES TO SOLID-SUPPORT WITH LINKERS OF THE SAME LENGTH RESULTS IN LOWER DENSITY OF PROBE ATTACHMENT

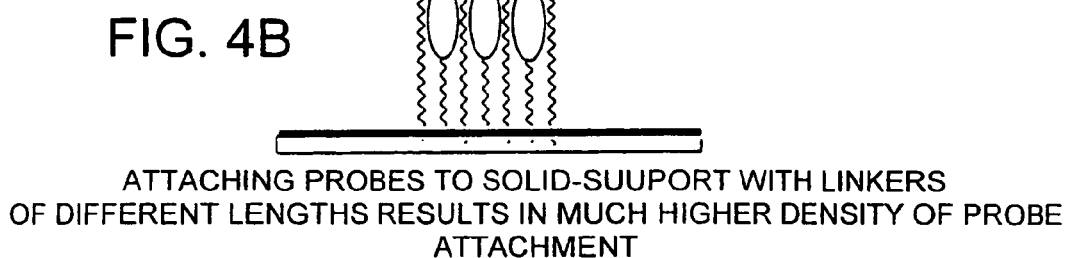

FIG. 4B
ATTACHING PROBES TO SOLID-SUUPORT WITH LINKERS OF DIFFERENT LENGTHS RESULTS IN MUCH HIGHER DENSITY OF PROBE ATTACHMENT

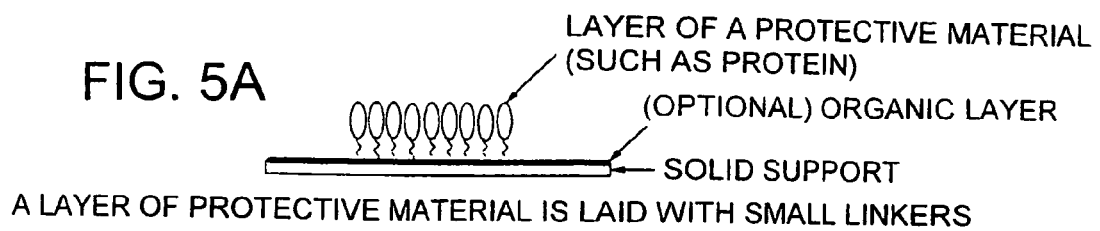

FIG. 5A
A LAYER OF PROTECTIVE MATERIAL IS LAID WITH SMALL LINKERS

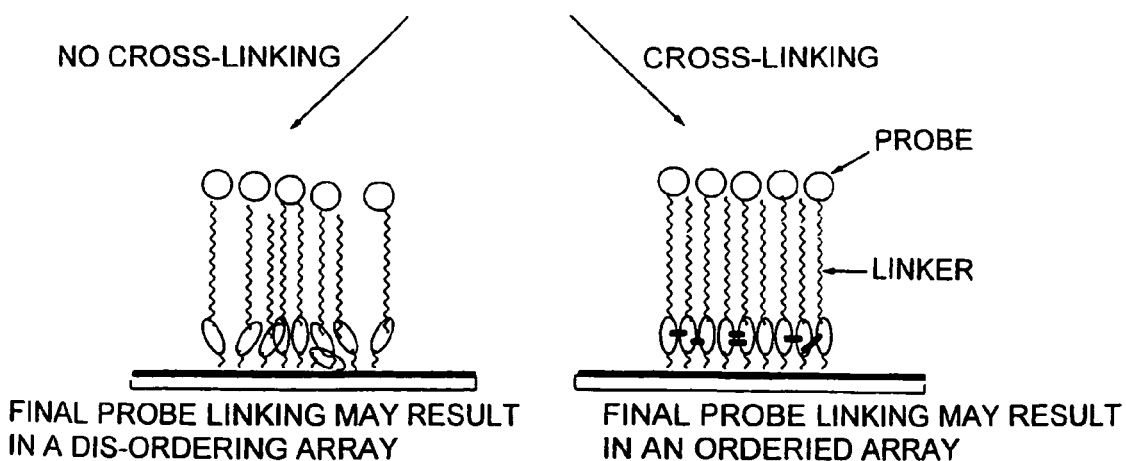

FINAL PROBE LINKING MAY RESULT IN A DIS-ORDERING ARRAY
FIG. 5B

FINAL PROBE LINKING MAY RESULT IN AN ORDERIED ARRAY
FIG. 5C

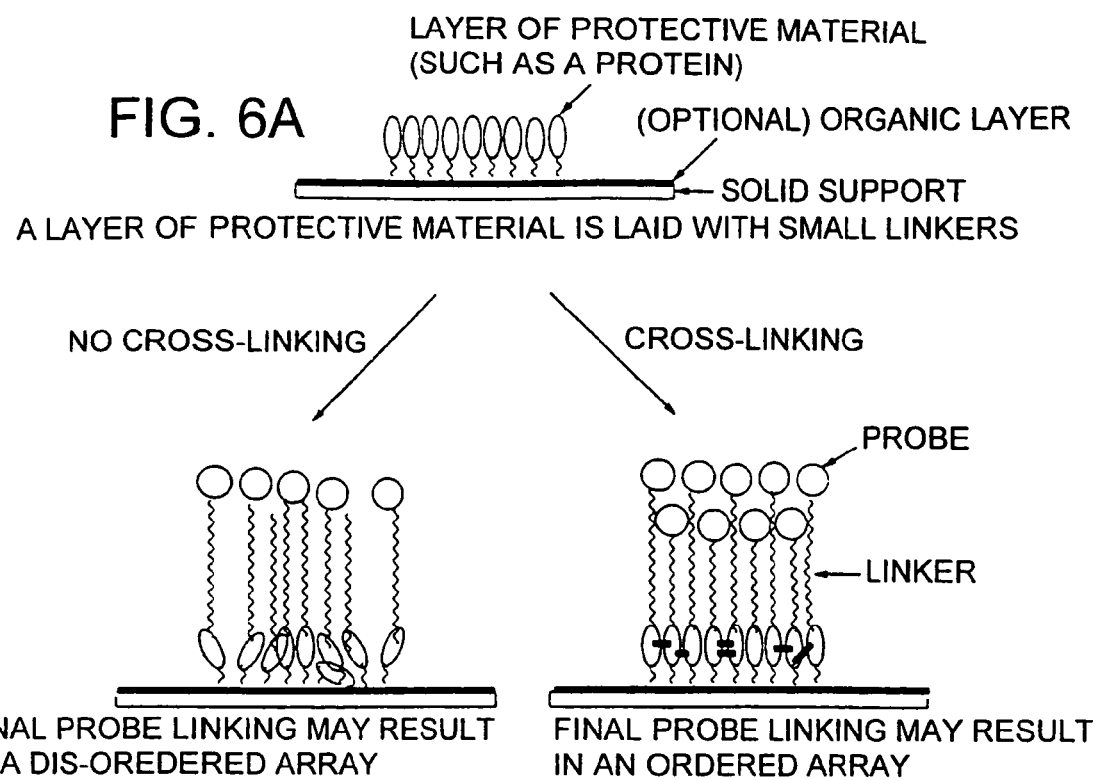

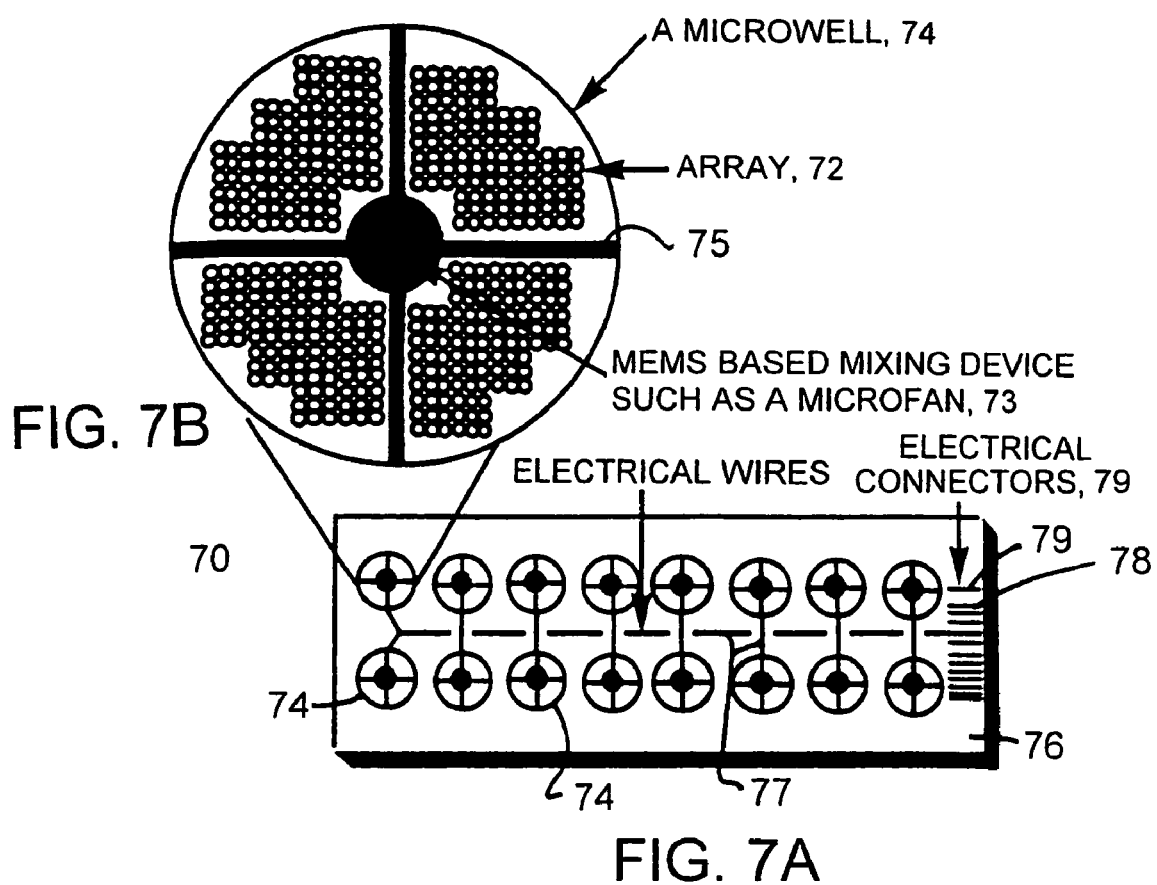

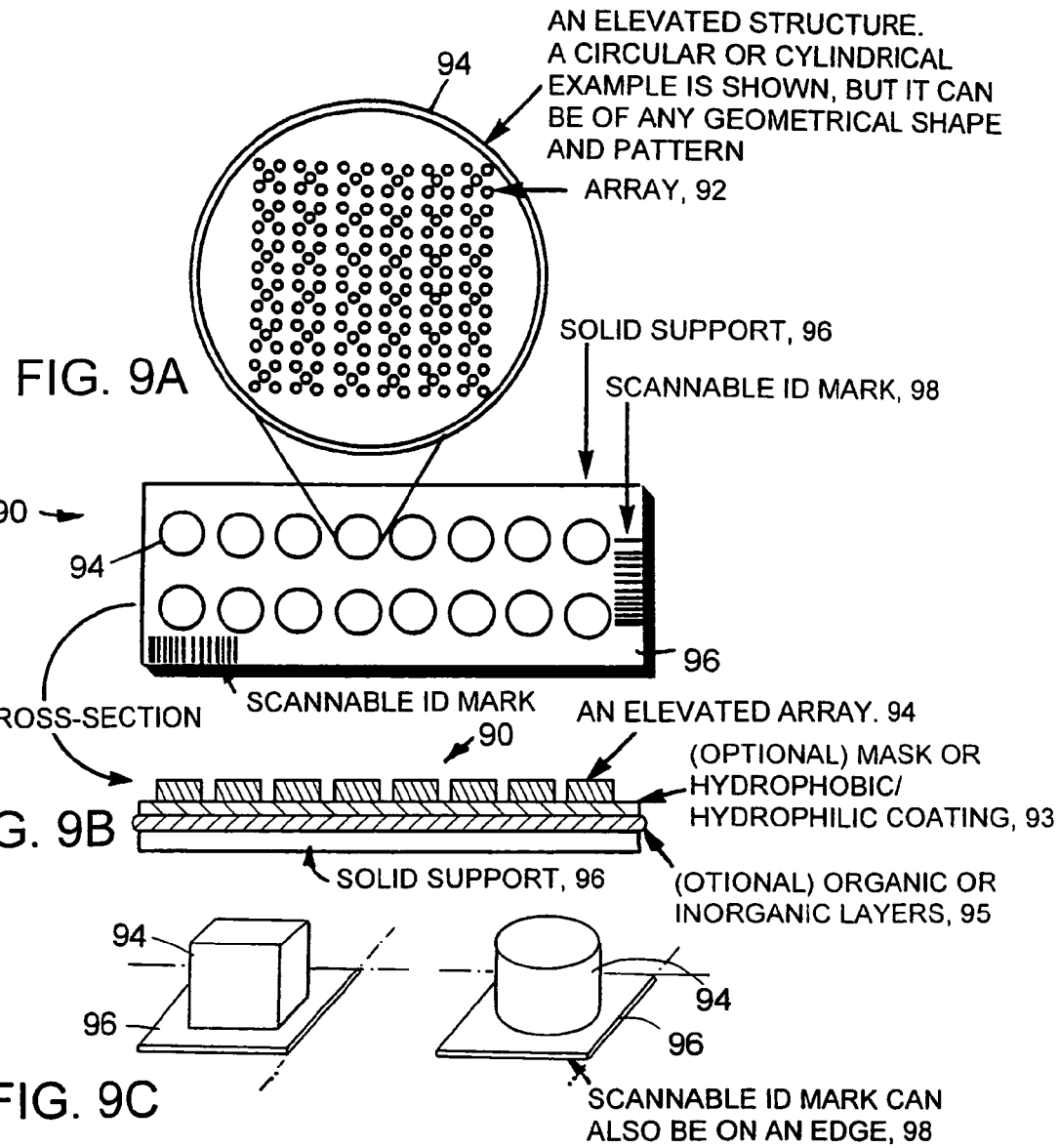

TWO VIEWS OF TWO TYPES OF "INVERTED ARRAYS"

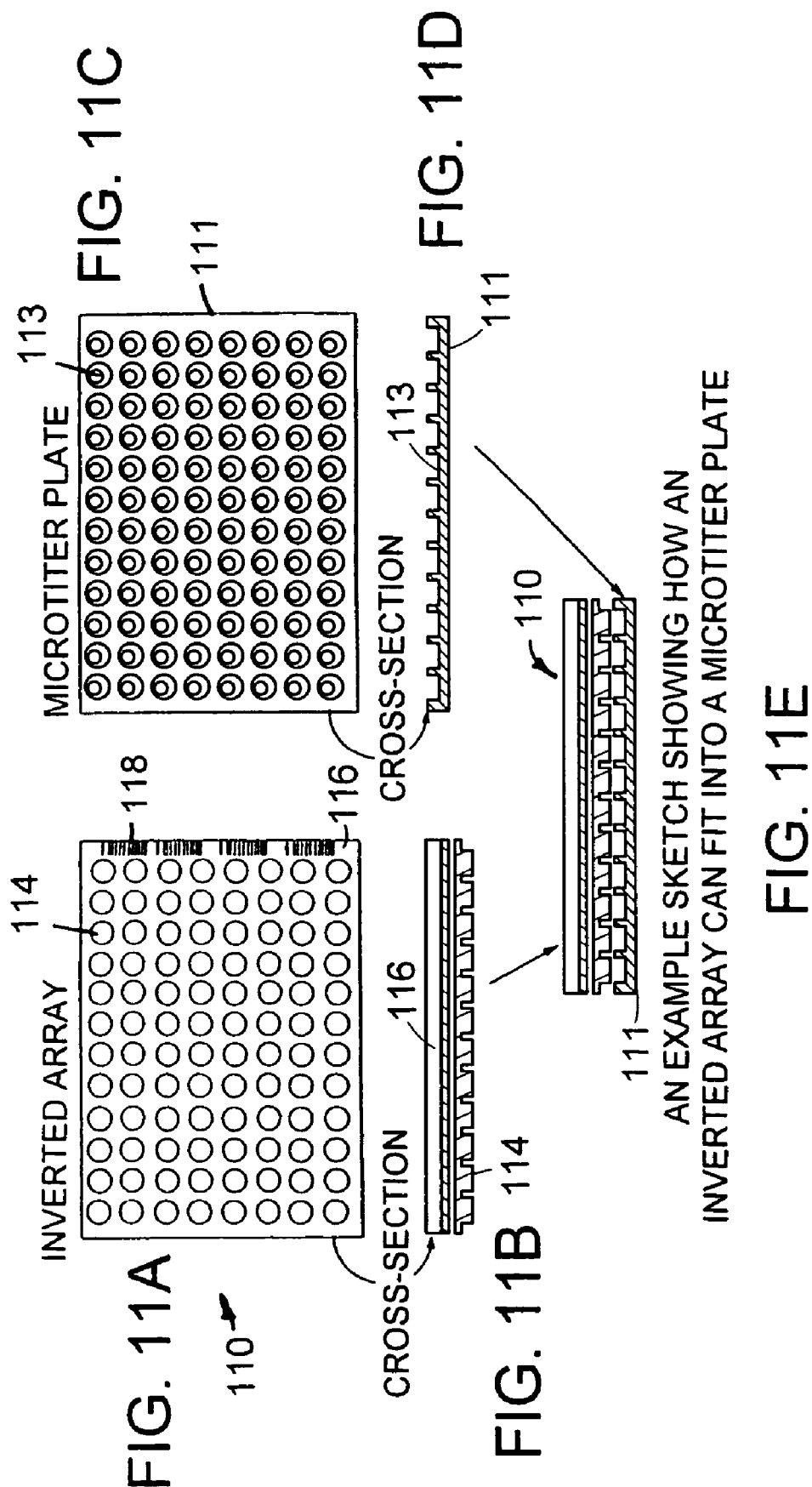

THE "INVERTED ARRAY" CAN BE MOVED FROM ONE REACTION VESSEL TO ANOTHER. IT CAN BE MOVED EITHER USING A BUILT-IN HANDLE OR USING A VACUUM SUCTION DEVICE OR ANY OTHER MECHANISM. THE PROCESS CAN BE DONE MANUALLY OR ROBOTICALLY AND THE ASSAY PROCEDURE CAN BE EASILY AUTOMATED. THIS SCHEMATIC SHOWS AN EXAMPLE OF ONE SUCH PROCESS.

Elevated sub-structure

Planar sub-structure

Depressed sub-structure

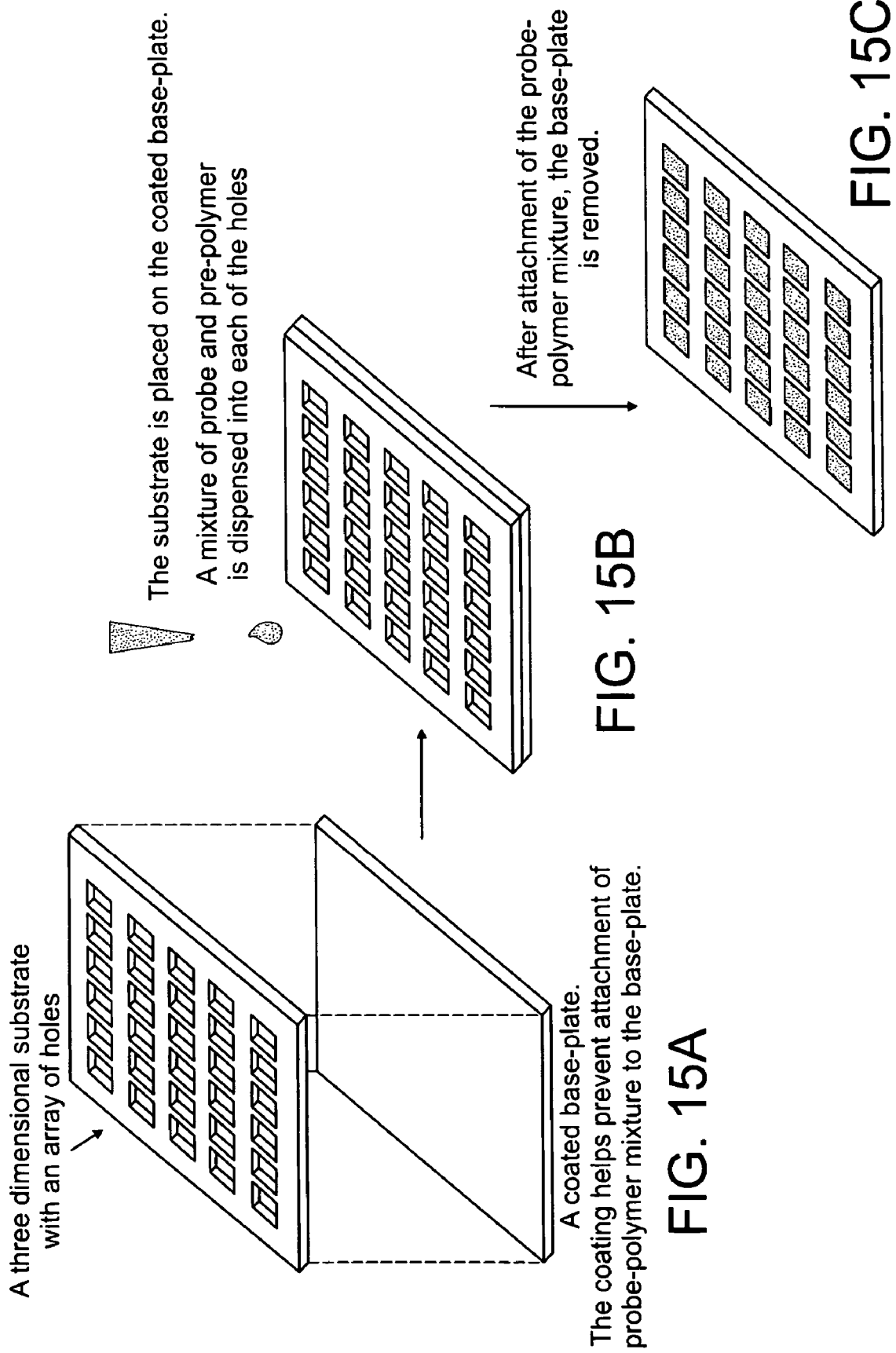

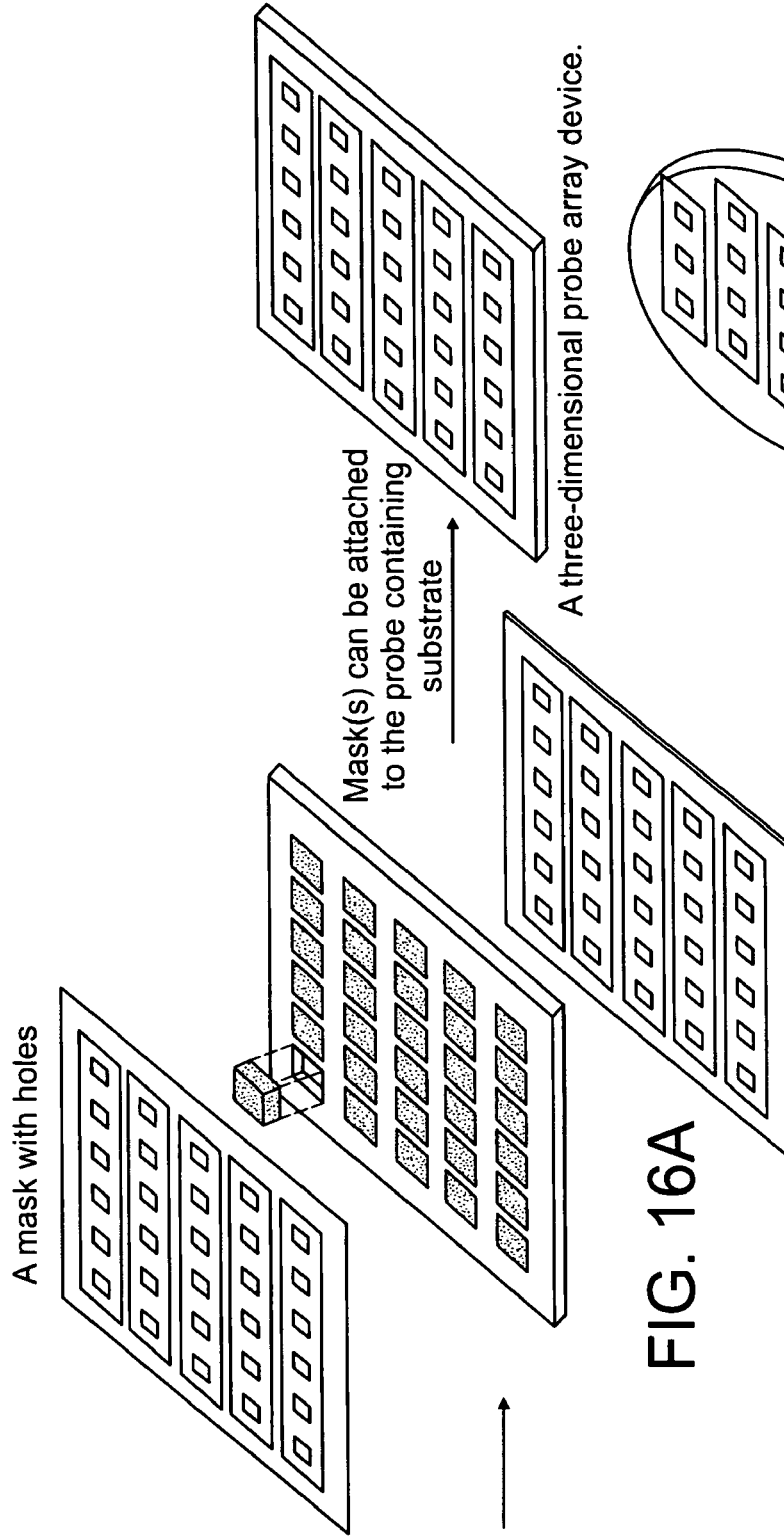

A coated base-plate with depressions or chambers to hold fluids
The coating helps prevent attachment of probe-polymer mixture to the base-plate.

Another implementation of 3D porous biochip

Probe-polymer plugs for the holes in an array

Dumb-bell shaped plugs for the holes in an array

Nitrocellulose plugs, with an optional membrane underneath

Two examples of the types of material that can be used to manufacture the 3D porous array

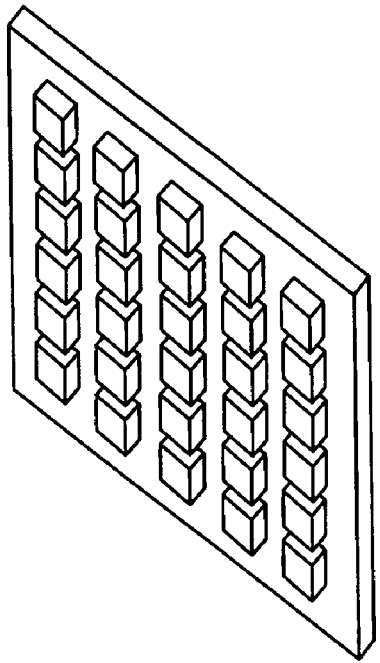
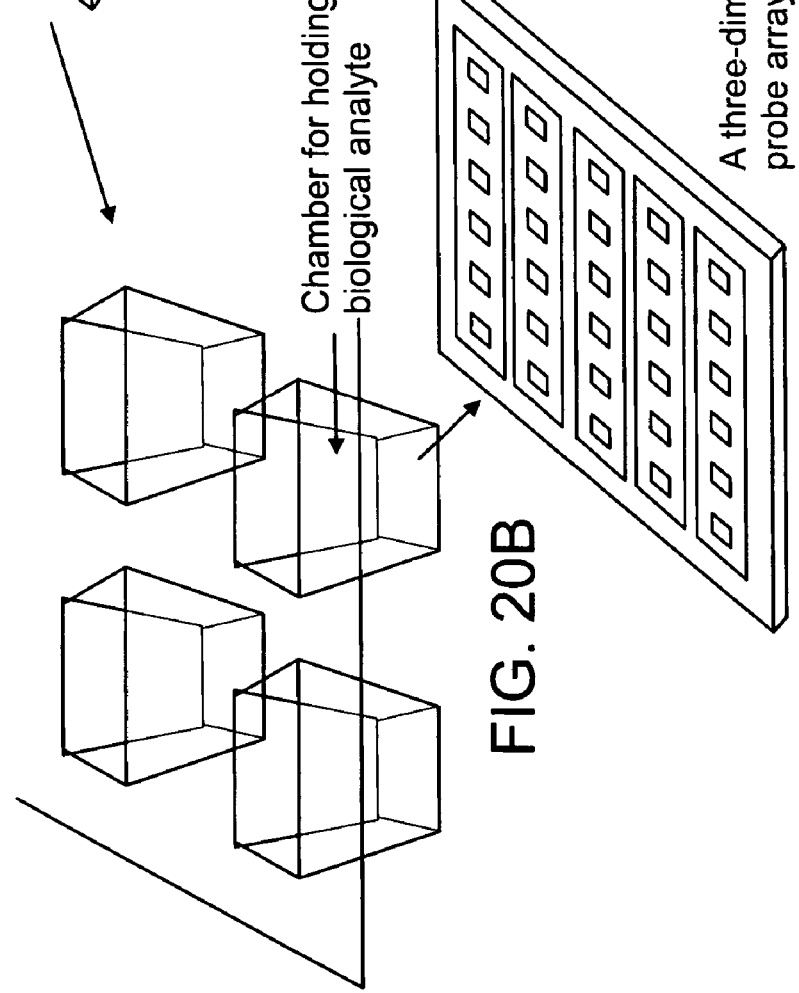
FIG. 20A
FIG. 20B
Chamber for holding biological analyte
FIG. 20C
A three-dimensional probe array.

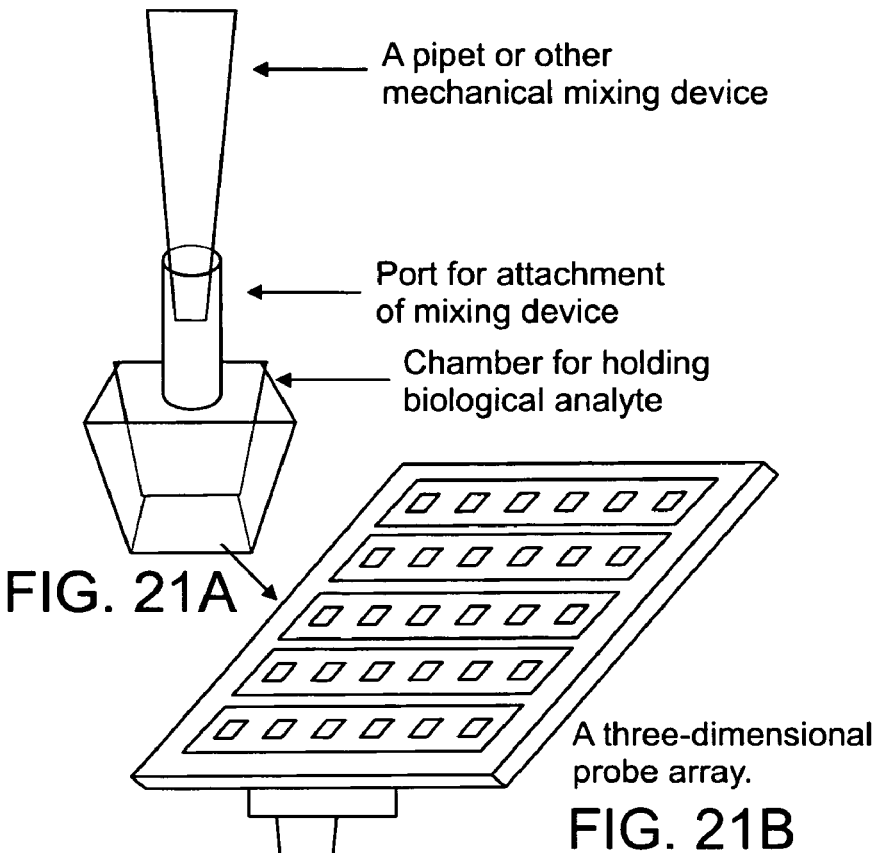
The microarray biochip can also be housed in a sealed hand-held or Point of Care device.
FIG. 21A — A pipet or other mechanical mixing device; Port for attachment of mixing device; Chamber for holding biological analyte
FIG. 21B — A three-dimensional probe array.
FIG. 21C — Another implementation of the chamber for holding biological analyte; Slits for fluid transfer A three-dimensional probe array.

ATPase-based Fluid-Micromixers

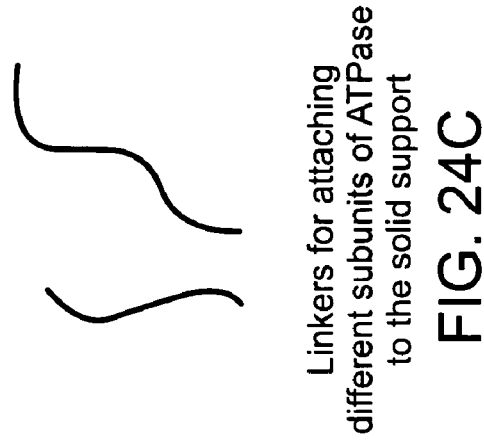

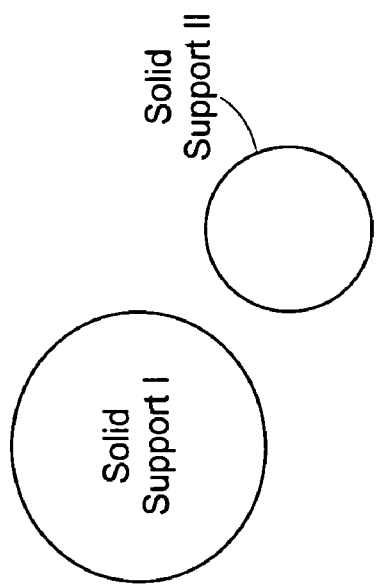

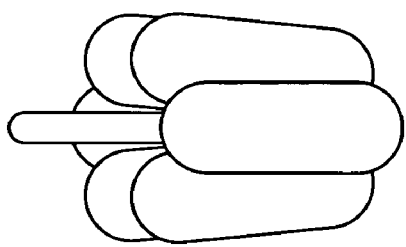

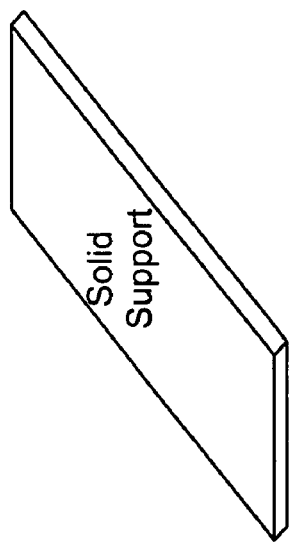

FIG. 24A Cartoon of the multi-subunit enzyme - ATPase - that rotates in response to ATP synthesis to hydrolysis. The centrally located γ-subunit rotates relative to the hexameric α,β-subunit core FIG. 24B Spherical Beads as Solid supports for attaching different subunits of ATPase FIG. 24C Linkers for attaching different subunits of ATPase to the solid support FIG. 24D Flat platform base as Solid supports for attaching one of the subunits of ATPase

ATPase-based Fluid-Micromixers, Model I

A cartoon showing ATPase subunits attached to two beads from another angle.

One particular implementation of ATPase-based fluid-micromixers. The γ-subunit and the α,β-subunit core are both attached to two different spherical beads.

A cartoon showing rotation of the two beads bound to ATPase (Model I micromixer) upon addition of ATP

ATPase-based Fluid-Micromixers, Model II

Another implementation of ATPase-based fluid-micromixers. The γ-subunit is attached to a spherical beads and the α,β-subunit core is attached to solid platform.

A cartoon showing ATPase subunits attached to two different surfaces from another angle.

A cartoon showing multiple Model II Micromixers in action in a solution

All the mixers are moving in a counter-clockwise direction

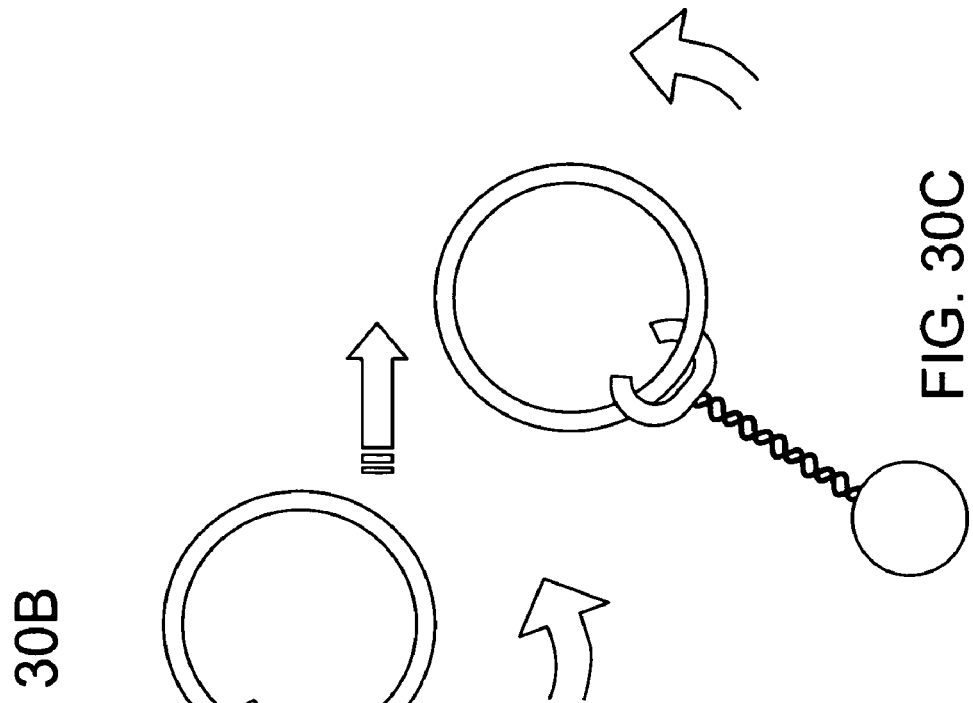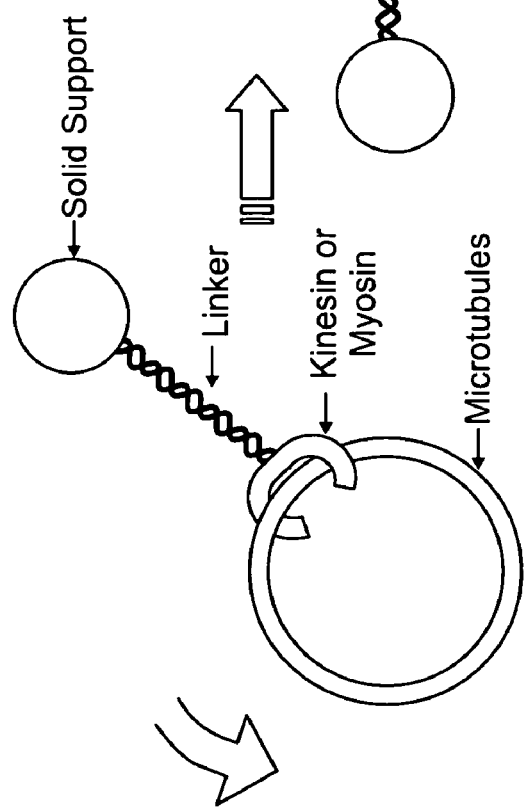

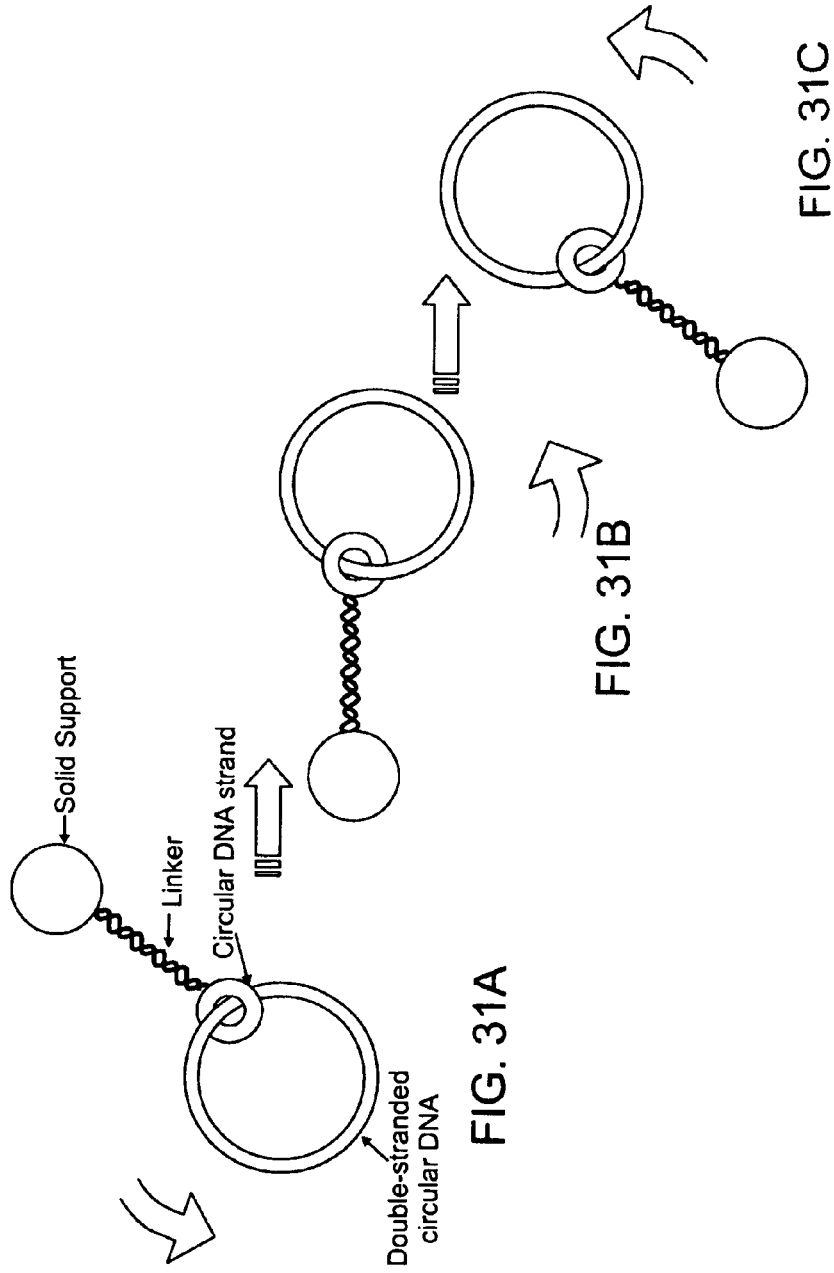

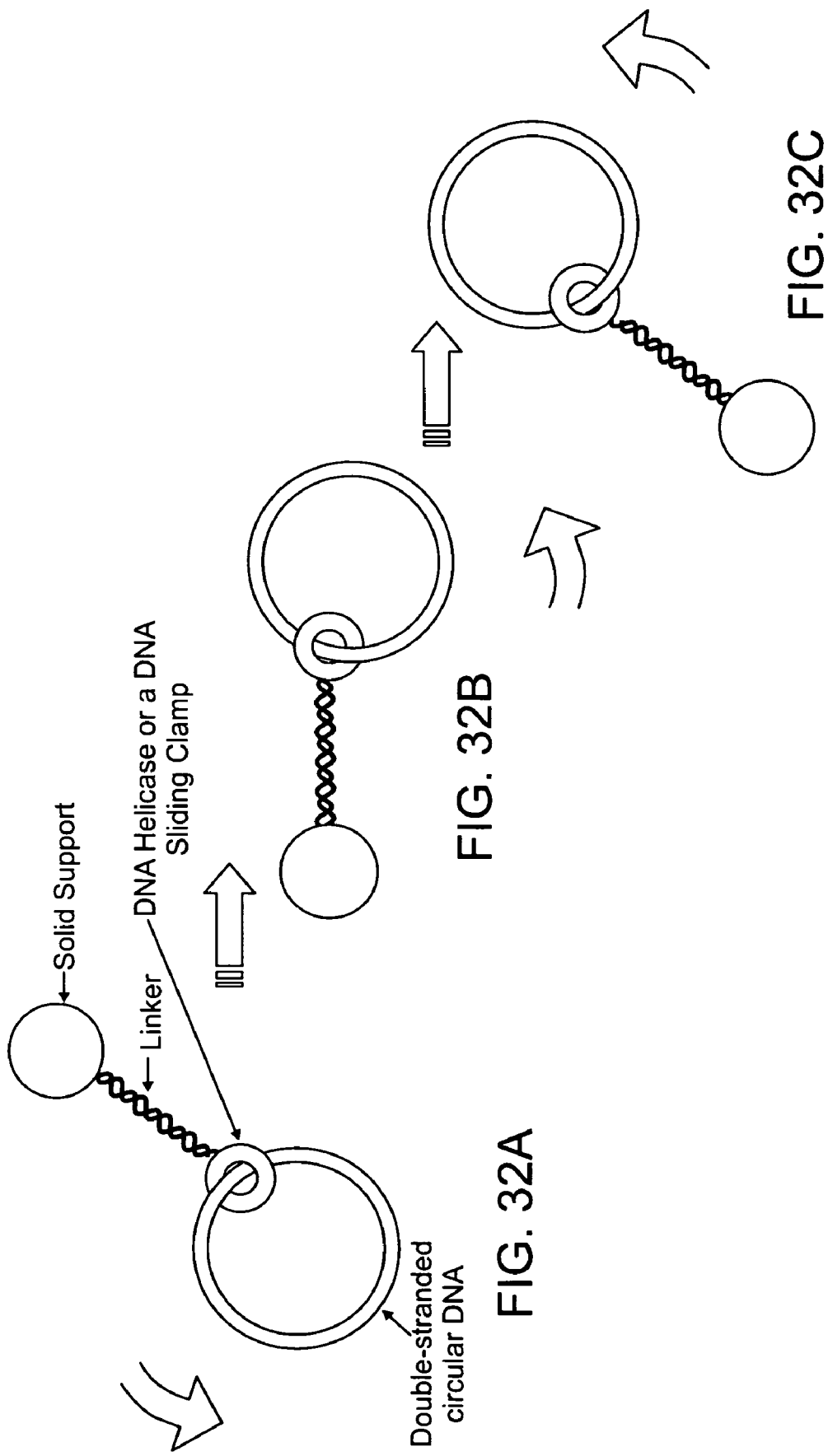

DNA Helicase (bound to Circular Triplex Forming Oligo (CTFO) or Sliding Clamp) based Fluid-Micromixers

Hybridization Enhancement Using Strand-Invader Molecules

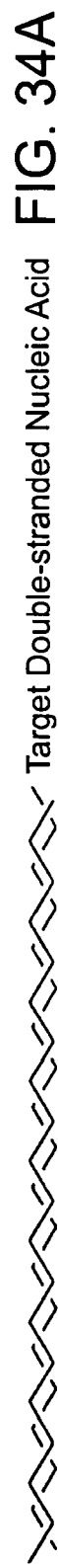
Target Double-stranded Nucleic Acid  FIG. 34A (optional) second oligo  Strand-Invader Probe  FIG. 34B

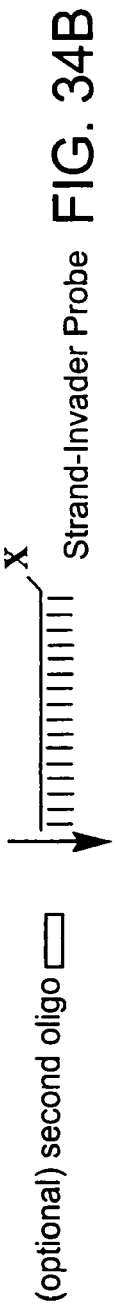
Upon Binding with Strand-Invader Target Sequence is Made Single-Stranded
FIG. 34C

Immobilized Assay Probe
FIG. 34D

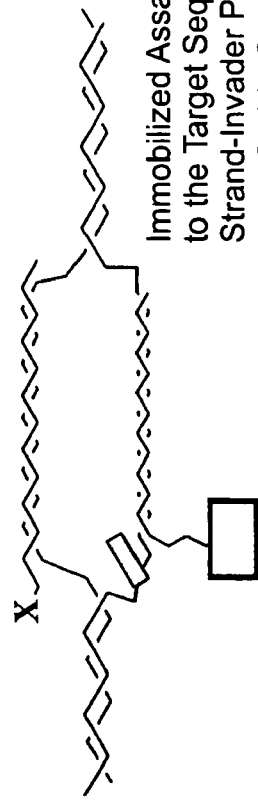
Immobilized Assay Probe Readily Binds to the Target Sequence in the Presence of Strand-Invader Probe, Forming a much more Stable Complex X = Optional Detector Moeiety

FIG. 34E

A gasket/separator can be used in the current hybridization chambers to place two biochips facing each other in a single chamber for duplicate experiments Cover plate Biochip Separator Biochip Holder A sketch of one example of a new hybridization chamber
A hybridization chamber can be devised such that it fits two biochips Hybridization Chamber Clamps I. A gasket/separator can be used in the current hybridization chambers to place two biochips facing each other in a single chamber for duplicate experiments Hybridization Chamber Clamps
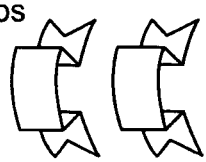
FIG. 36A

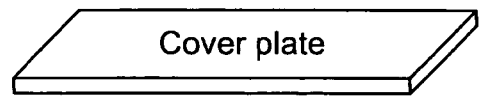
Cover plate
FIG. 36B

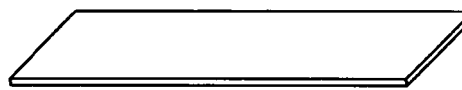
Biochip
FIG. 36C

Slot for introducing biological sample after assembly
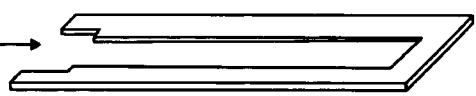
Separator
FIG. 36D

FIG. 36E

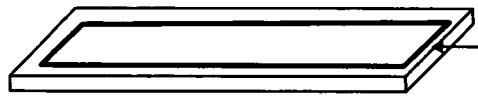
Holder
FIG. 36F

II. The separator can be built into the chamber

Hybridization Chamber
FIG. 36G

Cross-section view

Slot for introducing biological sample
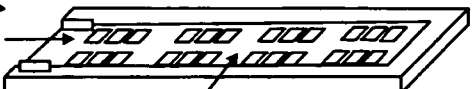
FIG. 36H

Biochip, placed into one of the grooves of a hybridization chamber

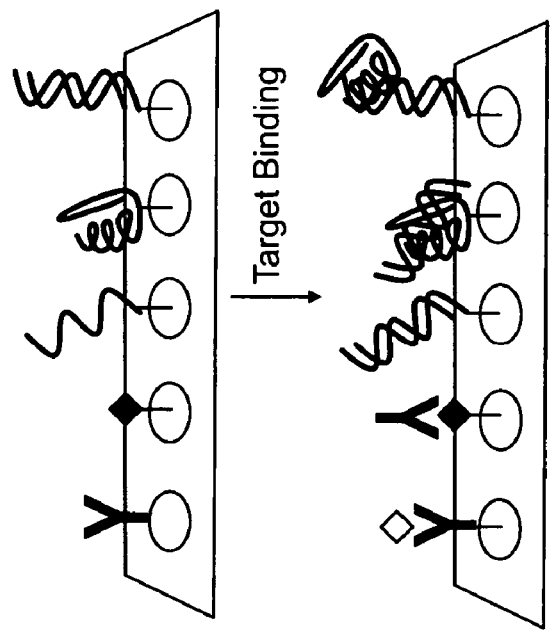
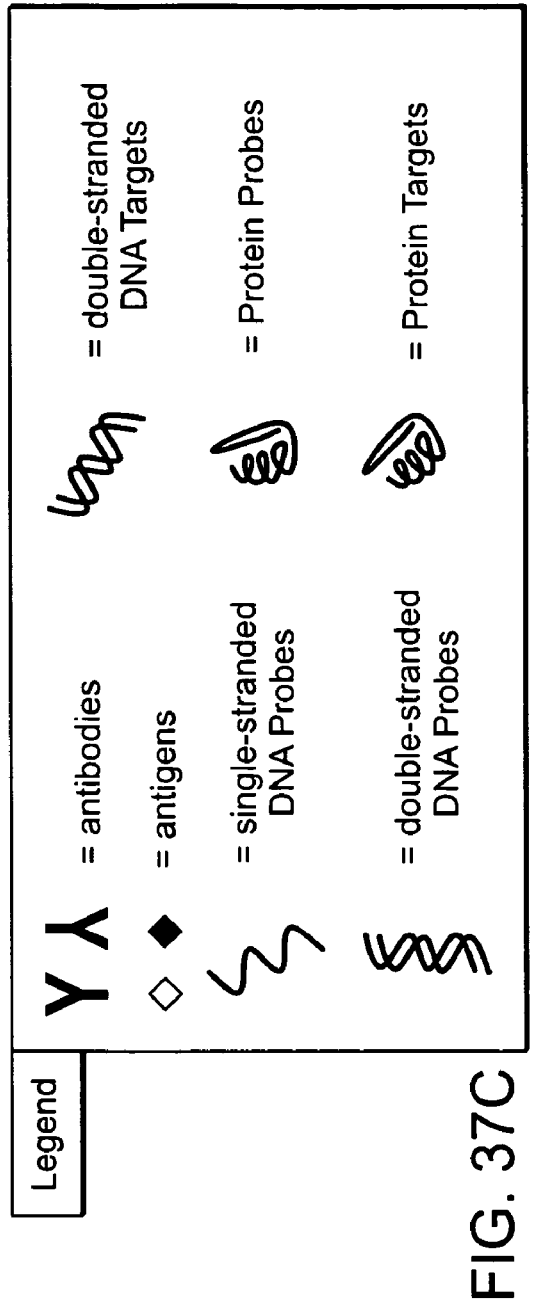
FIG. 37A
FIG. 37B
FIG. 37C

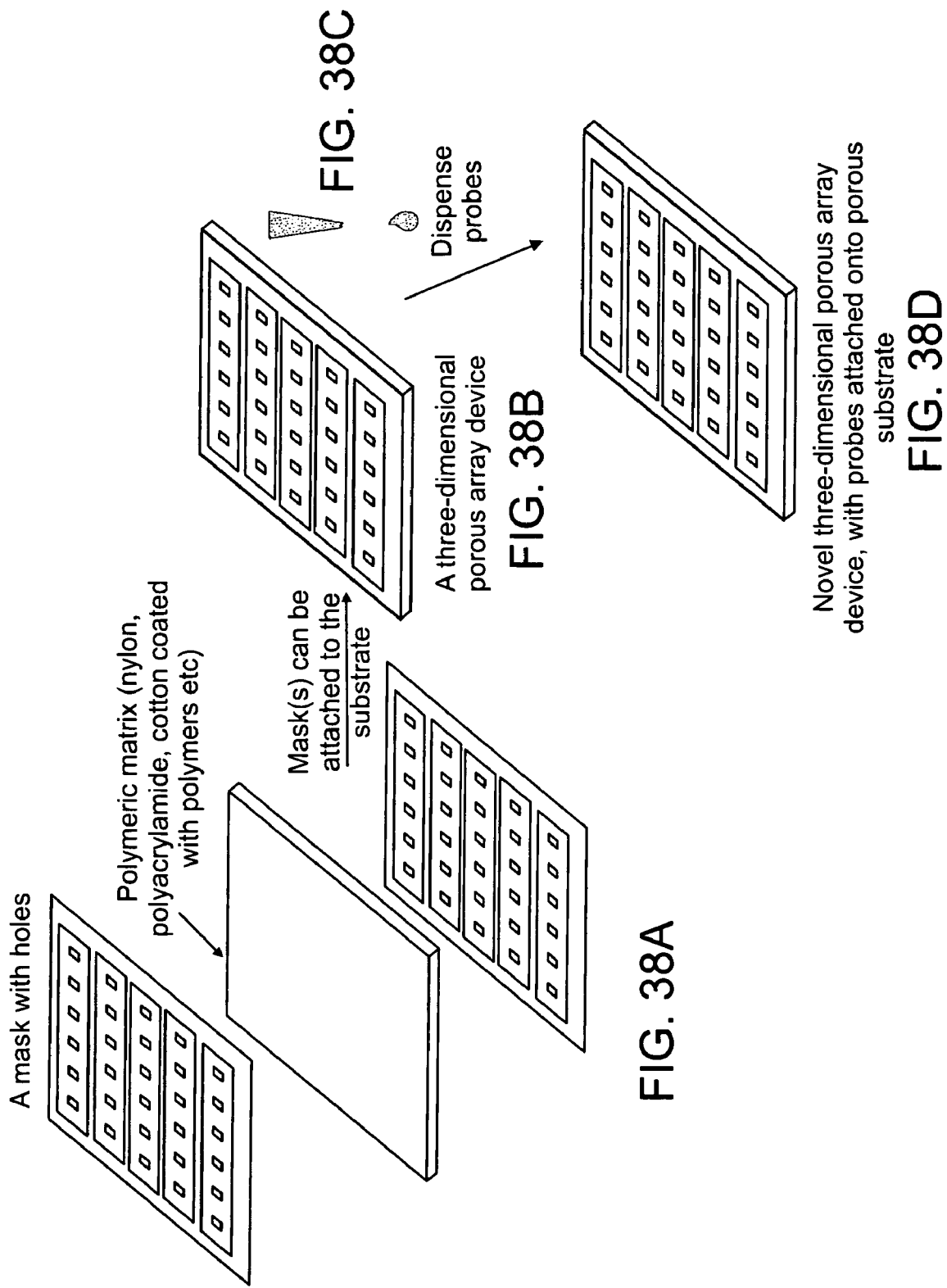

CLINICALLY INTELLIGENT DIAGNOSTIC DEVICES AND METHODS

CROSS-REFERENCE TO RELATED APPLICATIONS

This application is a divisional of U.S. patent application Ser. No. 11/102,498, filed on Apr. 8, 2005, which is a continuation of U.S. patent application Ser. No. 09/996,056, filed on Nov. 27, 2001, now U.S. Pat. No. 6,905,816, which claims priority to U.S. Provisional Patent Application Ser. Nos. 60/253,284, filed on Nov. 27, 2000, 60/287,994, filed on May 1, 2001, and 60/308,870, filed on Jul. 30, 2001, which are all incorporated by reference herein in their entirety.

FIELD OF THE INVENTION

This invention relates to medical diagnosis.

BACKGROUND OF THE INVENTION

It is common for patients to seek the advice of a physician when experiencing discomfort. However, patients seldom present physicians with a diagnosis already made; instead, they present one or more symptoms. Selecting the most probable diagnosis from a list of alternatives (hypotheses) is a process called differential diagnosis. Certain signs or symptoms can suggest a specific disease etiology. However, patients typically present physicians with clinical symptoms that are confounding, which make diagnosis based on only the symptoms very difficult. The physician has the daunting task of determining which of a number of principal etiologies is responsible for the discomfort the patient is experiencing. This is also important because selecting a specific diagnosis has implications for the treatment plan and therapy. The symptoms prompt the physician to gather information through history, physical examination and, most importantly, diagnostic tests identifying clinical findings that suggest explanations for the symptom(s).

Thus, diagnostic tests, both performed at a laboratory and at the point-of-care (POC), are an integral part of the health care system. Such tests play a central role in all aspects of patient care, including disease-diagnosis, monitoring progression of therapy, as well as screening for health and infection. Molecular diagnostics tests (such as in vitro diagnostic (IVD) tests) are especially useful, as they pinpoint the exact cause of a particular clinical manifestation and thus help the physician to make a diagnosis and then prescribe the right treatment and therapy.

Currently, the diagnostic testing process is very tedious, time-consuming, cumbersome, and slow. This is because a number of different tests often have to be performed for a given symptom and each of these tests is performed individually. Moreover, because laboratories are constantly updating and adding new tests that facilitate medical diagnosis, physicians regularly confront dilemmas when ordering and interpreting these tests. Over the last two decades, the total number of clinical tests and the types of different tests available to physicians has grown exponentially. These advances in modern clinical laboratory medicine, though enormously helpful, also create new problems. These tests are often not user friendly, and increase costs in an already heavily burdened health care system. In common practice, physicians also complain about the delay in the processing of tests at the laboratories thus delaying accurate patient diagnosis. Additionally, many tests are not available at all, are available at only one or two testing sites/laboratories, or are known only to specialists.

Effective management of diseases requires an awareness of the full spectrum of etiologies and their possible complications. Sometimes the initially chosen set of tests present results that are not clear, which precludes an accurate diagnosis. The nature and relatively non-specific symptoms of the disease can make a proper diagnosis challenging. In such cases more tests are performed, which are run in an iterative and sequential fashion. Thus, testing slows down the entire process of patient care and treatment, which is costly, and is detrimental to the patient's health and treatment plans.

SUMMARY OF THE INVENTION

The present invention relates to the clinically intelligent design of diagnostic devices (such as microarrays) and the methods of making and using such devices in differential analyses/diagnoses of specific clinical symptoms or sets of symptoms. In one aspect, the devices include various probes used to perform parallel screening of a number of analytes. The probes are clustered on the devices based on known clinical presentations of symptoms associated with specific diseases and disorders. In another aspect, the devices are used to perform parallel screening of a number of clinically associated analytes, such as known blood-borne pathogens and antibodies. In yet another aspect, these devices are used to perform parallel screening of analytes found in agricultural, forensic, veterinary, and other samples.

In general, the invention relates to a method of determining a cause of one or more medical symptoms exhibited by a subject by (a) obtaining a biological sample from the subject; (b) obtaining an array of different probes or different sets of probes, wherein each probe or set of probes selectively interacts with a target associated with a different known cause of the one or more medical symptoms; (c) applying the biological sample to the probes in the array under conditions that enable all of the probes to selectively interact with any targets in the biological sample; (d) detecting interactions; and (e) analyzing interactions to determine a cause of the one or more medical symptoms. In this method, the array of probes or sets of probes can be arranged on a planar substrate. The target can be a nucleic acid, peptide, polypeptide, protein, antibody, antigen, small organic molecule, inorganic molecule, enzyme, or polysaccharide. All of the probes in the array can be polypeptides, e.g., antibodies, antigens, enzymes, zinc-finger binding proteins, minor-groove binders, transcriptional factors, combinations thereof, or chimeras thereof.

In these methods, the subject can be a plant or animal, or a human patient or a deceased human. In certain embodiments, the probes can be expressed on the surface of genetically modified cells, and the probes can selectively interact with a target by specifically binding to the target to form a complex. In certain embodiments, the array of probes can include a first probe that selectively interacts with a target associated with an infectious disease caused by a bacteria, virus, or fungus, and a second, different probe selectively interacts with a target associated with a genetic cause. The array of probes can also include probes that assay for the absence of a causative agent of one or more medical symptoms.

In another aspect, the invention features a method of determining the susceptibility of a subject to a cause of one or more medical symptoms, by: (a) obtaining a biological sample from the subject; (b) obtaining an array of different probes or different sets of probes, wherein each probe or set of probes selectively interacts with a target associated the susceptibility of the subject to a different cause of the one or more medical symptoms; (c) applying the biological sample to the probes in the array under conditions that enable all of the probes to selectively interact with any targets in the biological sample; (d) detecting interactions; and (e) analyzing interactions to determine the susceptibility of the subject to a cause of the one or more medical symptoms.

In the new methods, all of the probes can be designed to selectively interact with their respective targets under the same conditions.

In another aspect, the invention also includes a method of determining a cause of one or more medical symptoms in a subject and assessing the suitability of one or more therapeutic agents to treat the cause of the symptoms by: (a) obtaining a biological sample from the subject; (b) obtaining an array of different probes or different sets of probes, wherein a first probe or set of probes selectively interacts with a target associated with a known cause of the one or more medical symptoms, and wherein a second, different probe selectively interacts with a target associated with a therapeutic optimization factor; (c) applying the biological sample to the probes in the array under conditions that enable all of the probes to selectively interact with any targets in the biological sample; (d) detecting interactions; and (e) analyzing interactions to determine a cause of the one or more medical symptoms and to determine the suitability of a therapeutic agent to treat a cause of the one or more symptoms. In this method, the therapeutic optimization factor can be tolerance, intolerance, or susceptibility of the subject or a causative agent to a specific drug, and the target associated with the therapeutic optimization factor can be a gene in a pathogen that causes susceptibility, resistance, or an idiosyncratic reaction of the pathogen when exposed to a therapeutic agent.

In other embodiments, the invention also features devices. For example, the devices can include (a) a substrate having a surface, wherein the surface includes a plurality of protrusions having top surfaces; and (b) an array of probes or sets of probes, wherein each probe or set of probes selectively interacts with a unique target, and is attached to the top surface of one of the protrusions. The substrate can be silicon, silicon dioxide, glass, polystyrene, gold, metal, metal alloy, zeolyte, polymer, or other organic or inorganic molecule.

The devices can also include (a) a substrate having a surface, wherein the surface comprises multiple wells, each well comprising a micromixer; (b) a micromotor connected to each micromixer; and (c) an array of probes or sets of probes, wherein each probe or set of probes in the array selectively interacts with a unique target and is attached within one of the wells. In certain embodiments, the micromixer is a microfan blade, and the micromotor is an electromagnetic, a chemical, or a biological motor.

Another device includes (a) a substrate having a surface, e.g., a planar surface; (b) an array of probes or sets of probes, wherein each probe or set of probes in the array specifically binds to a unique target; and (c) an set of linkers, wherein the linkers bind the probes to the surface, and wherein the linkers have different lengths. The linkers can be molecules of polyethylene glycol.

In another aspect, the invention features a diagnostic system that includes a plurality of devices of the invention, wherein each device includes an array of different probes or different sets of probes, and wherein each probe or set of probes selectively interacts with a target associated with a different known cause of a medical symptom or a set of related medical symptoms. The invention also includes a method of determining a cause of one or more medical symptoms exhibited by a subject by (a) assessing the subject's symptoms; (b) selecting one of the new devices from the diagnostic system; (c) obtaining a biological sample from the subject; (d) applying the biological sample to the probes on the device array under conditions that enable all of the probes to selectively interact with any targets in the biological sample; (e) detecting interactions; and (f) analyzing interactions to determine a cause of the one or more medical symptoms. This method can further include analyzing interactions to determine the suitability of a therapeutic agent to treat a cause of the one or more symptoms.

In these methods, the cause can be a fungal, bacterial, viral, or other microbial cause, genetics or another cause or a combination of causes. The cause can also be vascular, infection/inflammation/autoimmune, neoplasm, drugs, iatrogenic, congenital/developmental/inherited, or environmental exposure/endocrine/metabolic. The sample can be blood, cerebrospinal fluid, urine, sweat, buccal or other swab, a cell sample, or a cell culture. The protein analytes can be antibodies, antigens, glycoproteins, or enzymes. The nucleic acid analytes can be single-stranded or double stranded, DNA or RNA, or a DNA-RNA complex/hybrid or a cell. Furthermore, the probes can be attached to the substrate using covalent or non-covalent bonds. For example, the probes can be attached to the substrate using amide or thiol bonds.

In the devices, the wells can have micromixers, such as fans, and can further include electrical connections, wherein the electrical connections connect the mixing devices to an energy, e.g., voltage, source. In addition, the micromixers can be biological molecules powered by micromotors that run on biologic reactions, e.g., based on ATPase, kinesin, kinesin related proteins, myosin, DNA Helicase, DNA Sliding clamps, nucleic acid based rotaxanes and Pseudo-rotaxanes, circular triplex forming oligonucleotides (CTFO), duplex DNA; as well as chimeras and derivatives of such proteins and nucleic acids. The protrusions or wells can have mixing device(s) powered by electromagnetic radiation or the piezoelectric effect or other sources of energy.

In other embodiments, the invention features methods for intelligently clustering probes in kit design; reagents and kits for use in the new devices/systems, methods for interpreting the data and results as well as making a recommendation for diagnosis; methods for immobilizing biomolecules in such a manner that their activity is largely preserved (e.g., by the use of cross-linked streptavidin and other protein layers for attaching capture probes, or spotting solutions with reagents that help in stabilizing/preserving biological activity of the probes); methods of dispensing probes in one or more replicates and in geometric patterns that provide a read-out that can be easily converted to a result by simple visual inspection (e.g., in "X" patterns); methods for image storage and processing, and manipulating stored signals to form a new image; new systems/devices that will combine the sample collection modules with the diagnostic devices into a single combination device/system (that circumvent the need to transfer biological samples from collection tubes to diagnostic devices); new systems/devices in which the sample collection module is separate from the diagnostic device module and is easily attached together at any stage, without having to take the sample manually out of the collection module; methods of preserving the developed slides (e.g., by keeping them sealed in aqueous buffer, e.g., containing BSA, milk proteins, glycerol, trehalose or other such reagents that preserve the activity of attached probes; methods for performing automated processing of slides (including screening, scanning and delivery of results); methods of selecting and using either single unique probes for each analyte or multiple unique probes for each analyte; and methods for placing optical positioning markers for automated image processing and read-out (e.g., that can include a row of dilution series for dynamic range determination and internal calibration on the biochip/microarray).

Unless otherwise defined, all technical and scientific terms used herein have the same meaning as commonly understood by one of ordinary skill in the art to which this invention belongs. For example, definitions of common terms in molecular biology can be found in Benjamin Lewin, Genes VII, published by Oxford University Press, 2000 (ISBN 0-19-899276-X); Kendrew et al. (eds.), The *Encyclopedia of Molecular Biology*, published by Blackwell Science Ltd., 1994 (ISBN 0-632-02 182-9); Robert A. Meyers (ed.), *Molecular Biology and Biotechnology: a Comprehensive Desk 10 Reference*, published by VCH Publishers, inc., 1995 (ISBN 1-56081-569-8); and *Harrison's Principles of Internal Medicine,* 12th Ed., published by McGraw-Hill, New York, U.S.A., 1991.

A symptom is a measurable and/or observable indication of a disease or disorder. A symptom can be exhibited by any subject, such as a human patient, any animal (e.g., a bird, such as poultry, or a mammal such as a domestic animal such as a dog, cat, cow, pig, or horse), or even a plant that is diseased.

A probe is an antibody, antigen, protein, nucleic acid such as RNA or DNA, or other molecule or compound that interacts with (e.g., specifically binds to or causes a measurable reaction with) a target or analyte. A target or analyte is a marker for a disease, disease etiology, disorder, treatment, etc., and is thus associated with a possible cause for the one or more symptoms of a specific disease or disorder. For example, a target can be an antigen expressed by a microbe, such as a bacterium, virus, fungus, or even a pathogenic plant such as algae. A target can also be a biological or chemical molecule produced by a microbe, such as an enzyme, a toxin, or a nucleic acid (such as DNA or RNA), or even a small organic molecule, or an inorganic compound, such as a liquid or gas. A target can also be a specific genetic sequence indicative of a genetic disorder of the subject being tested. For example, a genetic disorder can be marked by a mutation of a gene, a single nucleotide polymorphism (SNP), an extra copy of a normal chromosome or gene, or a missing gene. A target can also be a marker for a therapeutic optimization factor, such as a microbial gene that provides resistance, tolerance, or susceptibility to a particular drug. Such a therapy optimization factor can also be a genetic feature of the subject that makes the subject resistant, tolerant, or intolerant (e.g., allergic) to a particular drug.

In each case, the target is detected and/or quantitated by a probe. The probe binds specifically to the target, which is associated with one or more symptoms of a specific disease or disorder. Thus, an interaction of the probe with a target, e.g., binding to form a complex, indicates the presence of a specific cause for the one or more symptoms.

Genetic analysis is the detection or measurement of any target or analyte that has a genetic basis or cause, e.g., a single nucleotide polymorphism in a nucleic acid sequence, or the presence or absence of a specific nucleic acid sequence. Genetic analysis also includes the measurement, either qualitative or quantitative, of any endogenous physiologic analyte, such as an mRNA for a specific protein, a specific protein, or a metabolic product. In addition, genetic analysis includes detecting a specific epitope of an antibody or an antigen.

A "genetic cause" is any cause that has a nucleic acid basis. For example, a genetic cause can be a single nucleotide polymorphism in a nucleic acid sequence. It can also be the presence or absence of a nucleic acid sequence. A genetic cause can be determined by the presence of a specific epitope of an antibody or an antigen, or a specific conformation of a protein.

Clinically Intelligent Design is a method of clustering a set or sets of probes for analyzing targets based on which targets would be detected for a given symptom. This method differs from clustering probes simply based on the compatibility of different tests in a single assay. Rather, only those tests that pertain to the analysis of one or more specific symptoms are clustered together. Thus, the method incorporates clinical intelligence in designing and selecting the probes that are clustered in a single assay.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides several advantages. Physicians and/or clinicians receive a large spectrum of information rapidly by using the new devices, and laboratories benefit because the new diagnostic kits require only small amounts of reagents and samples. All relevant tests for a given symptom can be rapidly analyzed with one device, under the same reaction conditions, thereby reducing test costs, while providing a comprehensive, standardized result in a rapid fashion. Subjects to be tested, such as human patients, benefit significantly because they can receive a better and quicker diagnosis from their physicians compared to the situation in which patients are subject to a battery of tests requiring multiple samples.

The new devices/systems also decrease the risk to health care workers by simplifying assay procedures, reducing sample size, and decreasing the amount of handling of donor samples required (by reducing the total number of separate/individual tests required in a screening procedure), and thereby reduce the risk of infection.

In addition, the new methods and devices provide facile and low cost alterations and augmentations of the devices to include additional tests, which is cheaper than the laborious and costly process of adding new tests to a battery of tests conducted separately, each using a separate sample, e.g., from an individual subject.

Another advantage is that it provides a method for detecting almost any biological analyte, such as nucleic acids as well as non-nucleic acid components, in a mixture simultaneously. The new devices can also be used for parallel processing of a large number of (same or different) samples, providing a high-throughput environment. For example, multiple sets of microarrays can be deposited onto a single biochip, which enables screening of multiple patient samples.

The new systems also provide easy and simple read-out of results by simple visual inspection, and in some embodiments simplify sample handling by combining sample collection and analysis modules to circumvent the need to transfer biological samples from collection tubes to diagnostic devices. The new methods and devices can also provide better and newer sample mixing during an assay, which improves the quality as well as reduces the time needed to perform an assay.

Another advantage is that the microarray-based diagnostic methods can be easily automated and the new devices can be used with the robots and technologies currently used in most clinical testing laboratories. This will cut down on the costs for incorporating this new technology into an existing laboratory. In addition, the microarray-based diagnostic methods can be carried out with portable devices.

Other features and advantages of the invention will be apparent from the following detailed description, and from the claims.

BRIEF DESCRIPTION OF THE DRAWINGS

FIG. 2A illustrates probes in an "X" configuration, FIG. 2B shows probes in a "V" configuration, and FIG. 2C shows probes in a "+" configuration.

FIGS. 3A to 3C are schematic drawings of symptom-specific, diagnostic biochip devices using a 16-microwell format. FIG. 3A is a top view of an enlarged microwell and a solid support, FIG. 3B is a cross-sectional view, and FIG. 3C is a view of one micro-well in three dimensions.

FIGS. 4A and 4B are schematic drawings of a new probe attachment technology using molecular linkers, such as polyethylene glycol (PEG), to attach the probes to a solid support. This new attachment technology can be used in conjunction with the new symptom-specific, diagnostic biochip devices.

FIGS. 5A to 5C are schematic drawings of another novel attachment technology using a three-dimensional covalently linked mesh of streptavidin. FIG. 5A shows a solid support with protective material, but no probes. FIG. 5B shows a solid support with probes and protective material without cross-linking (a dis-ordered array). FIG. 5C shows a solid support with protective material that is cross-linked into an ordered array.

FIGS. 6A to 6C are schematic drawings of the streptavidin attachment technology showing the use of a protective layer (6A) and molecular linkers that have different lengths, and the differences between cross-linking (6C) and not cross-linking the linkers (6B).

FIG. 7A is a schematic drawing of a mixing system incorporated into a multiwell biochip device.

FIG. 7B is an enlarged view of a single well in the multiwell biochip of FIG. 7A.

FIGS. 9A to 9C are a schematic drawings of a new inverted array system of multiwell device, that can be used with symptom-specific, diagnostic biochip devices. The substrate includes raised or elevated structures, such as cylinders, onto which specific probe arrays, or arrays of arrays, can be deposited. FIG. 9A shows an enlarged well of the multiwell device shown in FIG. 9B. FIG. 9B shows a cross-sectional view, and FIG. 9C shows three-dimensional views of the wells in the multiwell device.

FIGS. 11A to 11E are a series of schematic diagrams of an alternative inverted array system (top view, FIG. 11A, cross-sectional view, FIG. 11B) as used with a microtiter plate (top view FIG. 11C, cross-sectional view, FIG. 11D). FIG. 11E shows the inverted array inserted into the microtiter plate.

FIG. 13A shows an array of 96 elevated structures in a device. FIG. 13B shows an array of 16 elevated structures in a device. FIG. 13C shows a square-shaped elevated structure, with 30 such structures in a device. The device can also have edge-features that help with the correct alignment of these devices with microwell plates or with use of these devices in an automated fashion.

FIG. 14A shows an array of 96 elevated structures in a device. Each elevated structure can have a number of probes attached in an array or an array of arrays format. The surface of the elevated structure can also a have three-dimensional nature. In cross-section, the array of FIG. 14A can have an elevated sub-structure (14B), a planar sub-structure (14C) or a depressed/dimpled sub-structure (14D) such that one probe is attached to each of these sub-structures or features.

FIGS. 15A to C and FIGS. 16A to C are schematic representations of a three-dimensional porous array. Such a three-dimensional porous arrays can be manufactured in a number of ways and these figures illustrate one methodology in which the three-dimensional solid-substrate is an array filled with holes. The holes are filled with a gel-like matrix or other materials such as nitrocellulose membranes. The probes can either be pre-bound to the matrix or can be placed subsequent to matrix deposition step.

FIGS. 20A to C are schematic diagrams of another three-dimensional porous array based inverted array device. Each elevated structure can be based on the 3-D porous array format.

FIGS. 21A to E are representations of a point-of-care device implementation of the 3-D porous array format. This is just one example of how this format can be used in point of care biochip devices.

FIGS. 24A to D through FIG. 29 are schematic drawings of a variety of ATPase-based fluid micromixers.

FIGS. 30A to C through FIGS. 33A to C are a series of schematic drawings of additional biological molecule-based fluid micromixers.

FIGS. 34A to E are a series of representations showing how strand-invader molecules can achieve hybridization enhancement.

FIGS. 35A to G and FIGS. 36A to H are a series of schematic drawings of novel hybridization chambers and their various parts.

FIGS. 37A to C are a series of representations of the principal behind the new UniScreen Technology, which allows detection of any analyte, such as DNA, RNA, and proteins, in a single multiplexed assay.

FIGS. 38A to D are representations of a three-dimensional porous array device with probes attached to the porous substrate.

Like reference symbols in the various drawings indicate like elements.

DETAILED DESCRIPTION OF THE INVENTION

Figure 1A:
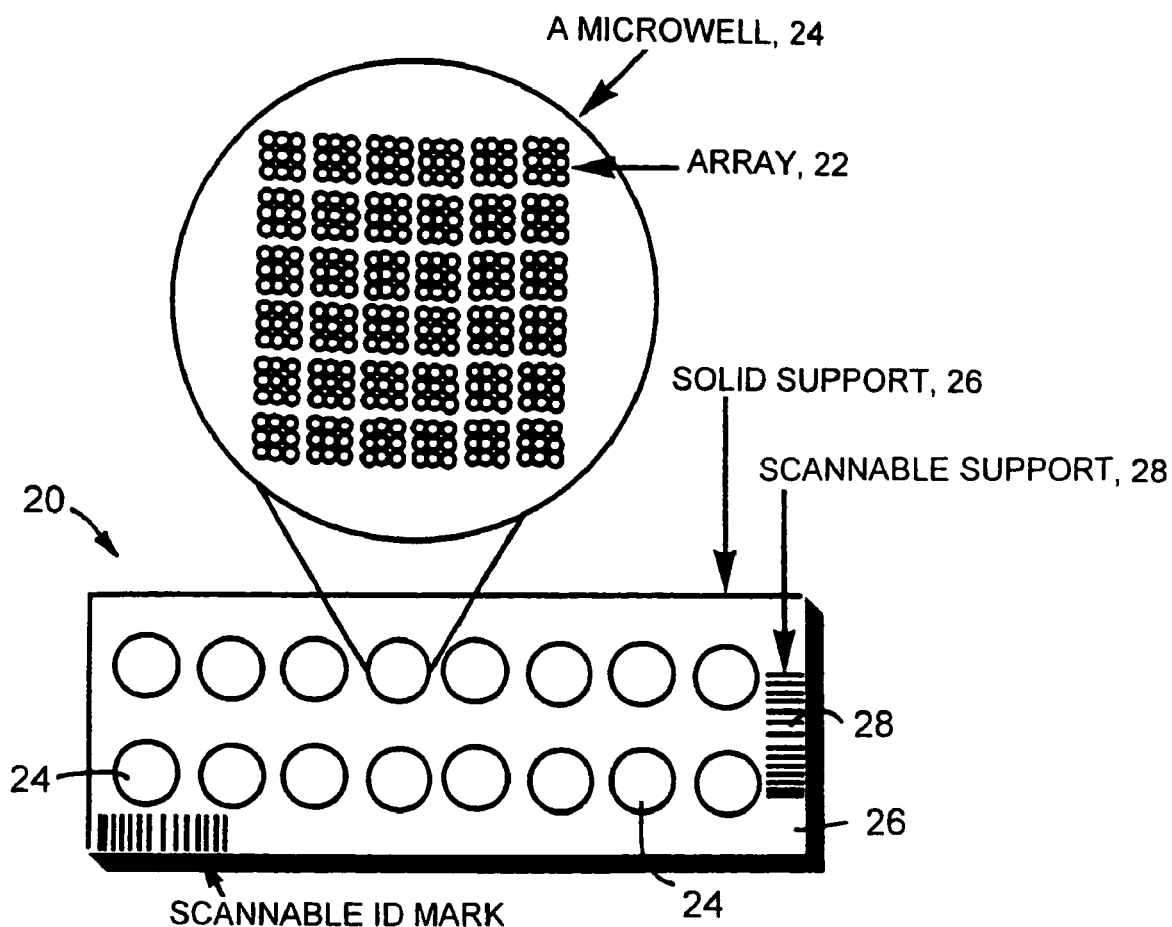
FIG. 1A is a schematic drawing of symptom-specific, clinically intelligent, diagnostic biochip device.

There is a need for a comprehensive diagnostic/screening assay where tests are clustered in clinically useful formats that enable the physician and/or a clinician to distinguish and discriminate between different etiologies based on a specific symptom or set of symptoms. In the new diagnostic devices or kits, tests are run in parallel, to avoid delays in disease diagnosis due to iterative and sequentially performed individual tests. The new devices can immensely simplify the differential diagnosis process.

General Methodology

The present invention provides methods for intelligently combining many tests into one test kit or device. The methods enable the clustering or multiplexing of tests (e.g., probes) specific to symptoms in a clinically intelligent manner to provide devices and assays for performing multiple tests in parallel for one or more specific clinical symptoms. The new devices include only those probes that can help to confirm or exclude a particular cause for an observed symptom (e.g., to help make an accurate diagnosis).

The format of the new multiplexed devices provides a new approach to diagnostic testing. The new devices detect analytes at the molecular level within a biological sample (such as, e.g., blood and blood-derivatives, cerebrospinal fluid (CSF), serum, urine or other bodily fluids, cell swabs, e.g., from the gums or inner cheek, and cell cultures) using an array having a plurality of probes to which the sample substance is applied. In one embodiment, the medical diagnostic device can employ microarray technology to cluster many probes onto a single biochip. However, the new devices and methods are not limited to biochips or microarrays. Other technologies can be used to create such devices. For example, a multiplexed device can be based on bead array technologies or microfluidic array technologies (from companies such as Luminex, Illumina, Aclara, and Caliper). As described herein, there are a number of ways of making multiplexed arrays.

The new methods enable the use of multiple probes that are all bound to a substrate using methods and conditions that keep the immobilized probe molecules biologically active. The multiplexed diagnostic devices also enable the simultaneous use of numerous disparate tests/probes under the same reaction conditions with high sensitivity and specificity.

Another feature of the new methods and devices is that numerous types of analytes, including nucleic acids and non-nucleic acid analytes can be simultaneously detected and/or quantitated on the same device. A number of naturally occurring or synthetic molecules recognize nucleic acids under physiological conditions. Examples of such molecules include polypeptide-based or polyamide probes such as transcription factors (e.g., such as zinc-finger proteins (ZFPs)), Helix-Turn-Helix motif proteins (e.g., GATA-1), immunoglobulin motif proteins (e.g., NFkB, NFAT), and polyamides, such as oligomeric heterocyclic minor groove binders (MGBs). Advantages of using polyamide molecules (such as ZFPs and MGBs) include: 1) they bind to double-stranded nucleic acids, and 2) they do so under almost the same conditions as proteins used to bind to other proteins and other molecules.

ZFPs are transcription factors in eukaryotes (e.g., in yeasts, plants, and mammals), which contain the Cis2His2 class of zinc finger domains, identified first in the DNA and RNA binding transcription factor TFIIIA, as their DNA-binding modules. This class of zinc finger motifs is unique in that their DNA binding specificities are highly adaptable; unlike most other DNA-binding domains, dozens of zinc finger domains characterized thus far bind to highly diverse DNA sequences, with each zinc finger domain able to recognize distinctive DNA binding sites. Each zinc finger module comprises only ~30 amino acids and folds into a [beta][beta][alpha] motif, stabilized by chelation of zinc between a pair of cysteines from the [beta]-sheet and a pair of histidines from the [alpha]-helix. The small globular structure often functions in nucleic acid binding and, particularly, in sequence-specific recognition of DNA, which is the key to function of transcription factors.

DNA binding zinc fingers related to those of the mouse transcription factor Zif268 employ such a simple mode of DNA recognition that they have become a useful paradigm in the understanding of protein-DNA interactions and have been used successfully as scaffolds in the design of DNA binding proteins with predetermined sequence specificity. The small size of the zinc finger limits individual modules to the recognition of only a few adjacent base pairs in duplex DNA, but allows multiple tandem modules to wind around the major groove of DNA, thus recognizing a longer run of bases. In the crystal structure of Zif268 fingers bound to DNA, three modules occupy the major groove of the DNA in series, each making base-specific contacts and typically overlapping three to four basepair subsites. Specificity arises from 1:1 interactions between residues of each zinc finger [alpha]-helix and the corresponding DNA bases. Zinc fingers have also been used to bind to DNA-RNA hybrids, RNA duplexes, and nucleic acids containing modified bases.

Simple covalent tandem repeats of the zinc finger domain allow for the recognition of longer asymmetric sequences of nucleic acids. Such adaptability of zinc finger domains in DNA/RNA recognition can be used to isolate or design novel proteins with altered DNA/RNA binding specificities, and to construct tailor-made nucleic acid binding proteins that specifically recognize almost any predetermined DNA/RNA sequence. For example, phage display technology can be used to create novel zinc finger proteins that bind diverse sequences with high affinity and specificity. Such novel or "designer" zinc finger proteins with desired nucleic acid binding specificities can serve as efficient probes for detecting nucleic acid sequences in a sample.

Similarly, MGB polyamides are a class of small synthetic molecules that bind in a sequence-specific manner in the minor groove of double-stranded DNA with extraordinary affinity and specificity. MGBs use a chemical recognition code that can distinguish each of the four Watson-Crick base pairs in the minor groove of DNA. Chemists have applied this binding code to design and synthesize a number of different such molecules that specifically recognize a given target sequence in the human genome. MGBs also bind their target nucleic acids under physiological conditions. Such novel or "designer" minor groove binding ligands with desired nucleic acid binding specificities can also be used as efficient probes for detecting nucleic acid sequences in a sample.

Transcription factors, such as ZFPs and small molecule polyamide ligands that recognize nucleic acids, such as MGBs, constitute a novel class of probes that recognize and detect nucleic acids under physiological conditions. Conditions used for bingeing such agents to their target nucleic acid sequences are similar to the ones used for detecting proteins and other non-nucleic acid components. Thus, these agents can be combined with protein and other biologic detecting agents onto a single support, such as a chip, for a unified screening device (e.g., UniScreen3). Such a device can detect DNA, RNA, proteins, glycoproteins, polysaccharides, other antigens simultaneously, on a single device (such as a biochip), and under the same conditions (See FIGS. 37A to C).

The specific biochemical environments required for binding of probe molecules currently limit multi-analyte biochip assays. For instance, proteins necessitate a stable pH and temperature to remain folded and retain optimal binding affinity for the target molecule. Conversely, DNA, PNA, and RNA require thermal cycling for hybridization of complementary strands to occur. This temperature variation would lower the binding capability of proteins and in most cases completely denature them. Therefore, the possibility of protein and nucleic acid probes binding target molecules in the same assay has been difficult before the development of the new methods described herein.

However, there are a number of naturally occurring and synthetic molecules that recognize nucleic acids by processes such as strand invasion. Strand invasion involves of a modified nucleic acid sequence that hybridizes with duplex DNA and is capable of removing a length of nucleic acid via free energy advantage. Single-stranded DNA, RNA, and peptide nucleic acid (PNA) molecules accomplish strand invasion under specific conditions. Chimeras of such molecules also result in a strand-invaded complex. In addition, Epoch Biosciences has created a class of synthetic probes called selective binding complementary oligonucleotides (SBCs) that consist of modified nucleotide bases that form hybrids with target duplex nucleic acids. A feature of SBCs is that the two strands do not form a stable duplex with each other, yet they form a very stable complex with the two strands of a target DNA. These molecules are usually used together, that is, the two complementary sequences are used to perform strand-invasion of DNA.

Hybridization of DNA or RNA targets to DNA/RNA probes attached to a biochip requires that the target be in single-stranded form. We have developed a methodology where a strand-invader, such as PNA, circular DNA/RNA, or one of two SBCs (an illustration is shown in FIG. 34B), can help separate the target duplex into a complex with single stranded target region. As shown in FIGS. 34A to E, this single-stranded target can easily bind to probes bound to a biochip without requiring a thermal denaturation step on the chip. A second, much smaller, oligo nucleotide can also be used in the mixture to drive the reaction to completion.

This method is relevant to biochip assays because a DNA probe missing an oligo-size portion of the duplex has extremely high binding affinity for any complementary nucleic acid sequence even under physiological conditions. (See, e.g., SBC Oligos, Epoch Biosciences, U.S. Pat. No. 5,912,340) and Zhang et al., Nucleic Acids Research, 28, 3332-38, 2000).

Although the new multiplexed diagnostic devices and kits have not been previously described, techniques for attaching individual probes to solid substrates are described in various publications such as, for example, U.S. Pat. No. 6,110,426; U.S. Pat. No. 5,763,158; U.S. Pat. No. 6,171,797; WO 00540046; U.S. Pat. No. 5,858,804; U.S. Pat. No. 5,252,743; U.S. Pat. No. 5,981,180; U.S. Pat. No. 6,083,763; WO 0004390; WO 00104389; WO 00104382; and other related publications.

The new devices/systems include many useful and advantageous features. For example, they can detect analytes under uniform temperature and pressure conditions, and can also have reactive sites/arrays that are either open or are enclosed in a chamber. These chambers can be flow-through or non flow-through. The devices/systems can also be entirely sealed once a sample has been introduced. In other embodiments, the new systems/devices combine sample collection modules with diagnostic devices into a unique combined module, which circumvents the need to transfer biological samples from collection tubes etc. to the diagnostic devices. Alternatively, the systems/devices include sample collection modules that are separate from diagnostic device modules and that can easily be connected at any stage, without having to take the sample out of the collection module.

The new multiplexed diagnostic systems enable a number of disparate tests to be performed simultaneously and under the same conditions, with low cross-reactivity and with high sensitivity and specificity. The devices/systems also provide a better dynamic range than currently available systems, and provide simple data interpretation as well as accurate diagnostic recommendations.

The new devices/systems also reduce the amount of biological sample needed. Individual tests as currently performed each require a certain amount of biological sample. As the number of tests goes up, the required amount of biological sample also goes up. The new multiplexed assay devices overcome such limitations in testing and sample requirements, because the sample size stays generally the same, even when new test probes are added to the system.

The new devices/systems also can be used with an "array of arrays" format, which provides a single device that can be used to process a large number of (same or different) samples in parallel, thus providing a high-throughput environment. For example, by introducing multiple sets of microarrays on a single biochip, one can screen multiple patient samples with clinically clustered tests in one step.

The new devices can be processed and analyzed using automated processing, such as robotic and computer-controlled screening, scanning, and delivery of results. The new devices, such as diagnostic biochips, can be processed using multiple dyes/colors. Assays can be performed either simultaneously or sequentially. Assays can use either single unique probes for each analyte or multiple unique probes for each analyte. Different types of assays, such as sandwich immunoassays, competition immunoassays, catalytic antibodies, hybridization, and single base extension, can be used in the new methods.

The new methods and systems also provide for image storage and processing, and manipulating stored signals to form a new image. Such methods can provide test results in formats that are easy to read and interpret. The new methods also include placing optical positioning markers for automated image processing and read-out. For example, such a method can include a row of dilution series for dynamic range determination and internal calibration on each biochip/microarray. The new methods generally provide excellent assay results by improving as well as optimizing currently used sample mixing conditions during the assay.

In some embodiments, the new methods include methods of delivering the results via communications networks such as the Internet, telephone systems, or wireless communication systems. Patients can be given a test ID number as well as a second unique identifier (such as a password) at the time of sample collection. When the results are ready, the patient can access the communications network (e.g., log in at a web site) and obtain comments from the attending physician as well as a clickable button to either download or erase the data after a specified time-period.

Figure 1B:
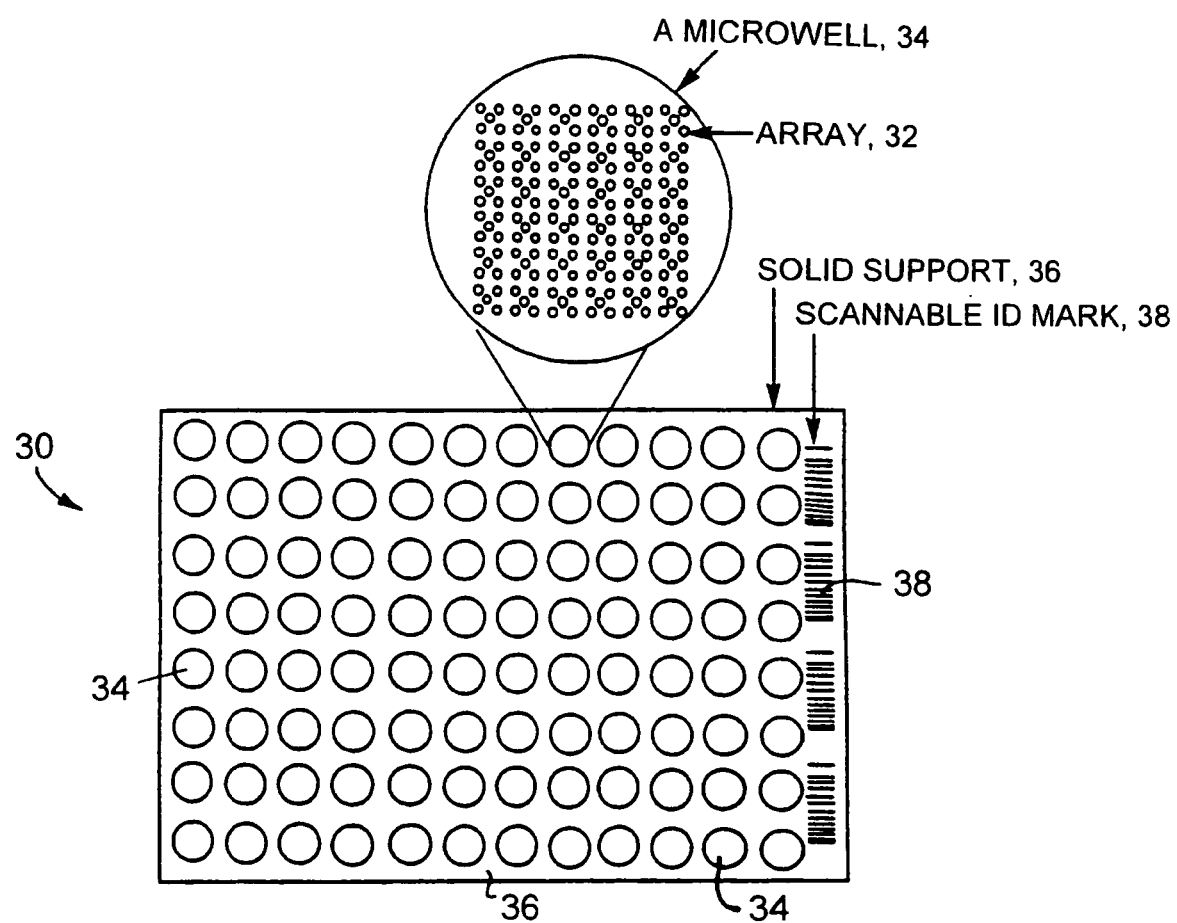
FIG. 1B is a schematic drawing of symptom-specific, diagnostic biochip device.
Figure 13A:
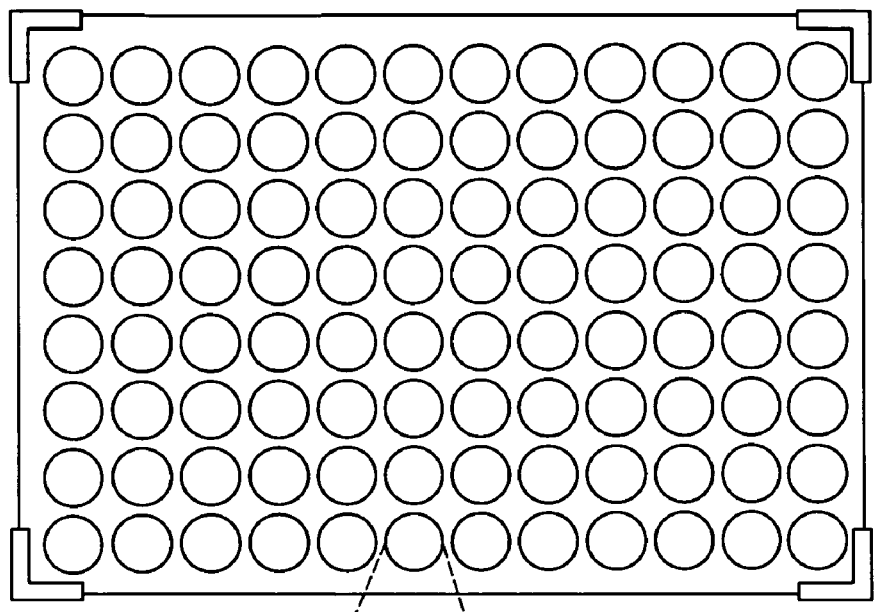
FIGS. 13A to 13C are schematic drawings of inverted array devices. Each elevated structure can have a number of probes attached in an array or an array of arrays format.
Figure 13B:
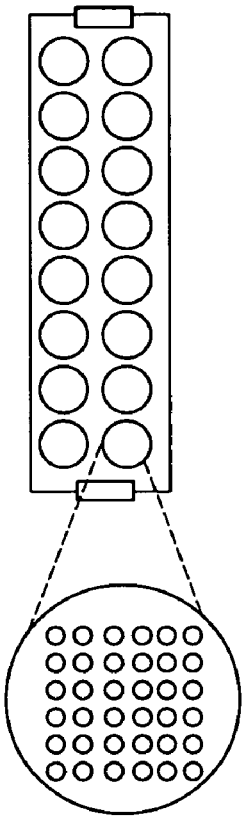
Figure 13C:
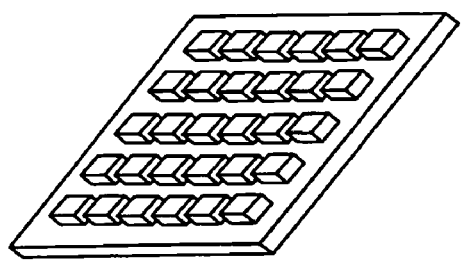

Methods of Preparing Clinically Intelligent, Symptom-Specific Diagnostic Devices The diagnostic devices are based on a variety of substrate-based technologies, such as solid plates, chips, or slides, as well as solid beads or microparticles. For example, the new devices can use microarray technology (see FIGS. 1A and 1B as an example). Glass or silicon microscope slides/chips can be used to prepare the devices (FIG. 1a). Alternatively, a larger membrane can be used to prepare up to 96 wells/sites per slide (FIG. 1b). A number of other materials, such as plastics, polymers, metals, and metal alloys can also be used as substrates. The device can have one or more sites per slides. FIGS. 13A to 13C, for example, show schematics of 96-site and 16-site inverted array device. All the glass slides can be coated with an organic or inorganic material to improve the surface properties as well as covalently attach the probes to the glass slides. If membranes are used as the substrate for the probes, they should not require pretreatment, but can be pretreated. A number of different targets are detected in a single assay by using one or more arrays of immobilized capture probes on the substrate (e.g., slide) surface. Methods of selecting and clustering the probes are described below. Such methods are used to determine which set of capture probes will be immobilized in a particular array. Coated glass slides can be purchased from commercial sources or can be prepared using standard techniques. The probes are then attached to the coated substrate using a variety of techniques. Standard binding techniques can be used, as well as novel probe attachment methods described below.

Selecting Targets for Specific Symptoms

For any given clinical symptom, there can be one, two, dozens, or possibly hundreds of causative agents or targets for the probes of the diagnostic device. A target can be one or more microbes such bacteria, viruses, mycoplasma, rickettsia, chlamydia, protozoa, plant cells (such as algae and pollens), or fungi. A target can also be a genetic disorder such as a single nucleotide polymorphism (SNP), a specific gene that is not normally present or expressed, or not present in multiple copies, or a mutation in a normally present gene. A target can also be a therapeutic optimization factor. For example, a target can be a specific microbial gene that renders a particular microbe susceptible or resistant to a particular drug. A target can also be a particular genetic sequence in a subject that makes the subject resistant, tolerant, or intolerant (allergic) to a particular drug. These types of targets can be used to develop a specific, tailored, and optimized therapeutic regimen. In addition, the targets can be selected to provide results that are most accepted by physicians and/or clinicians.

One goal of target selection is to select a number of targets (i.e., associated with possible causes of a specific symptom) that provides a high level of reliability that one of the selected targets is the cause of the symptom, and optionally to select additional targets that can be used to optimize therapy. In other words, the goal is to select targets that are the most likely to be the cause of the symptom. For example, if there are 50 possible targets that can cause a symptom, but only 10 targets are known to cause 90% of the clinically observed instances of a given symptom, then a diagnostic device might include probes (e.g., 10 or more probes) to detect only those 10 targets to provide a sufficient level of reliability. This device would not provide a positive result if the cause of the symptom in a subject happens to be one of the targets in the 10% not detected by the device. A more sophisticated diagnostic device might include an additional set of probes that are specific for 10 more known targets that together with the first 10 targets are known to cause 99% of the clinically observed instances of the symptom. Either device can include probes designed to optimize therapy. Of course, other scenarios are possible.

To provide a high degree of accuracy, several different probes can be used to detect and/or quantitate a single, specific target. For example, one probe can be designed to specifically bind to one epitope of an antibody target, and a second probe can be designed to specifically bind to a second epitope of the same antibody. In another example, one probe can be specific for an enzyme that is produced by a specific microbe, a second probe can be specific for a specific nucleic acid associated with that microbe, and a third probe can be specific for and antibody in a subject's bloodstream after exposure to the microbe. In addition, numerous probes of the same type can be clustered into separate locations or spots on a substrate to ensure that sample is evenly distributed over the entire array and that even low concentrations of target are detected. Two or more probes that recognize different epitopes of an antibody can also be mixed and placed on the same spot.

In each case, the probes are designed to specifically bind to an analyte that is, or is associated with, a target. For example, if the target is an antibody, the antibody is the analyte. If the target is a microbial gene, then a specific nucleic acid sequence can be the analyte. If the target is a genetic disorder in the subject, then the analyte might be a SNP or a specific mutant nucleic acid sequence.

Probe Selection

This section describes the different types of molecules that can be used as probes on different substrates, such as "chips." For any given target, there can be one or more types of probes that can be used to specifically bind to the target. For example, if the target is a nucleic acid molecule, e.g., from a subject's or microbe's DNA or RNA, the target can be detected using a nucleic acid probe or a protein-based, e.g., polyamide-based probe, such as a zinc-finger binding protein (ZFPs), or a minor groove binder (MGB). If the target is a particular antigen, the probe can be an antibody that specifically binds to that antigen. If the target is an antibody, the probe can be an anti-idiotype antibody, or the antigen to which the target antibody is known to bind.

Substrates can be linked to probes that will detect only nucleic acid targets (NuScreen3 Chip), only non-nucleic acid (e.g., protein-based or polypeptide-based and other types of targets such as haptens and chemicals) targets (ProScreen3 Chips), or both nucleic acid and protein-based targets (UniScreen3 Chips).

NuScreen3 Chips: These chips are used for analyzing nucleic acid components of a sample. They can analyze DNA, RNA, or both, and do so in their single-stranded or double-stranded form. Probes can be XNA based (DNA, RNA, PNA, LNA, HNA, etc.) or protein and polypeptide based (transcription factors, such as ZFPs, and small molecules, such as MGBs), or a combination of both. XNA probes usually bind to single-stranded nucleic acids, except for triplex forming oligos that bind duplexes. Thus, an optional denaturation step can be involved. Preferred probes are based on DNA oligonucleotides 16-40 bases long. ZFPs and MGBs recognize nucleic acids in their double-stranded form and thus require no denaturation step. Target nucleic acids from the sample can be pre-amplified prior to detection on the NuScreen3 Chip. The target nucleic acids can also be labeled with a detectable moiety during the amplification step. Amplification can be done using conventional techniques such as PCR, Reverse Transcription—Polymerase Chain Reaction (RT- PCR), in vitro transcription (IVT), Nucleic Acid Sequence Based Amplification (NASDA), Rolling Circle Amplification (RCT) etc.

ProScreen3 Chips: These chips are used for analyzing all other components of a mixture that the NuScreen3 chip cannot detect. Thus, ProScreen3 chips are used to detect, e.g., proteins, polypeptides, peptides, glycoproteins, antigens, haptens, or small organic molecules. Probes can be protein, peptide based or cell-based (such as cells expressing specific antibodies), but can also be, for example, glycoproteins, antigens, haptens, small organic molecules, nucleic acid molecules, and aptamers.

UniScreen3 Chips: These chips are universal screening devices, which means that they can detect almost any kind of target, be it a specific nucleic acid sequence or a protein or something else, with very high specificity and selectivity. The probes used for detection of all analytes other than nucleic acids are similar to the ones used in ProScreen3 chip. However, protein and peptide-based nucleic acid probes can be used for detecting nucleic acids, such as DNA and RNA, in the sample. An advantage of protein-based probes, such as ZFP and MGB probes, is that they recognize a specific nucleic acid sequence under physiological conditions, without any requirements to denature the nucleic acids. Thus, they can be combined with probes that are used to detect targets other than nucleic acids and be effectively used under the same binding conditions.

This invention utilizes the well-known sequence specific recognition properties of certain protein and peptide molecules that bind to nucleic acids selectively. The specific binding reaction does not require denaturation of the target nucleic acids and occurs under normal physiological conditions. Specifically, target nucleic acid molecules do not need to be denatured to a single-stranded form. ZFPs recognize DNA, RNA, and DNA-RNA duplexes. Binding takes place under physiological reaction conditions and is specific for each ZFP-nucleic acid sequence pair. Single base changes can easily be probed with this methodology, as the binding affinity of ZFP is greatly diminished for nucleic acids with even one base different than the target sequence of the ZFP molecule. This difference in binding is especially pronounced if the different base is recognized by the middle finger of a multiple finger (e.g., three-finger) protein molecule.

Thus, for the first time, the new methods enable the simultaneous detection of almost any combination of analytes on the same surface and using the same device, independent of the nature of the analyte. The device that performs such a function is the UniScreen3 Chip. In one embodiment, biotinylated DNA/RNA target (labeled during PCR/IVT steps) can be used. Labeled nucleic acid targets are captured by ZFPs and detected using anti-biotin antibodies coupled to streptavidin/HRP. In addition, Tyramide Signal Amplification/Rolling Circle Amplification Technology (TAS/RCAT) can be used for further signal amplification. Gold on silver staining methods (similar to immunohistochemical staining techniques) can also be used.

Substrate Selection and Methods of Attaching Probes

This section describes the different types of substrates (e.g., glass slides) and surfaces that can be used to create diagnostic devices, and provides examples of different immobilization methods that can be used to attach probes to these substrates.

In one embodiment, glass slides are used to prepare biochips. The substrates (such as films or membranes) can also be made of silica, silicon, plastic, metal, metal-alloy, anopore, polymeric, and nylon. The surfaces of substrates can be treated with a layer of chemicals prior to attaching probes to enhance the binding or to inhibit non-specific binding during use. For example, glass slides can be coated with self-assembled monolayer (SAM) coatings, such as coatings of as aminoalkyl silanes, or of polymeric materials, such as acrylamide and proteins. A variety of commercially available slides can be used. Some examples of such slides include 3D-link® (Surmodics), EZ-Rays® (Mosaic Technologies), Fastslides® (Schleicher and Schuell), Superaldehyde®, and Superamine® (CEL Technologies).

Probes can be attached covalently to the solid surface of the substrate (but non-covalent attachment methods can also be used). In one embodiment, similar substrate, coating, and attachment chemistries are used for all three—UniScreen3, ProScreen3, NuScreen3—devices. In another embodiment, different chemistries are applied.

A number of different chemical surface modifiers can be added to substrates to attach the probes to the substrates. Examples of chemical surface modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines (e.g., for native chemical ligation methods of Muir et al., *Proc. Natl. Acad. Sci. USA*, Vol. 95, pp. 6705-6710, June 1998), disulfide groups, alkyl and acyl halide groups, glutathiones, maltoses, azides, phosphates, and phosphines. Glass slides with such chemically modified surfaces are commercially available for a number of modifications. They can easily be prepared for the rest, using standard methods (Microarray Biochip Technologies, Mark Schena, Editor, March 2000, Biotechniques Books).

In one embodiment, substrate surfaces reactive towards amines are used. An advantage of this reaction is that it is fast, with no toxic by-products. Examples of such surfaces include NHS-esters, aldehyde, epoxide, acyl halide, and thio-ester. Most proteins, peptides, glycopeptides, etc. have free amine groups, which will react with such surfaces to link them covalently to these surfaces. Nucleic acid probes with internal or terminal amine groups can also be synthesized, and are commercially available (e.g., from IDT or Operon). Thus, nucleic acids can be bound (e.g., covalently or non-covalently) to surfaces using similar chemistries.

The substrate surfaces need not be reactive towards amines, but many substrate surfaces can be easily converted into amine-reactive substrates with coatings. Examples of coatings include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), and BSA coatings (which can be reacted with bis-NHS cross-linkers, maleimide-NHS cross-linkers, etc.). Alternatively, the probes, rather than the substrate, can be reacted with specific chemical modifiers to make them reactive to the respective surfaces.

A number of other multi-functional cross-linking agents can be used to convert the chemical reactivity of one kind of surface to another. These groups can be bifunctional, tri-functional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS-Y-NHS, is a homo-bi-functional cross-linker and would connect an amine surface with an amine-group containing molecule. If X is NHS-ester and Z is a maleimide group, the resulting cross-linker, NHS-Y-maleimide, is a hetero-bi-functional cross-linker and would link an amine surface (or a thiol surface) with a thio-group (or amino-group) containing probe. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc. Such cross-linkers can be reacted with the surface or with the probes or with both, in order to conjugate a probe to a surface.

Other alternatives include thiol reactive surfaces such as acrydite, maleimide, acyl halide and thio-ester surfaces. Such surfaces can covalently link proteins, peptides, glycopeptides, etc., via a (usually present) thiol group. Nucleic acid probes containing pendant thiol-groups can also be easily synthesized.

Alternatively, one can modify glass surfaces with molecules such as polyethylene glycol (PEG). A novel approach to creating such modified surfaces is to use PEGs of mixed lengths (see, e.g., FIGS. 4A and 4B and 6A to 6C). Exposed ends of PEGs can be activated with bifunctional cross-linkers as mentioned above. As shown in FIG. 4B, the varied lengths of PEG linkers create a three-dimensional, rather than a flat, two-dimensional binding environment (FIG. 4A), which provide higher probe attachment densities because of better packing of the biological molecules upon attachment. Packing of biomolecules, such as proteins, would be higher on a slightly three-dimensional or uneven binding surface than on a completely even and flat binding surface.

Yet another alternative is to create a three-dimensional, covalently linked mesh of streptavidin or other linker molecule (see FIGS. 5A to 6C). For example, piranha-treated glass is first coated with a terminal amine containing silylating agents (e.g., N-(3-acryloxy-2-hydroxypropyl)-3-aminopropyltriethoxysilane, acryloxytrimethylsilane, triethoxy methyl silane, and aminopropyl triethoxy silane). After a baking step, activated streptavidin (other proteins such as avidin can also be used) is applied to the surface of a blank slide (activation is done using bifunctional cross-linking groups) (FIG. 5A). This creates a three-dimensional mesh on the glass surface. The streptavidin molecules are linked not only to the glass surface, but are also cross-linked with each other (FIG. 5C) to create an ordered array. Absent cross-linking, the array is typically dis-ordered (FIG. 5B). The cross-linking density can be controlled by the relative concentrations of streptavidin and the cross-linkers (NHS-activators, bis-biotin, etc.). After coating with streptavidin, excess NHS-esters can be quenched with glycine (or other reagents such as ethanolamine, tricine, etc.) or with a layer of BSA, milk-protein, or a number of other such biochemical reagents to reduce non-specific binding. The addition of multi-functional cross-linkers, such as NHS-biotin or maleimide-biotin, to this surface regenerates active groups ready for covalently linking (amine- or thio-group containing) probes. The resulting surface is much more reactive with proteins and other probe molecules (FIG. 5C).

FIGS. 6A to 6C are similar to FIGS. 5A to 5C, but in this example, probes of mixed lengths are used, as also shown in FIG. 4A. The varied length probes (and/or cross-linkers) provide an uneven binding environment that can provide higher probe attachment densities because of better packing of the biological molecules upon attachment.

Many other surface modification alternatives (such as photo-crosslinkable surfaces and thermally cross-linkable surfaces) are known to those skilled in the art. Some technologies are commercially available, such as those from Mosiac Technologies (Waltham, Mass.), Exiqon3 (Vedbaek, Denmark), Schleicher and Schuell (Keene, N.H.), Surmodics3 (St. Paul, Minn.), Xenopore3 (Hawthorne, N.J.), Pamgene (Netherlands), Eppendorf (Germany), Prolinx (Bothell, Wash.), Spectral Genomics (Houston, Tex.), and Combimatrix3 (Bothell, Wash.).

Surfaces other than glass are also suitable for such devices. For example, metallic surfaces, such as gold, silicon, copper, titanium, and aluminum, metal oxides, such as silicon oxide, titanium oxide, and iron oxide, and plastics, such as polystyrene, and polyethylene, zeolites, and other materials can also be used. The devices can also be prepared on LED (Light Emitting Diode) and OLED (Organic Light Emitting Diode) surfaces. An array of LEDs or OLEDs can be used at the base of a probe array. An advantage of such systems is that they provide easy optoelectronic means of result readout. In some cases, the results can be read-out using a naked eye.

Probes can be deposited onto the substrates, e.g., onto a modified surface, using either contact-mode printing methods using solid pins, quill-pins, ink-jet systems, ring-and-pin systems, etc. (see, e.g., U.S. Pat. Nos. 6,083,763 and 6,110,426) or non-contact printing methods (using piezoelectric, bubble-jet, syringe, electro-kinetic, mechanical, or acoustic methods. Devices to deposit and distribute probes onto substrate surfaces are produced by, e.g., Packard Instruments. There are many other methods known in the art. Preferred devices for depositing, e.g., spotting, probes onto substrates include solid pins or quill pins (Telechem/Biorobotics). Each probe can be deposited in one or more replicates to achieve better results. Probes can also be deposited in such a geometric pattern that the read-out can be easily converted to a result by simple visual inspection (see FIGS. 1-3). For example, probes can be deposited in a square pattern of nine spots (FIG. 1A), an "X" pattern of five spots (e.g., FIGS. 1B and 3A), a "V" or "A" pattern of three spots (FIG. 2B), or a "+" of five spots (FIG. 2C).

Fine-Tuning ("Developing") Devices

After the probes are deposited, the devices/slides/supports are developed using standard techniques according to surface modification and probe attachment chemistries used. For example, NHS-ester activated slides, that have amine-group containing probes attached, can be developed by incubated in a humidity chamber (preferably 75%-80%) and at 4° Celsius for 2-16 hours. The developed slides, in a preferred embodiment, can be kept sealed in an aqueous buffer until the time of their use. The aqueous buffer can also contain Bovine Serum Albumin (BSA), milk proteins, glycerol, trehalose or other such reagents that preserve the activity of attached probes. In other embodiments, the slides can be kept in a dry, cool, and dark environment.

Some commonly used blockers are as follows:

1. BSA, e.g., combined with other blockers and surfactants.

2. Casein, a milk-based protein containing indigenous biotin (however, it should be avoided when working with systems involving biotin to prevent interference).

3. Pepticase3 (Casein Enzymatic Hydrolysate): an enzymatic derivative of casein.

4. Non-Ionic Surfactants: Tween 20® and Triton X-100® are typical. When used in combination with another blocker, a common ratio is 1% Blocker:0.05% Surfactant.

5. "Irrelevant" IgG.

6. FSG (Fish Skin Gelatin), pure gelatin or gelatin hydrolysate can also be used.

7. Polyethylene Glycol, a versatile blocker, available in a number of sizes, configurations, and charges can also be used.

8. Sera and non-cross reacting serums, such as horse or fish serum, are very inert.

9. Polysaccharides and glycoproteins.

10. Commercial Blockers, composites of two or more single blocking substances of various molecular weights, can also be used effectively over a wide range of conditions.

An alternative blocking methodology is carried out as follows. After the probes are spotted on the solid surface, the rest of the chip surface can be deactivated by irradiating with electromagnetic radiation. This step can be performed after the blocking steps noted above, to denature the blocking agents. This step will reduce the antigenic properties of the surface agents and will result in lower non-specific binding of target molecules during an assay.

Devices

As shown in FIG. 1A, a diagnostic biochip device 20 can contain more than one array 22, in a multi-reaction site (e.g., multispot or multiwell) format, such as sixteen reaction sites 24, such as microwells, on a solid support 26, such as a slide. In the case of a multiwell device, each microwell 24 can contain probes in an array 22 or an "array of arrays" format. Probes can be deposited in an easy to read geometrical pattern (here, a square of nine spots). Each microwell is delimited in that it has partitioned zones. The partitioning can be achieved by chemical treatment or by application of a mask, preferably hydrophobic, onto the surface of the slide, either prior to, or after probe deposition steps. The partitioning can result in the creation of cylindrical microwells that have a higher sample retaining capacity, compared to supports without wells. Each solid support 26 can include scannable markings 28 (such as a bar code) for computer-controlled, automated processing.

FIG. 1B illustrates a diagnostic biochip device 30 with ninety-six reaction sites 34, such as microwells on a solid support 36, such as a membranous slide. Each microwell 34 can contain probes in an array 32 or an "array of arrays" format. Probes can be deposited in an easy to read geometrical pattern (here, an "X" of five spots). Solid support 36 includes scannable markings 38 for computer-controlled, automated processing. Such markings can be anywhere on the support, including on the sides or back of the support. These markings allow the support/slide to be read/scanned using conventional scanning devices, such as laser scanners.

Figure 2A:
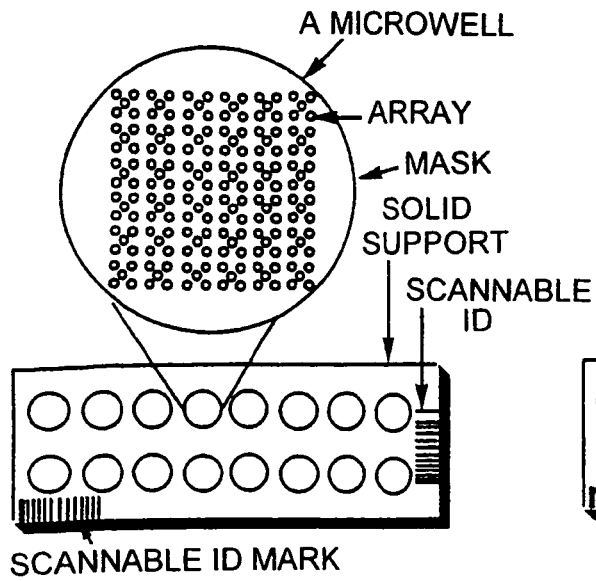
FIGS. 2A to 2C are schematic drawings of three symptom-specific, diagnostic biochip devices, each having a different configuration of probes in "arrays of arrays" format. For example.
Figure 2B:
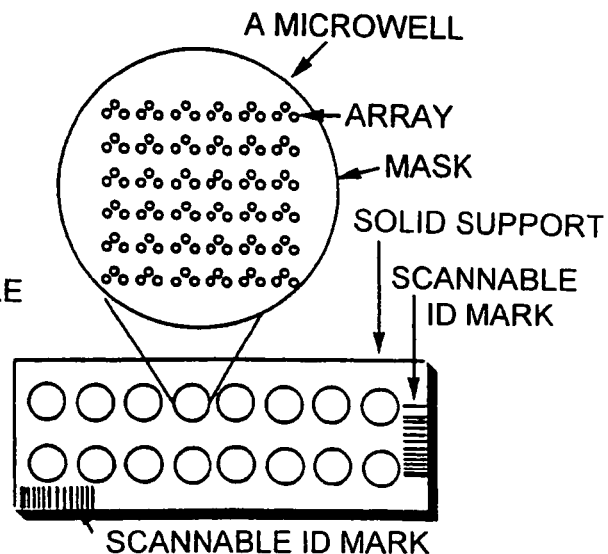
Figure 2C:
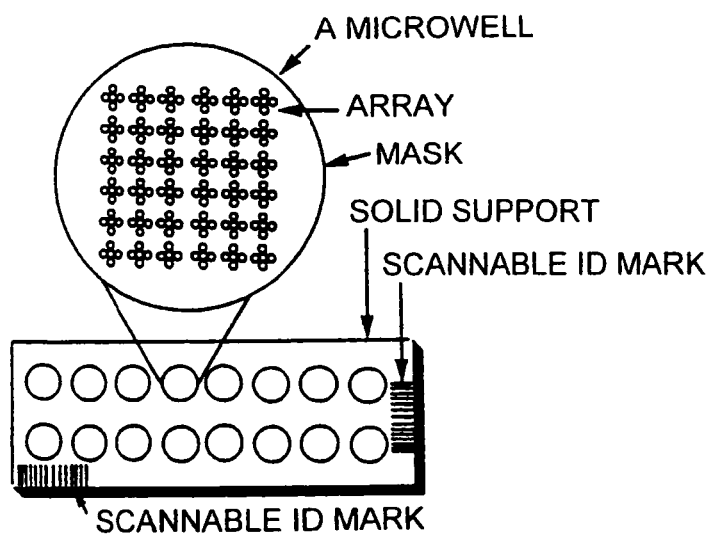

FIGS. 2A to 2C illustrate additional probe array configurations. FIG. 2A shows probes in an "X" configuration. FIG. 2B shows a "V" or "A" configuration, and FIG. 2C shows a "+" configuration.

FIGS. 3A to 3C, show another diagnostic biochip device 40 that contains more than one array 42, in a multi-reaction site (e.g., multiwell) format, such as sixteen reaction sites 44, such as microwells, on a solid support 46, such as a slide. Each microwell 44 can contain probes in an array 42 or an "array of arrays" format. Probes are deposited in a geometrical pattern (here, an "X" of five spots). Each microwell 44 is delimited in that it has partitioned zones. Here, partitioning is achieved by applying a mask 43, preferably of a hydrophobic material, onto the surface of the solid support 46, either prior to, or after probe deposition steps. The partitioning creates cylindrical microwells that have a higher sample retaining capacity, compared to supports without wells. The mask 43 can be applied to the support 46 on top of an intermediate organic layer 45 as shown in the cross-section of FIG. 3B. FIG. 3C shows a three-dimensional view of a single microwell 44.

Each solid support 46 can include a scannable ID marking 48 for computer-controlled, automated processing. Here there are two sets of markings 48, to allow easier access for scanning, or to provide different information on each marking.

One problem with biochip devices is the formation of bubbles during sample application step. An advantage of the cylindrical shape of the wells is that it has fewer problems with bubbles due to curved walls of the microwell. A rectangular shape creates sharp corners, which usually retain air-bubbles. A cylindrical shape does not have that problem.

Mixing Apparatus for Use in Microarrays and Biochips

Figures 8A, 8B:
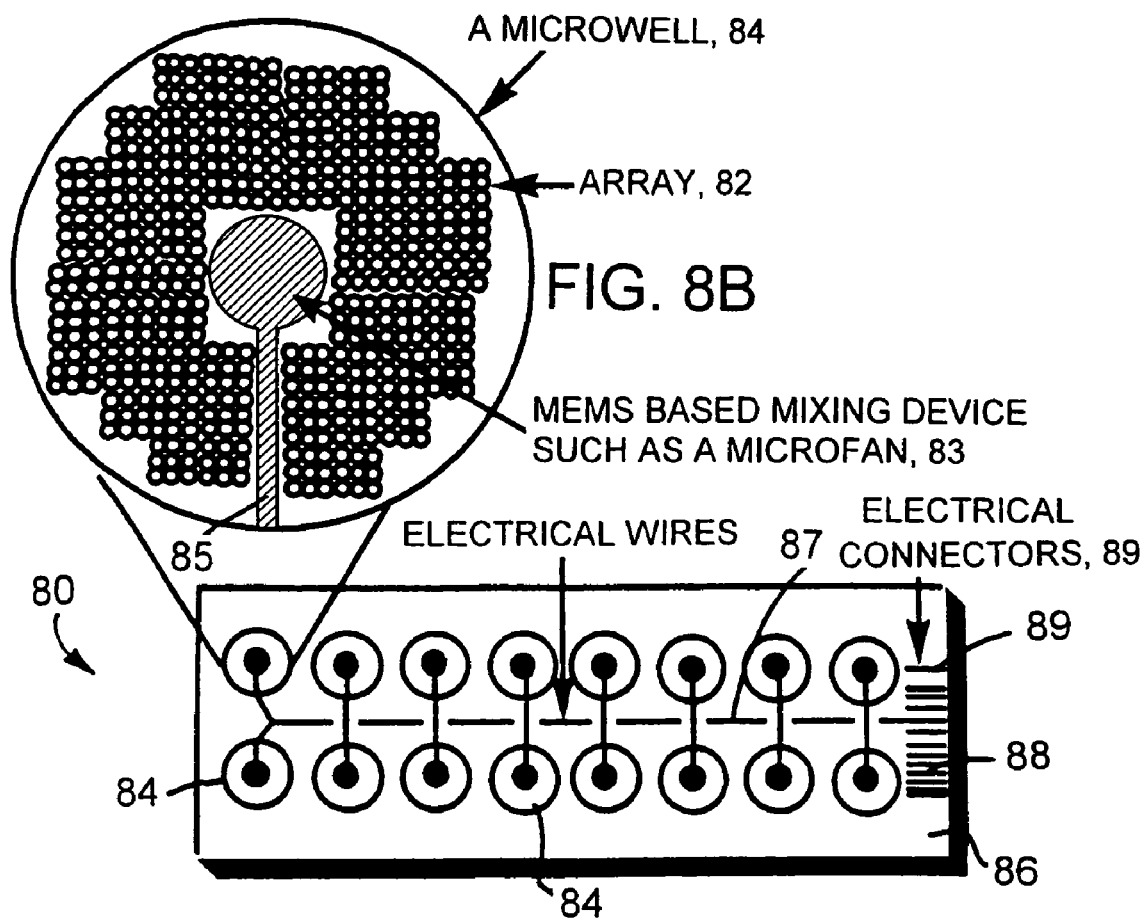
FIGS. 8A and 8B are an alternative version of the mixing system of FIGS. 7A and 7B.

Mixing of samples during incubation is important in microarray assays. Binding efficiency of different target analytes to their respective probes is directly linked to their concentration as well as their rate of diffusion. Mixing a sample during incubation helps increase the rate of diffusion thus giving better and more reproducible results. The binding time can also be decreased if efficient means of mixing can be achieved. FIGS. 7A and 7B as well as FIGS. 8A and 8B illustrate solid supports that include micromixers powered by micromotors (such as micro-fans and biological motors). These micromotors can be, for example, electric, magnetic, optoelectronic, or biochemical motors. Mixing can also be achieved by incorporating magnetic beads (such as Dyna-Beads®) in the sample and using a stirrer underneath the biochip to stir each well.

FIG. 7A shows a solid support 76 with sixteen microwells 74. Each microwell 74 is outfitted with a micromotor 73 including microfan blades 75. FIG. 7B shows an enlarged view of a single microwell 74 and one way of attaching the motor to the slide and depositing probe arrays around this motor in four quadrants. Other probe array configurations are possible. Electricity is conveyed by wires 77 that run from one or more electrical connectors 79, e.g., at one end of slide 76, to each micromotor 73. Electricity can also be conveyed by metal or other conductors deposited onto or into the solid support, e.g., using standard printed circuit technology. New miniaturization techniques allow the entire micromotor to be deposited onto the solid support in a similar manner. Slide 76 can include computer-readable markings 78 as described above.

FIG. 8A illustrates a solid support 86 with sixteen microwells 84. Each microwell 44 is outfitted with a micromotor 83 including a microfan blade 85. FIG. 8B shows an enlarged view of a single microwell 84 and a way of depositing probe arrays around this motor in a circle. Electricity is conveyed by wires 87 that run from one or more electrical connectors 89, e.g., at one end of slide 86, to each micromotor 83. As above, electricity can also be conveyed by metal or other conductors deposited onto or into the solid support, e.g., using standard printed circuit technology. New miniaturization techniques allow the entire micromotor to be deposited onto the solid support in a similar manner. Slide 86 can include computer-readable markings 88 as described above.

In all of these embodiments, electric motors can be powered using electromagnetic sources such as electronic and photonic means. Some motors can have optically activatable switches that can be switched on using light. Molecules that can be induced to rotate between two geometric shapes, such as cis- and trans-stilbene that undergo stereo conversion from one to another configuration upon electromagnetic excitation, are one example of such motors. Biological motors, such as ATP synthase, can be powered by electromagnetic sources or by biological reactions. For example, ATP synthase can be attached to a bead (for example, see "Biological machines: from mills to molecules, *Nature Reviews Molecular Cell Biology* 1; 149-152, 2000), and its motor can be attached to another bead. The two beads will rotate with respect to each other, in the presence of molecules such as ATP, and in the process, mix the fluids.

A number of biological molecule based fluid micromixers are presented. For example, these micromixers can be based on ATPase (see, e.g., Soong et al.; *Science,* 290 (5496):1555-1560, 2000; Wang et al., *Nature,* 396:279-282, 1998; Montemagno et al., Nanoscale Biological Engineering and Transport Group, Cornell University, *Nanotechnology,* 10:225-231, 1999; (http://falcon.aben.cornell.edu.). Micromixers can also be based on kinesin, kinesin Related Proteins, myosin, DNA Helicase, and DNA Sliding clamps (see, e.g., Bertram et al., *Journal of Biological Chemistry,* 275(37): 28413-28420, 2000; O'Donnell et al., *Journal of Biological Chemistry,* 270(22):13358-13365, 1995; Hingorani et al., *The EMBO Journal,* 18(18):5131-5144, 1999); nucleic acid based rotaxanes and Pseudo-rotaxanes (Ryan et al., Chemistry and Biology, 1998); circular triplex forming oligonucleotide (CTFO) and duplex DNA (Rehman et al., 1999); as well as chimeras and derivatives of such proteins and nucleic acids. FIGS. 24A to 33C illustrate how these can be manufactured and used.

An innovative molecular switch can also be designed for these micromixers. Novel synthetic analogs of nucleotide triphosphates, in conjunction with aminoacid modification in the binding site of the protein micromixers can be used for this purpose. For example, structure-based amino acid changes, as utilized in the studies of various kinases by Shokat and co-workers, can be applied to these proteins (See, Bishop et al., UNNATURAL LIGANDS FOR ENGINEERED PROTEINS: New Tools for Chemical Genetics, Annu. Rev. Biophys. Biomol. Struct., 29:577-606, 2000). Thus, operations of these micromixers can be tightly controlled using chemical means.

Some of these mixing devices can also be incorporated in the surfaces covering biochips, such as cover slips or hybridization chambers. An advantage of such a methodology would be that the mixing apparatus would be compatible with the currently available chip platforms.

Hybridization Chambers

One of the critical issues with current biochip assays is the high variability in results. One way of overcoming this issue is by performing the same assay on more than one array or on more than one biochip. This improves the confidence level of the output. A shortcoming of this approach is that there can still be small variations in the assay conditions, which may affect the results. A better approach would be to perform the assay in such a way that the reaction conditions are identical. The new systems can include a novel hybridization chamber that can perform assays on two chips simultaneously and under same reaction conditions. Two biochips are laid one on top of the other, with the reactive arrays facing each other and separated along the edges with a thin separator. The space left in the middle accommodates the sample, which contacts both of the slides simultaneously. The two slides and the separator may be enclosed in a chamber. Alternatively, a chamber with preformed side protrusions can be designed and two biochips can be inserted to make a reaction chamber. FIGS. 35A to E and FIGS. 36A to E illustrate some embodiments and all of the components of novel hybridization chambers. The interior chamber of these hybridization modules can be filled in a variety of ways, such as by using a pipetman, syringe, or needle.

Inverted Array Devices

New inverted array microarray devices are illustrated in FIGS. 9A to 12D. These new devices consist of one or more elevated structures or columns on a solid support or platform. A device can have one or more such structures and the structures can be of any geometric shape and form. The structures can also be vertically straight, angled, or twisted. The structures can be in the form of one or more arrays. Multiple probes are bound in an array (or an array of arrays) to the surface of the elevated structures. Thus, each elevated structure, denotes a (multiplexed) reaction site. The device can be used to perform reactions simultaneously or sequentially.

Any of the known substrates and chemistries can be used to create such a device. For example, glass, silica, silicon wafers, plastic, metals and metal alloys can all be used as the solid support. Elevated structures can be manufactured by a number of techniques known in the art, such as etching, machining, photolithography, and other microfabrication techniques. Similarly, probes can be attached to the surface of these devices using a number of different methods as described herein.

FIGS. 9A to 9C show one example of such an inverted array device 90. Device 90 can contain more than one array 92, in a multi-reaction site (e.g., multiwell) format, such as sixteen reaction sites 94, such as elevated circular structures, on a solid support 96, such as a slide. Each elevated structure 94 can contain probes in an array 92 or an "array of arrays" format. Probes can be deposited in an easy to read geometrical pattern (here, a square of nine spots). Each elevated structure is delimited in that it has partitioned zones. The partitioning is achieved here by application of a mask (or coating) 93, of a hydrophobic or hydrophilic material, onto the surface of slide 96, either prior to, or after probe deposition steps. The partitioning can result in the creation of cylindrical elevated support structures that have a higher sample retaining capacity, compared to supports without such structures. Each solid support 96 can include scannable markings 98 (such as a bar code) for computer-controlled, automated processing.

FIG. 9B shows device 90 from a cross-sectional side view. FIG. 9C shows two different configurations (cubic and cylindrical) of the elevated structure 94 on solid support 96 in three dimensions.

Figure 10A:
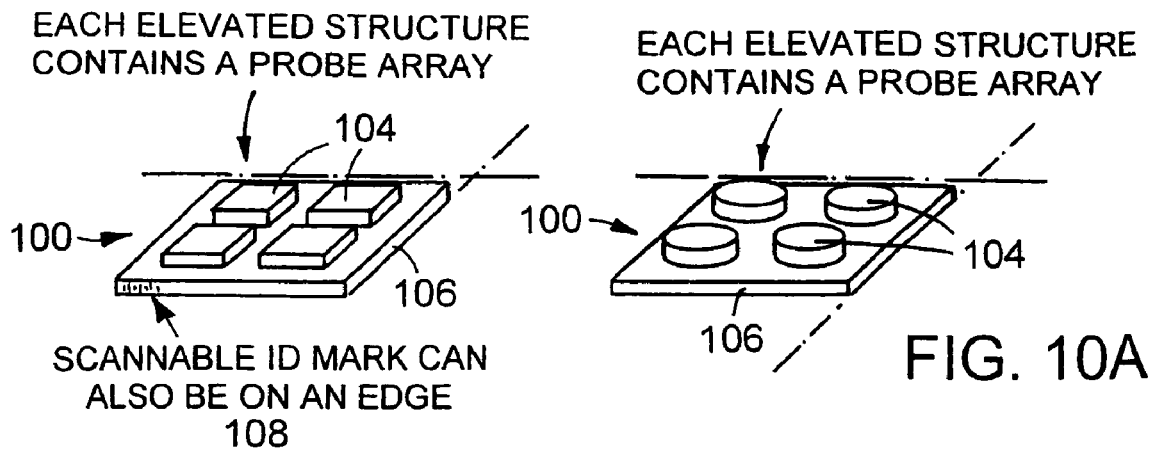
FIGS. 10A and 10B are a schematic drawings of pairs of new inverted array systems of multiwell symptom-specific, diagnostic biochip devices in the upright and inverted states, respectively.
Figure 10B:
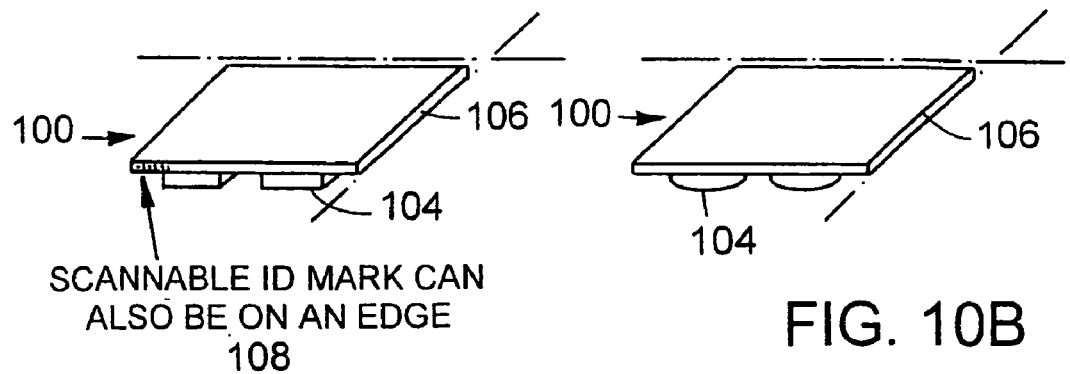

FIG. 10A shows two types of inverted array devices 100 in schematic form. Each device includes a solid support 106 and a plurality of elevated structures 104 (either cubic or cylindrical). The solid supports 106 can include scannable identification markings 108, such as bar codes or circular codes. FIG. 10B shows the same devices when inverted for use.

Figure 10C:
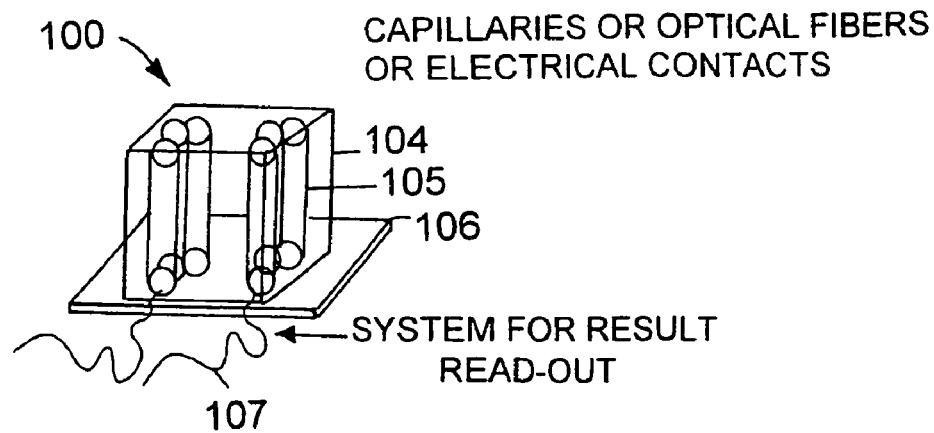
FIG. 10C is a diagram of an elevated structure array in which each structure includes an embedded capillary, electrical wire, or optical fiber to provide an electrical or optical readout.
Figures 12A, 12B, 12C, 12D:
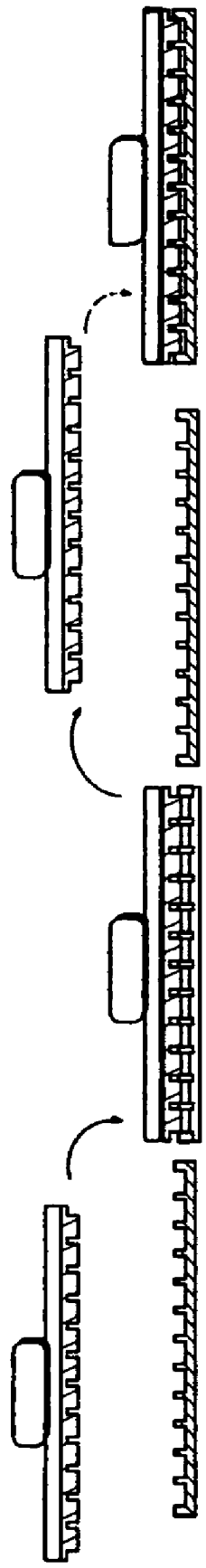
FIGS. 12A to 12D are a series of schematic drawings of the inverted array and microtiter plate system of FIG. 11.

FIG. 10C illustrates an embodiment in which each of the elevated structures 104 includes an embedded capillary fiber optic or electrical "tube" 105, which can simplify the assay and the read-out process. Each of these "tubes" 105 can have one or a set of related probes attached. Each tube, or set of tubes is connected (e.g., either electrically or optically) with wires or optic fibers 107 that carry a signal from the tubes through or along the solid support 106 and out of the device for result read-out.

For some applications, the inverted array devices are surrounded by a liquid barrier or wall, to contain sample fluids introduced onto the surface of the device. In other embodiments, assays are performed using the new inverted array devices by incubating the entire device on or within a chamber, such as a microtiter plate. In these cases, no sample delimiting structure or flow barrier is needed on the array device itself, because the sample is not placed or poured directly on the device, but is held in a separate microtiter plate, to which the device is applied. In one embodiment, the device can be lowered into a reaction vessel, such as microtiter plates, to perform assays.

FIGS. 11A to 11E illustrate how an inverted array device 110 is inverted and inserted into a microwell or microtiter plate 111. FIG. 11A shows a top view of inverted array device 110 with 96 elevated structures 114 on a solid support 116 having scannable markings 118. FIG. 11B shows a side view of device 110. FIG. 11C shows a top view of a microtiter plate 111 with microwells 113. In use, the inverted array device 110 is inverted and placed onto the microtiter plate 111 to insert each elevated structure 114 into an individual microwell 113. Each microwell contains one sample, and each microwell can contain the same or a different sample. Sets of 2, 3, 4, 5, 10, or more microwells can also contain the same sample.

FIGS. 13A to 13C illustrate another embodiment of the inverted array devices. The devices can have edge features that help with the alignment or positioning of these devices with the microwell plates. These edge features can also help with the use of these devices by automated instruments.

Figure 14A:
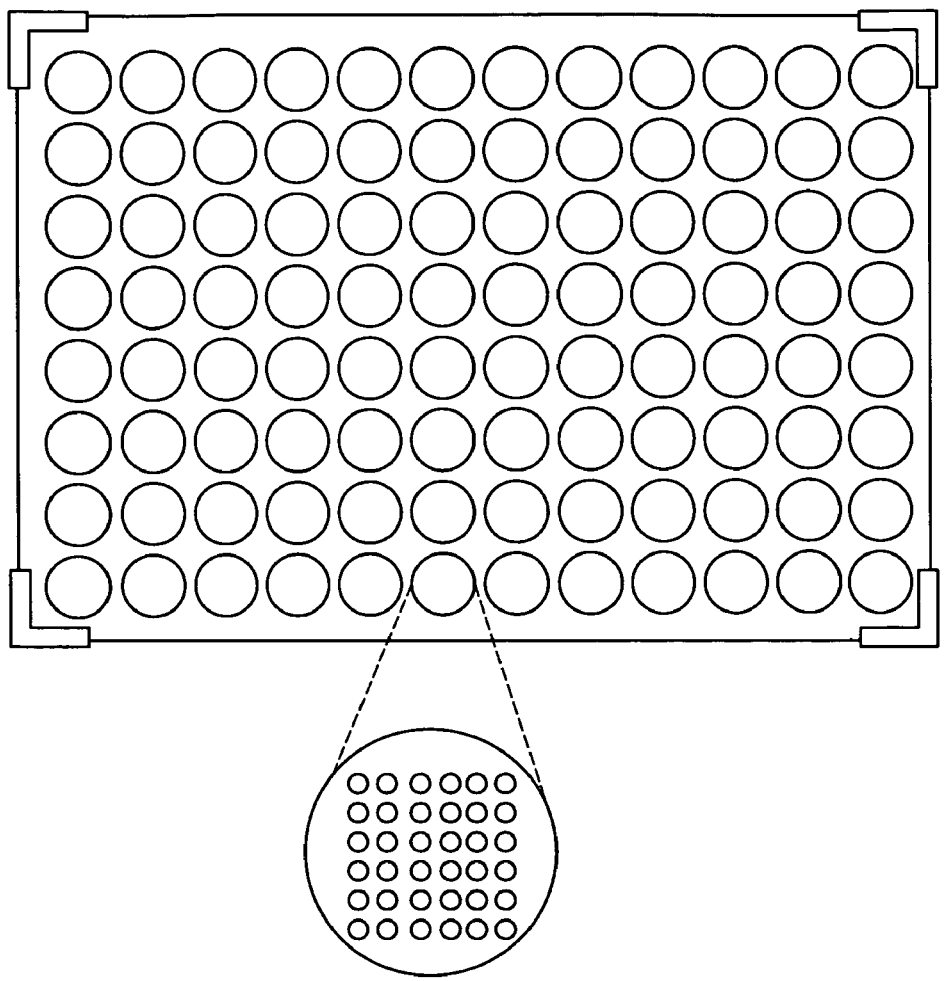
FIGS. 14A to 14D are schematic drawings of inverted array devices.
Figure 14B:
Figure 14C:
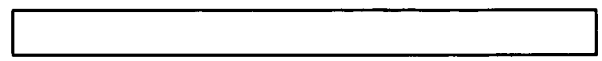
Figure 14D:
Figure 17:
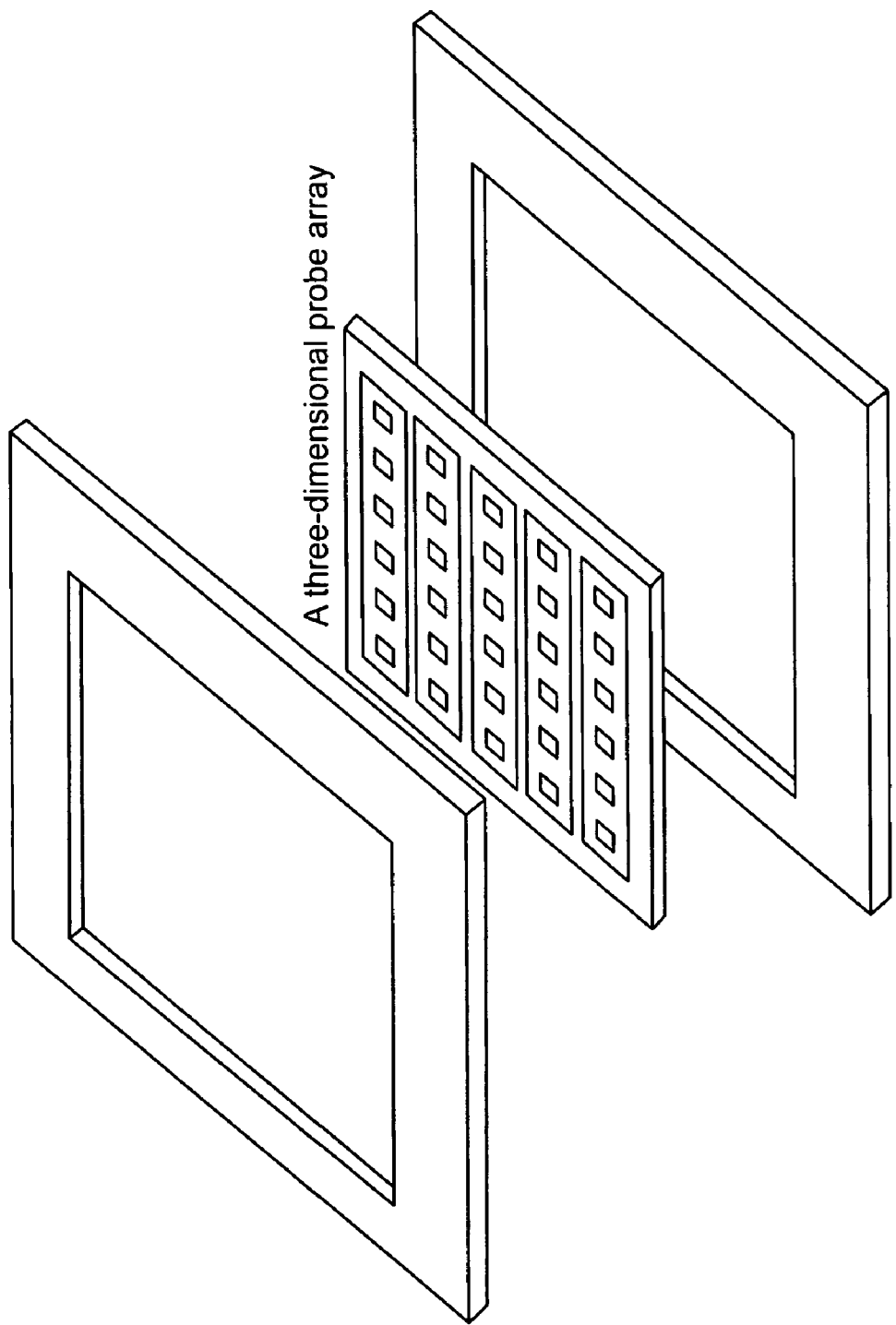
FIG. 17 is a schematic diagram of a three-dimensional porous array placed inside of a cartridge-type device.
Figure 18B:
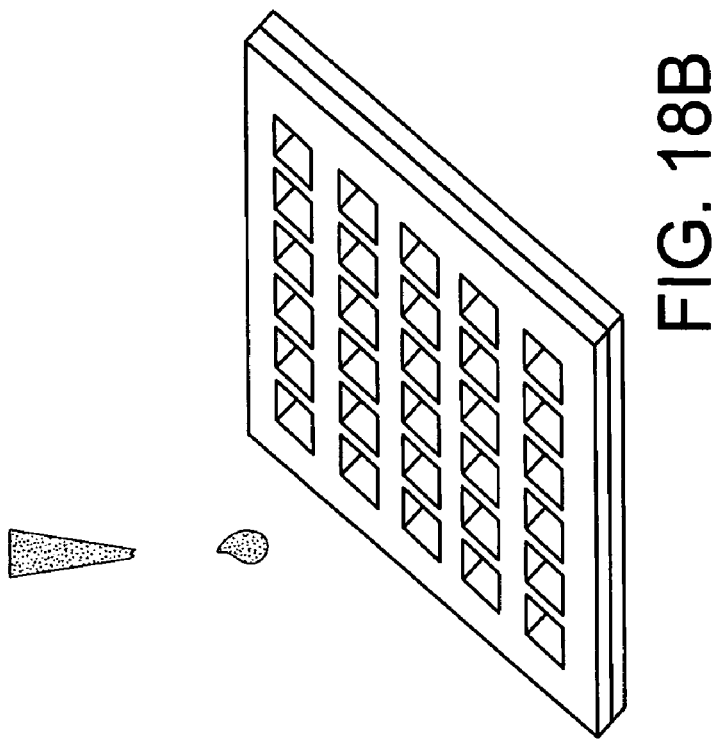
FIGS. 18A and B and 19A to E are diagrams of another three-dimensional porous array. Such a three-dimensional porous array can be manufactured in a number of ways and these figures illustrate one method.
Figure 18A:
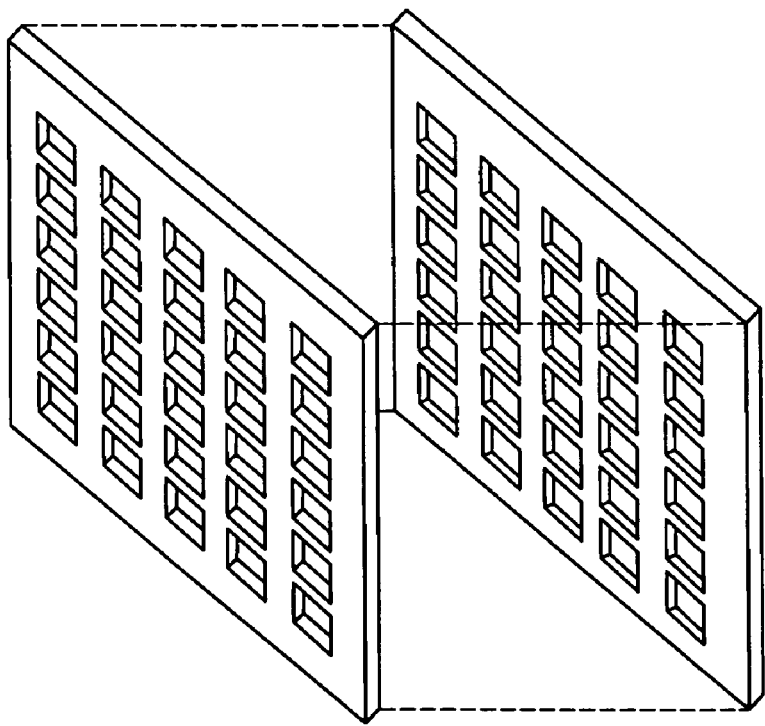
Figure 19A:
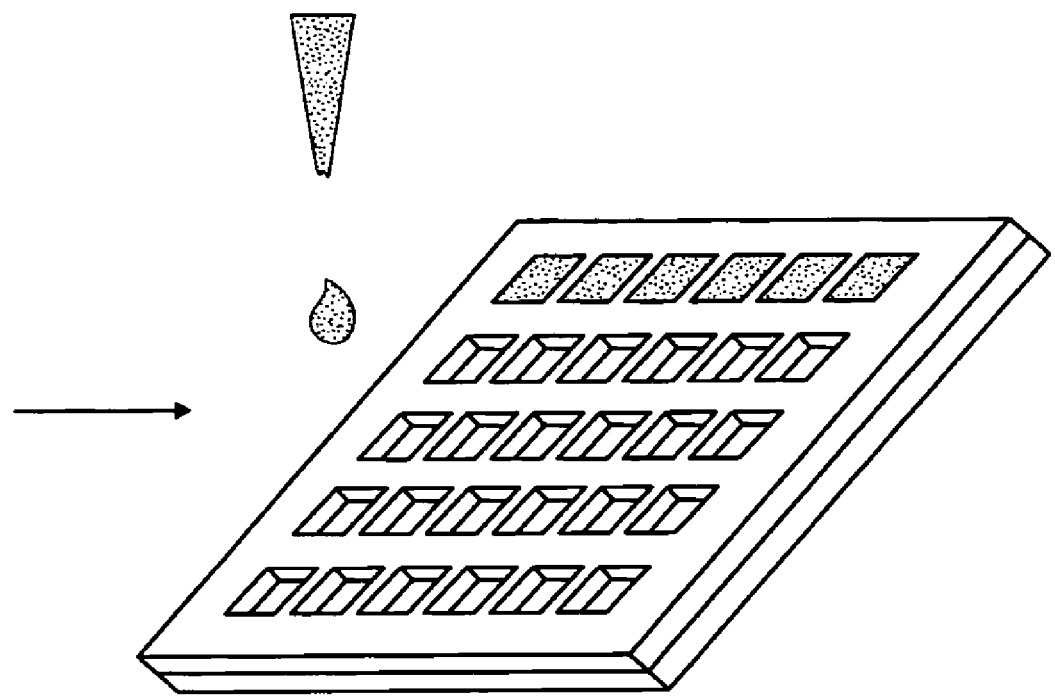
Figure 19B:
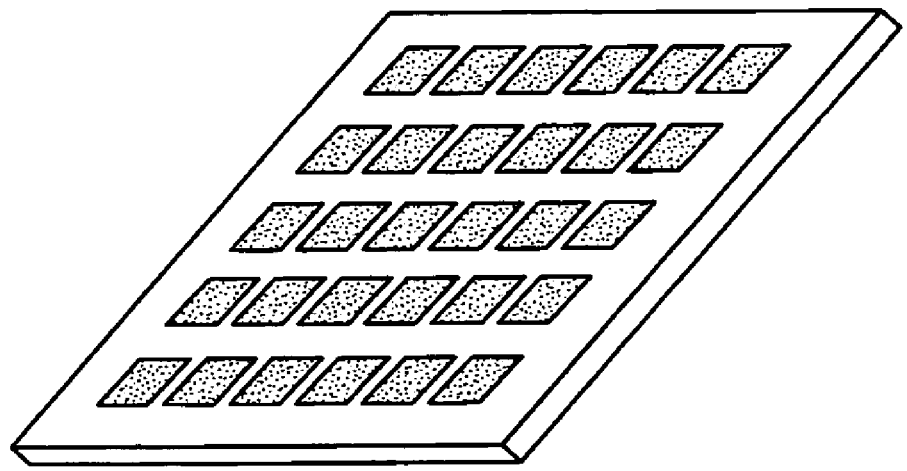
Figure 19C:
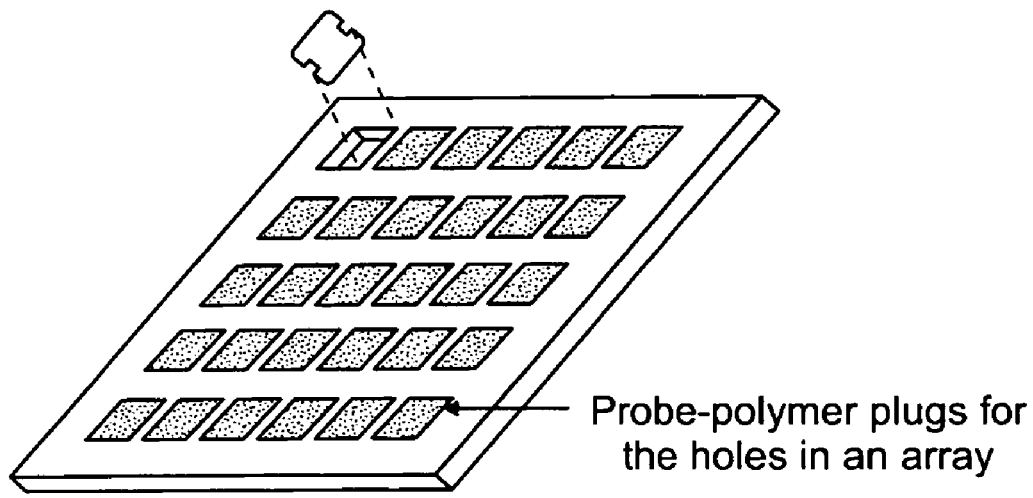
Figure 19D:
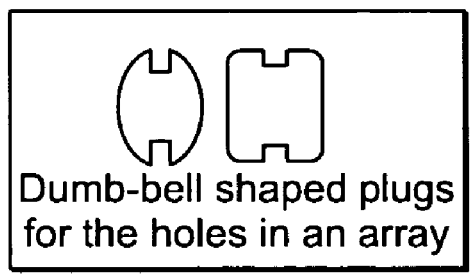
Figure 19E:
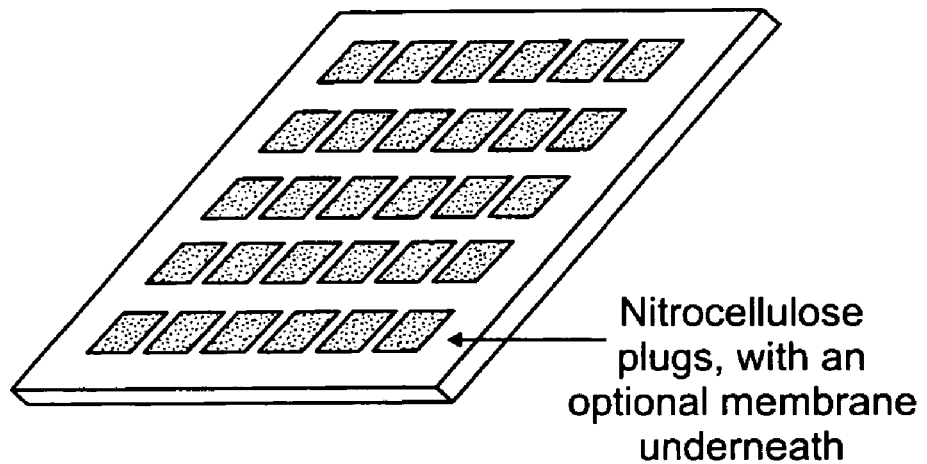
Figures 21D, 21E:
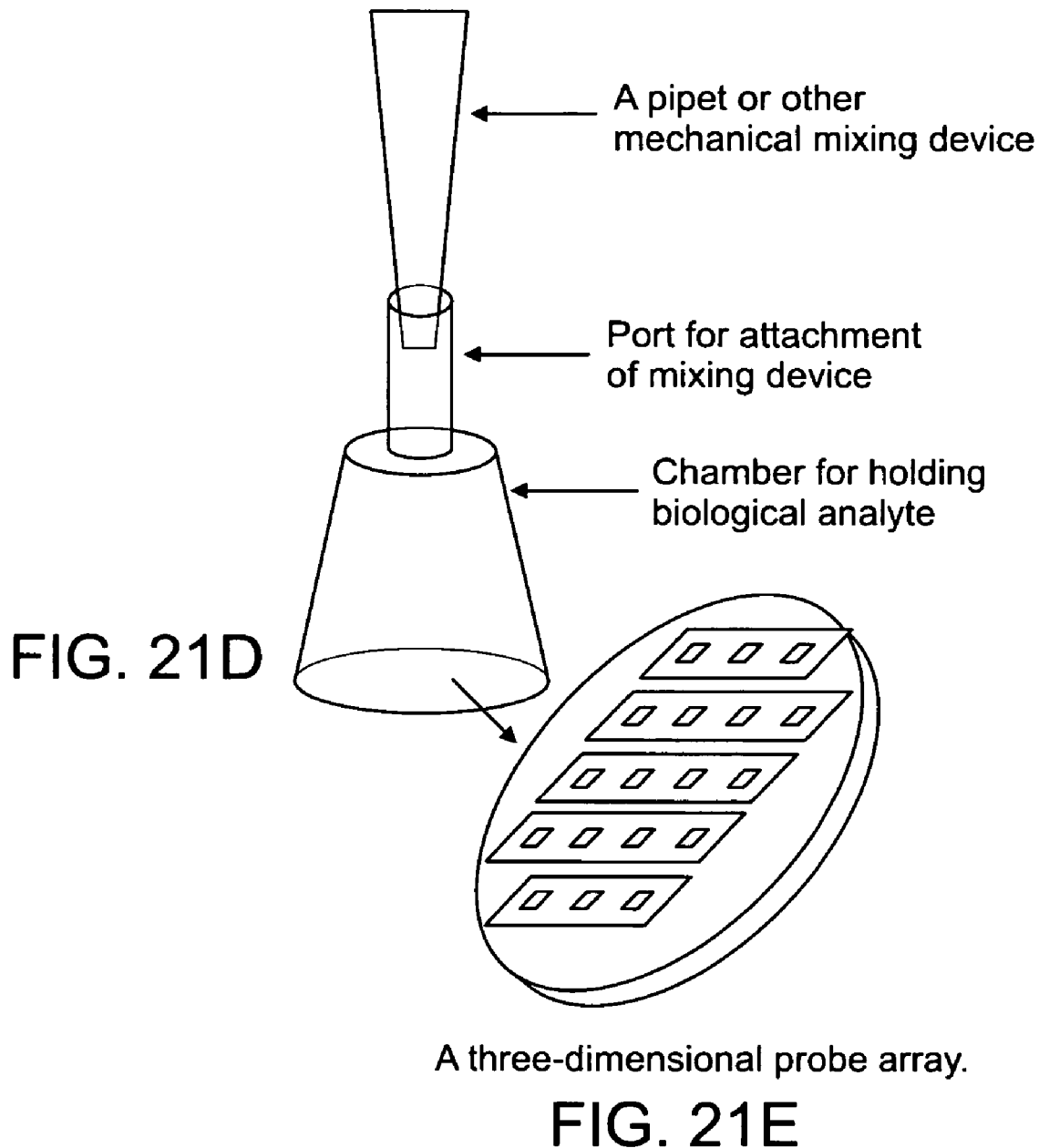

FIG. 14A presents yet another embodiment of the inverted array devices. Each elevated structure can have a number of probes attached in an array or an array of arrays format. The surface of the elevated structure can also have a three-dimensional configuration. The cross-section possibilities are shown in FIGS. 14B, 14C, and 14D. The sub-structure can either be elevated (14B), planar (14C), or depressed/dimpled (14D) such that one probe is attached to each of these sub-structures or features.

In other embodiments, the device can form a sealed chip with an enclosed reaction chamber (with holes for sample input, etc.). Assay read-out can be performed using standard techniques, such as optical methods (e.g., colorimetry and fluorescence), electrical detection, scanometric detection, surface plasmon resonance, impedence, capacitance, and chemical sensing (e.g., measuring changes in redox potential).

There are many advantages of this type of device/apparatus. This device/system is easy to automate, especially with the current robotic systems. The inverted array system/device can easily be moved from one reaction vessel to another. For example, biological samples can be loaded into one tray and the wash solution into another. The inverted array can be incubated with the sample and then simply moved to the wash plate for washing. Thus, assays can easily be automated and the automation can be done even on known instruments, which are adept at handling trays and devices that are similar to the microtiter plate format. Each device can optionally include a "handle" to help move the device. A robotic arm can move the device with the help of suction devices or with grabbers using standard devices and techniques if no handle is provided. The inverted array devices also have better mixing capabilities during assay procedures, because the microtiter plates can be mechanically moved or stirred in the presence of the "inverted array" device, thus providing mechanical mixing without dislodging the inverted array device.

In addition, multiple assays can be performed on a single device, because the elevated structures are widely separated from each other. A device with multiple elevated structures (an inverted array) can be incubated in a tray with multiple microwells, to perform simultaneous analyses of multiple samples, or for simultaneous analyses of the same sample with multiple sets of probes and/or under different conditions, or both.

Three-Dimensional Porous Array Devices

Microarray based biochips provide an ideal environment for multiplexed or parallel assays. However, a disadvantage of the system is that reactions are slow on microarrays due to slow diffusion of analytes. For example, in a binding assay, such as antigen-antibody binding, the reaction at a specific spot/site is dependent upon the transportation of selected molecules to that site and the reaction between probes at that site with the analytes (or targets) (see, e.g., Arenkov et. al; *Analytical Biochemistry,* 278, 123-131, 2000; Timofeev et. al; *Nucleic Acids Research,* 24 (16), 3142-3148, 1996; Van Beuningen R., Vice President Pamgene International: A Flow Through Porous Substrate Micro-Array for Post-Genomic Applications). Typically, diffusion of large target biomolecules is the slow and limiting factor in the binding assays, including assays on microarrays. This speed of this process can be substantially increased by mixing the analytes on the surface of the array with mechanical, electrical, electronic, optical, optoelectronic or other means. We have devised novel three-dimensional porous arrays to address these issues.

New three-dimensional porous microarray devices are illustrated in FIGS. 15A to 21E and 38A to 38D. These new devices consist of one or more porous gel-bound probes in an array or an array of arrays format. A device can have one or more such structures and the structures can be of any geometric shape and form. The structures can also be vertically straight, angled, or twisted. Thus, each device denotes a (multiplexed) reaction site. The device can be used to perform reactions simultaneously or sequentially. Any of the known substrates and chemistries can be used to create such a device. For example, glass, silica, silicon wafers, plastic, metals; and metal alloys can all be used as the solid support (see. e.g., Stillman B A, Tonkinson J L, Scleicher and Schuell; *Biotechniques,* 29(3), 630-635, 2000; Rehmna et. al; Mosaic Technologies Inc., *Nucleic Acids Research,* 27(2), 649-655, 1999).

The device can be manufactured in a number of ways. In one implementation, small holes are manufactured in a solid three-dimensional object using photolithography, etching, drilling, or other techniques known in the art. The holes can be of any geometric shape and can also have slits or grooves. Probes can be immobilized in these holes using a variety of methods including embedding them in a polymeric matrix. The probes can be separately mixed with a pre-polymeric gel and poured into or dispensed or deposited into each of the different holes to create polymeric, porous plugs. Subsequently, the probe-gel mixture can be polymerized using photo-initiators or other methods known in the art (see, e.g., Arenkov et. al; *Analytical Biochemistry,* 278, 123-131, 2000; Timofeev et. al; *Nucleic Acids Research,* 24 (16), 3142-3148, 1996; Mirzabekov et al.; *Methods in Molecular Biology,* 170, 17-38, 2001; and Mirzabekov et al.; U.S. Pat. No. 5,981,734, Nov. 9, 1999). The polymerized probe-gel material can be secured in the three-dimensional substrate by application of a secondary mask or a membrane on either or both sides. The securing material can also have slits or holes. Dumb-bell shaped polymeric plugs can also be used to immobilize probes, especially when the holes have grooves on the outside. This way the plugs cannot slip or fall out. Such holes and plugs can further be sealed in from two sides with another membrane with or without slits.

There are a number of advantages of this type of device including:

(i) The probes are bound in a three-dimensional porous material. Three-dimensional probe spots result in a higher amount and concentration of the probe bound to a spot, compared to a two-dimensional spot (i.e., binding of probes to a flat surface). This corresponds to increased spot resolution of the scanned microarray.

(ii) Porosity of the spot results in a porous array of spots. This gives better binding performance, due to enhanced diffusion of the target material through the entire spot as well as around the array of spots. There is no solid, impenetrable boundary between the porous material and the fluids on either of the two sides of the porous spot/plug. Thus, the biological sample being tested on such an array does not encounter any impermeable surface while passing through the pad. All the pad-based biochips known in the art have a solid-substrate covering any gel-pads (Such as products from Schleicher and Shuell, Motorola, and Mosaic Technologies) (see, e.g., Stillman B A, Tonkinson J L, Scleicher and Schuell; *Biotechniques,* 29(3), 630-635, 2000; Rehmna et. al; Mosaic Technologies Inc., *Nucleic Acids Research,* 27(2), 649-655, 1999) that result in poor diffusion of biological samples through the pads/spots.

(iii) The diffusion properties of the new devices can be further improved by mechanically mixing the fluid in a direction orthogonal to the plane of the array. For example, a vacuum suction device or a pipetman can be used for this purpose. This can substantially reduce the time it takes to perform a multiplexed assay. Sample mixing or transport can also be achieved or increased by using electrophoresis and other electronic (e.g., Nanogen, U.S. Pat. No. 6,238,624) or optical means.

(iv) Since the assay time is substantially reduced, this type of device can be adapted to manufacture a point-of-care device as well, especially where a single biochip is placed in a container and the fluid mixing is mechanically controlled (See, FIGS. 21A-E).

(v) Post-assay detection of the array results can be simplified and automated because the position and the size of each probe spot is uniform. This results in lower spot-to-spot and array-to-array variation.

(vi) Almost any material can be used as a substrate, since the problem of background fluorescence of the material is completely eliminated. The auto-fluorescence of only the probe-gel mixture needs to be considered.

(vii) Almost any attachment chemistry can be used to attach probes to the porous material. The attachment can be covalent as well as non-covalent. Thus, this type of format offers a wide variety of choices.

(viii) Adopting this type of a design for the microarray devices will substantially reduce manufacturing costs.

Additional references of interest include: GeneLogic/ HARC, U.S. Pat. No. 5,843,767 and http://homer.hsr.ornl.gov/cbps/Genosensors.htm.

Microfluidics Concentrators

New microfluidics-based devices (for example, see P. Chou, M. A. Unger, A. Scherer and S. R. Quake, "Integrated Elastomer Fluidic Lab on a Chip—Surface Patterning and DNA diagnostics," in *Proceedings of the Solid State Actuator and Sensor Workshop*, Hilton Head, S.C. (2000) and P. Chou, M. A. Unger, A. Scherer and S. R. Quake, "Integrated Elastomer Fluidic Lab on a Chip—Surface Patterning and DNA diagnostics," in *Proceedings of the Solid State Actuator and Sensor Workshop*, Hilton Head, S.C. (2000)) can also be incorporated into the biochip devices or be used separately. Such microfluidic devices can have chambers or channels that each contain an array of probes that bind complementary analyte targets. This type of an array serves to concentrate related analytes onto a single spot. Bound analytes could be released, using labile linkers on probes, and directed into a second channel or chamber. There the analytes could be further analyzed either on a second array of probes or in a capillary electrophoretic channel. Thus, each analyse is analyzed in two orthogonal dimensions providing a more accurate result. The microfluidic devices can be made on glass, polymers, plastic, silicon, metals, and a variety of other solid substrates.

As an example, this type of system can be used to perform a protein profiling using structural biological principals. There are only a limited number of representative protein folds, such as Immunoglobulin domain, that are used by a majority of proteins in nature. One can generate specific probes, such as antibody probes, that recognize specific protein folds. Such probes can be placed in the central chamber to bind all proteins with a similar fold in a biological sample. Bound proteins can then be further analyzed for specific types of proteins, such as antibodies or cytokines, into the next chamber. Thus, this microfluidics system performs biological analyses in two dimensions.

Figure 22A:
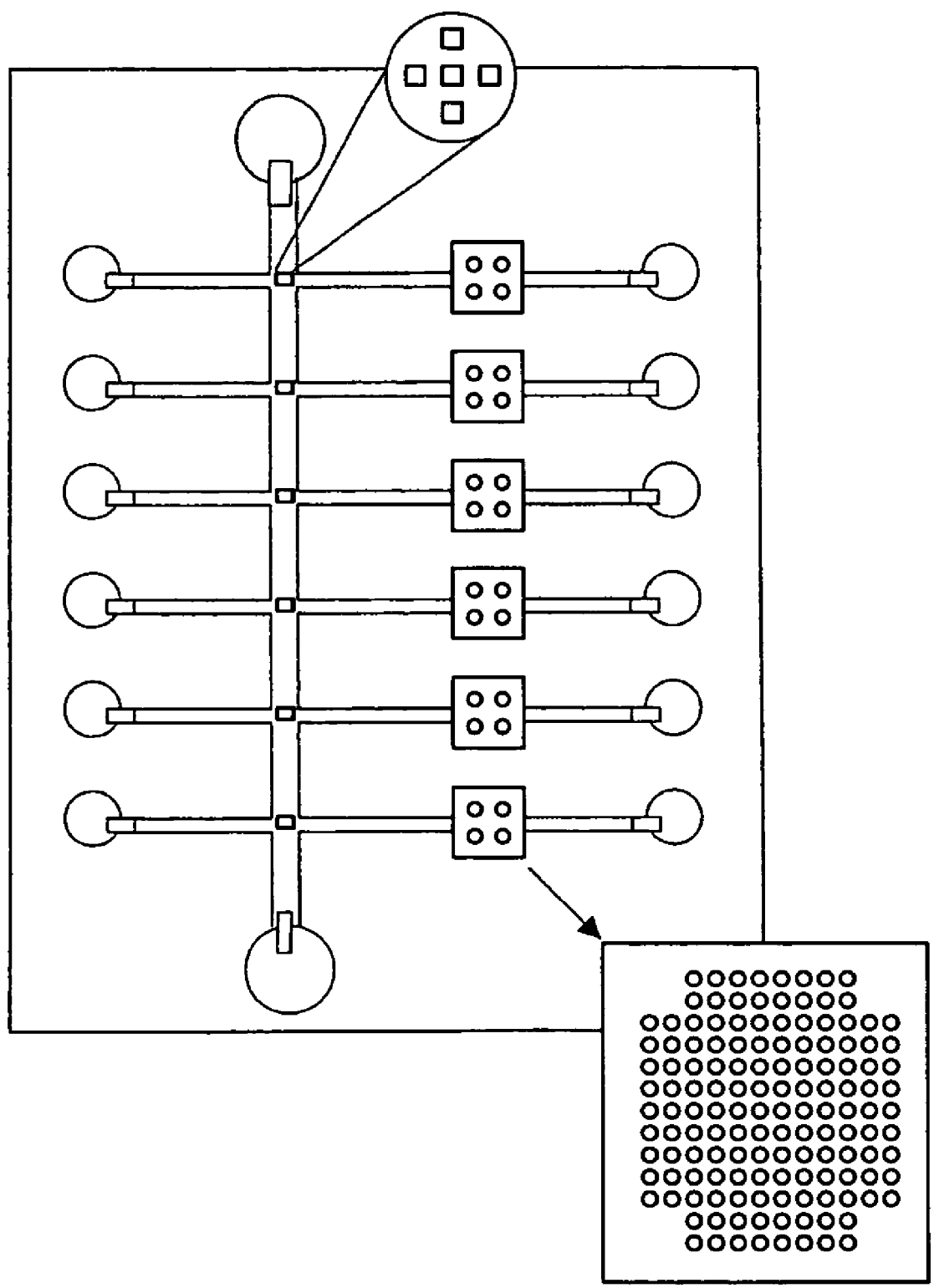
FIGS. 22A and B are schematic drawings of two different microfluidic concentrator biochips.
Figure 22B:
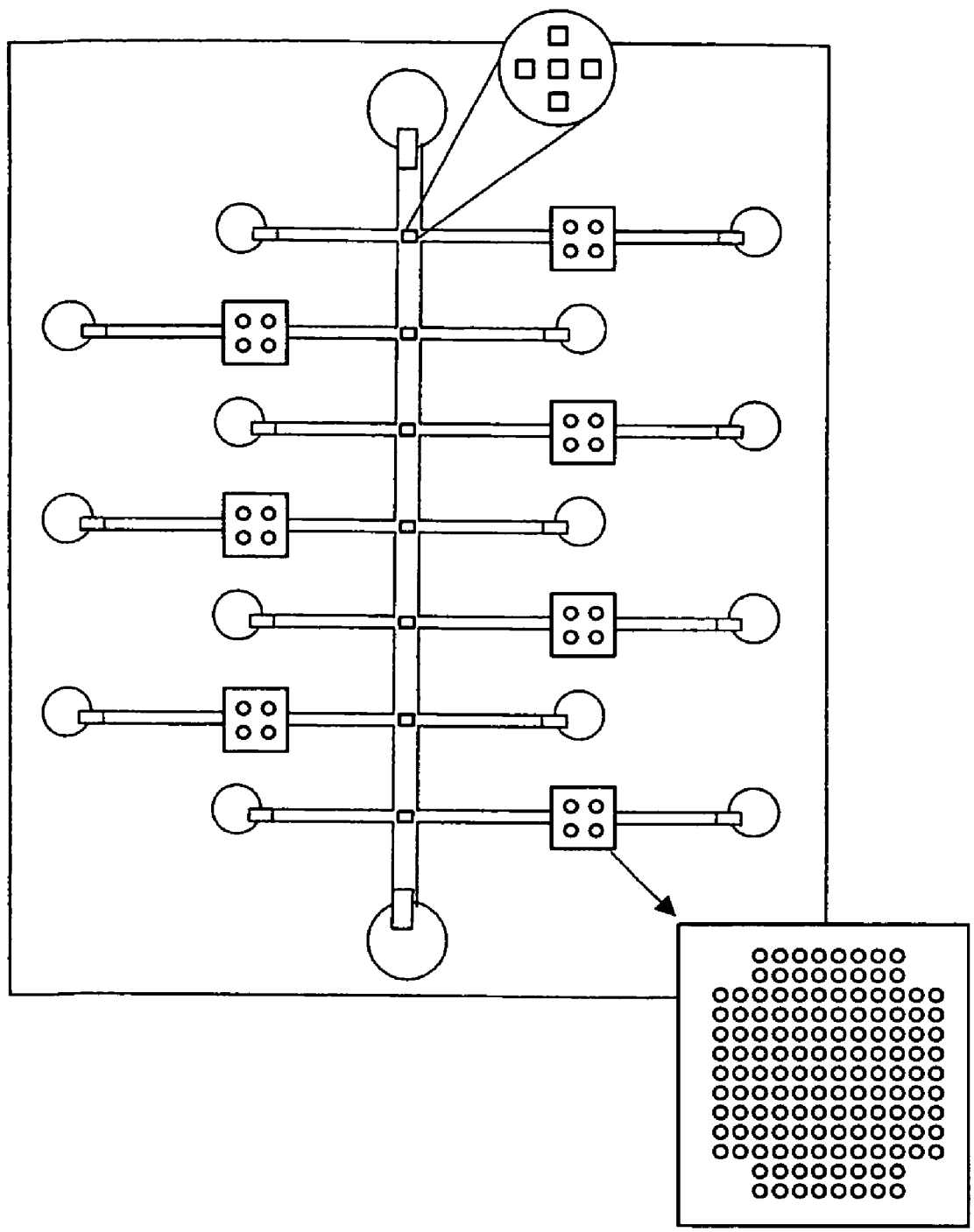
Figure 23B:
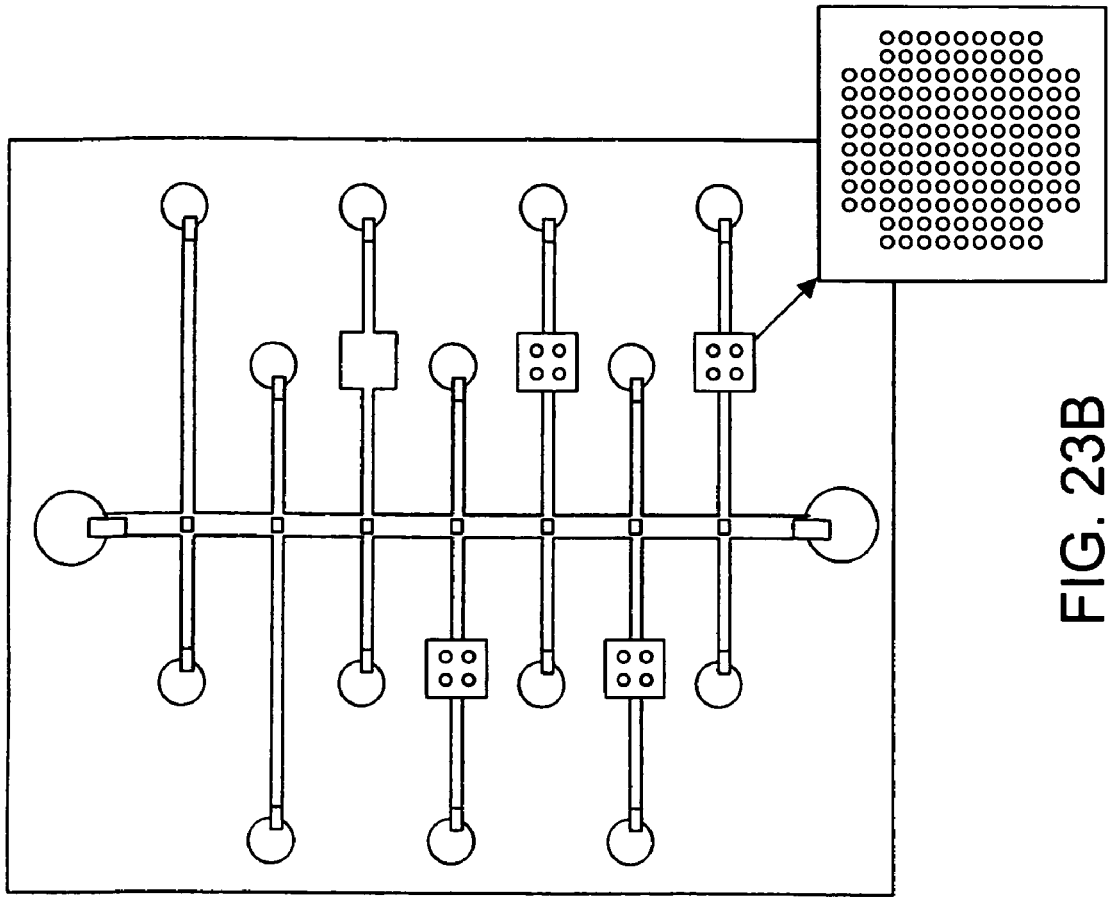
FIGS. 23A and B are schematic drawings of two different microfluidic biochips that are a microarray and microchannel combination chip for multiplexed analyses.
Figure 23A:
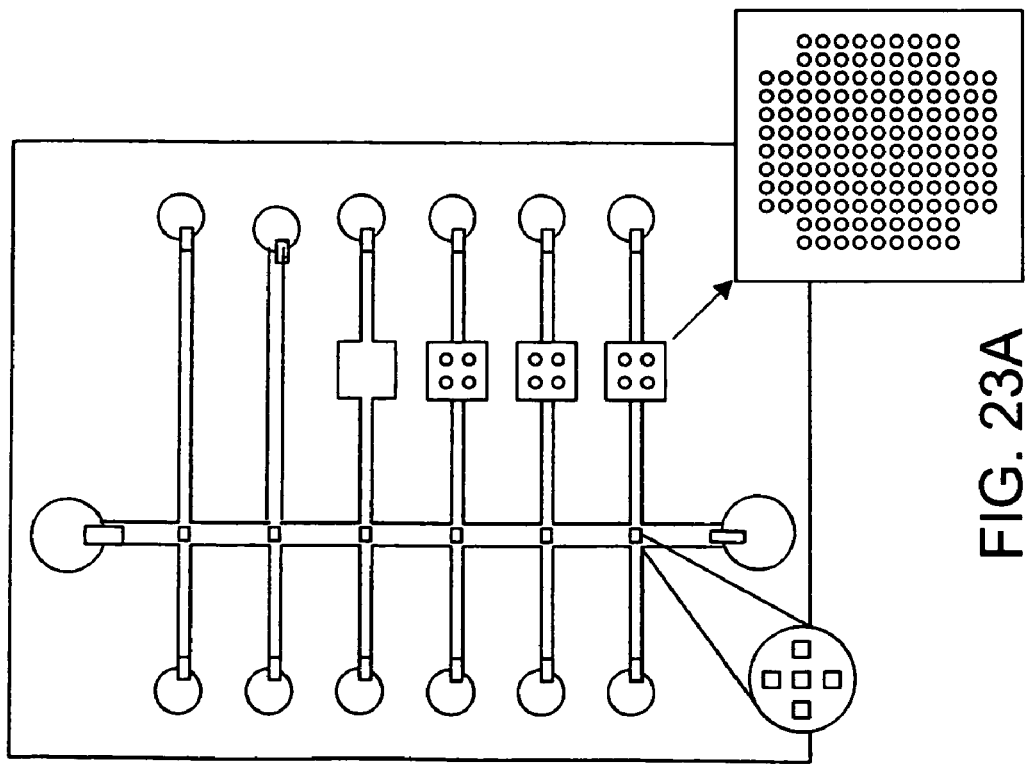
Figures 25A, 25B:
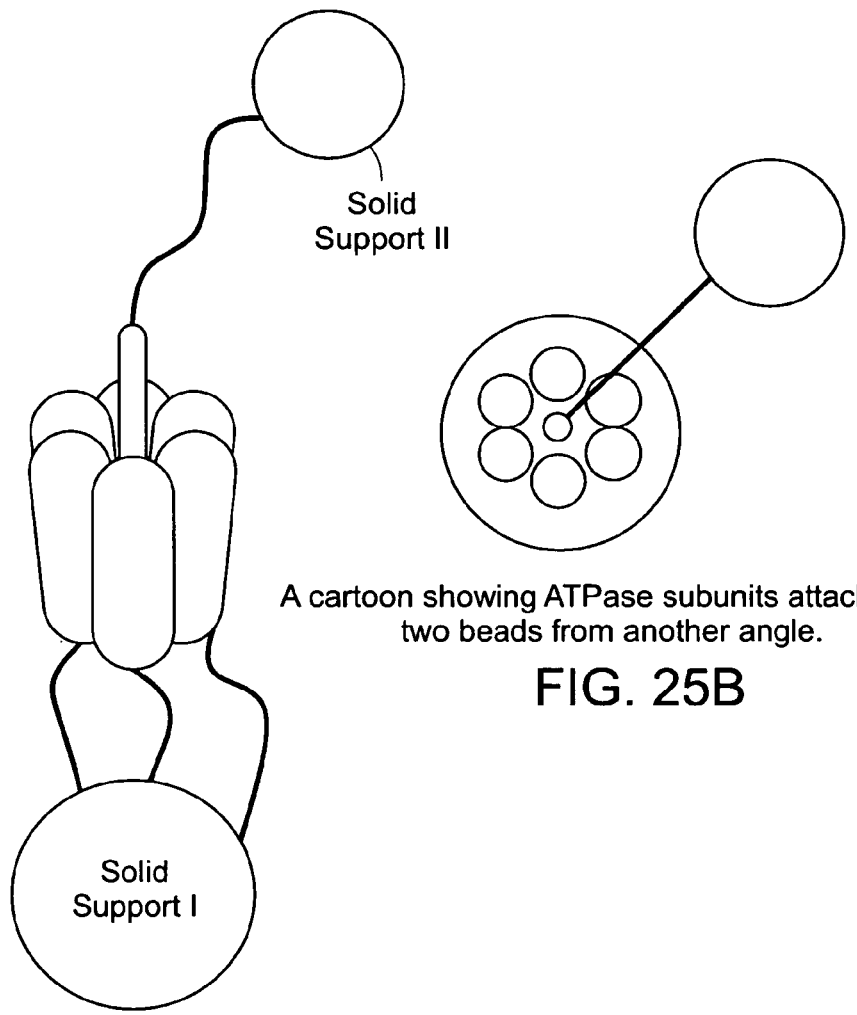
Figure 26A:
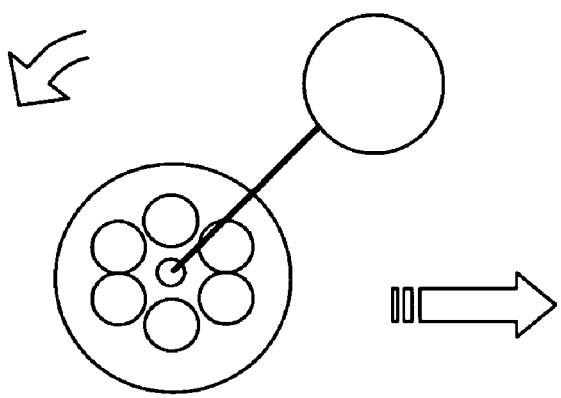
Figure 26B:
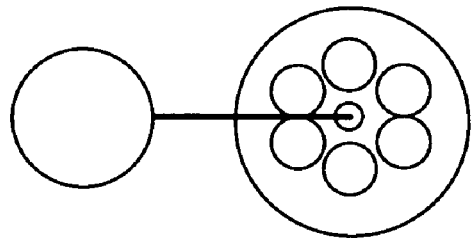
Figure 26C:
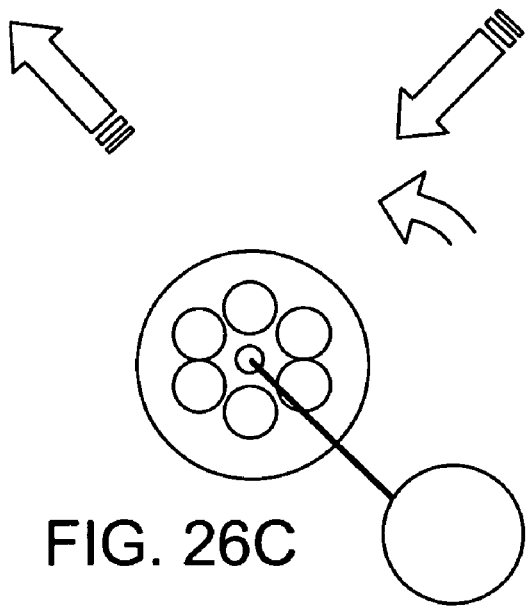
Figure 27:
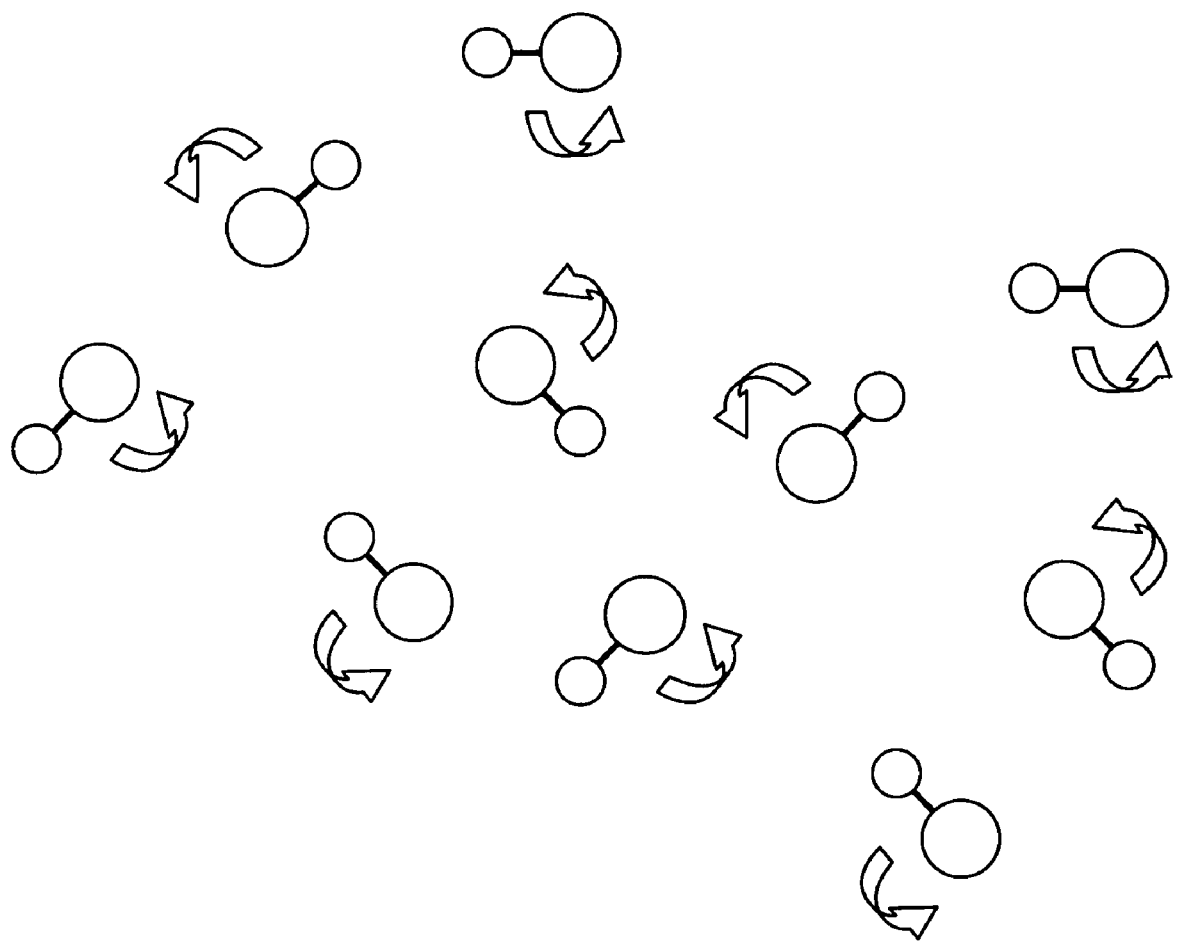
Figures 28A, 28B:
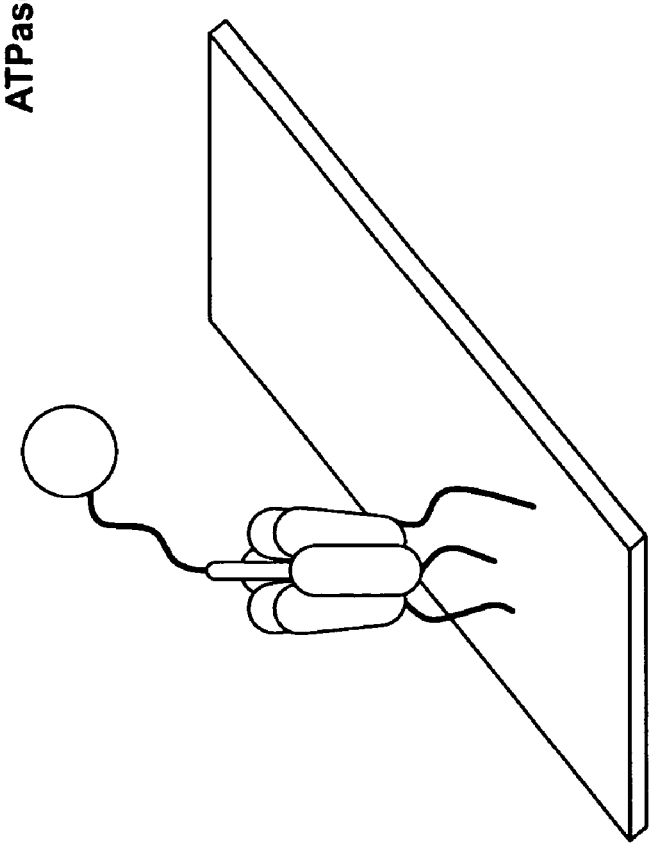
Figure 29:
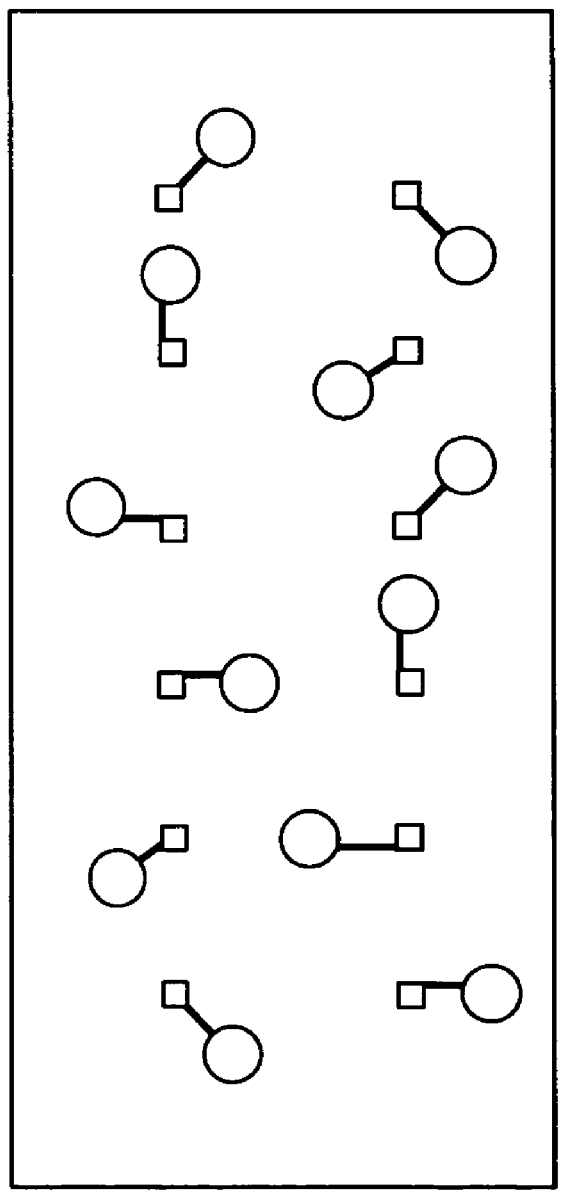
Figures 33A, 33B, 33C:
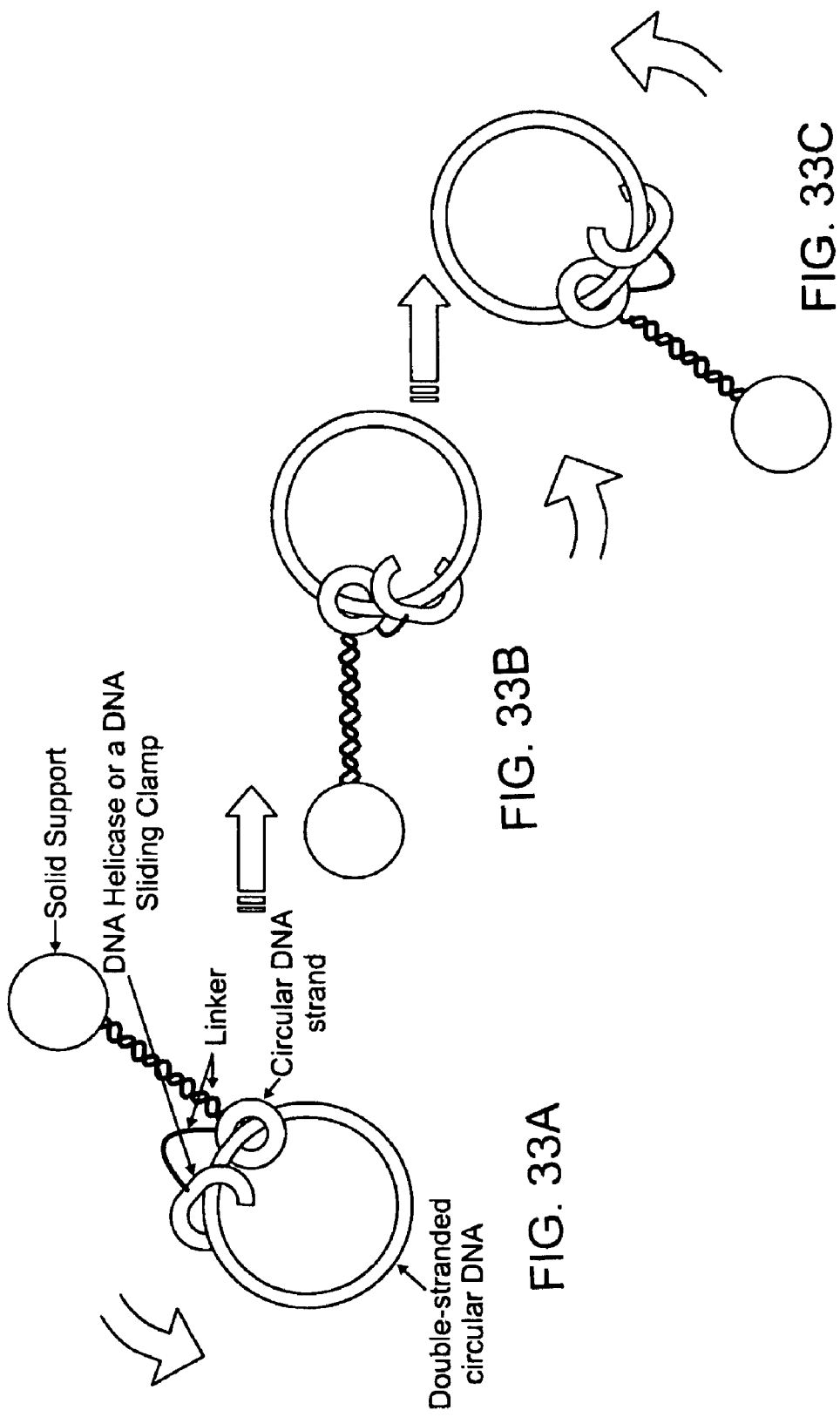
Figure 35A:
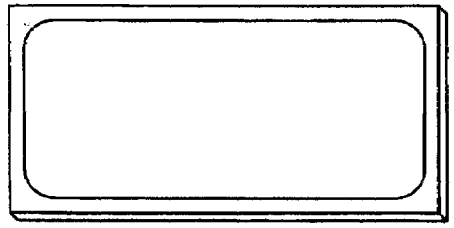
Figure 35B:
Figure 35C:
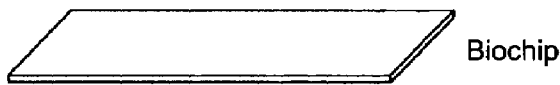
Figure 35D:
Figure 35E:
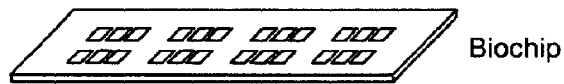
Figure 35F:
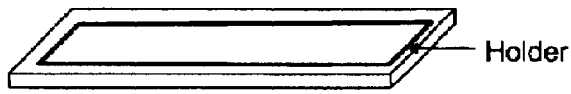
Figure 35G:

This is a device inside a device type of a system, which utilizes the fast assay time of a microfluidic device for analytical assays. There are a number of different ways that this type of device can be implemented. For example (FIGS. 22A and 22B and 23A and 23B), in one device (FIG. 22A), a central chamber has a set of probes, which are placed at the intersection of an orthogonal artery feeding into another chamber. The probes attached at this nodal point are non-specific in that they bind to a set of target molecules that are unique and yet have at least one similar characteristic. In a way, these nodes act at points in the stream where similar analytes are concentrated. Once this part of the assay is complete, the orthogonal artery is activated and transports each concentrated target set into separate chambers where they are further analyzed into unique positions, based on a second set of interactions. Thus, this system incorporates two orthogonal detection probes and will thus have a much better detection capability. Another advantage of this type of system, besides being a fast and improved detector, is that it can be combined with other types of biochip devices for enhancing their performance.

Some assays require analysis of molecules as well as enzymatic activity. The new methods use a novel microfluidic biochip for such assays. It will combine microarrays, for analyses of molecules, with microchannels, for analyses of enzymatic activity and reaction products, on a single biochip.

Methods of Using Clinically Intelligent Diagnostic Devices

The new diagnostic devices, e.g., diagnostic kits, are simple to use by physicians, nurses, clinicians, and/or agricultural worker. Samples from the subject (e.g., a human or animal patient, a blood sample from a blood supply, a sample from a plant) are easy to obtain and apply to the diagnostic kits. The results are easily read from a diagnostic kit reader device, e.g., a device that reads fluorescent light or other signals emitted from the probes of the diagnostic kit.

Specimen collection and purification methods (for subsequent association to a probe array of the system/device) include all front-end processes such as biological specimen collection, purification, isolation, and labeling as required. Most of the protocols are standard protocols and all are published. They are all known to anyone skilled in the art. As an example, one protocol is described.

Biological specimens, such as fluids (CSF, blood or urine etc.) are collected in standard collection tubes. In the case of blood or blood products, the serum is separated from nucleated cells using standard protocols. Serum specimens, CSF, etc. are used for all procedures described below. Following collection, serum samples should be stored at room temperature no longer than 8 hours. If the assay cannot be completed within 8 hours, the sample should be refrigerated at 2-8° C. If the assay cannot be completed within 48 hours, it should be frozen at −20° C. or lower. Frozen specimens should be mixed well after thawing and prior to testing. For NuScreen3 devices, nucleic acids will be isolated from the cells and purified.

Many assay methods are available and are known to anyone skilled in the art. Standard assays will be used in most cases. NuScreen assays will be based on nucleic acid detection by hybridization. Sample would be put on the multiplexed test sites and incubated for binding to occur. Single base extension (SBE) method, with queried base as the last nucleotide of the probe oligo, will be used for polymorphism analyses. Chemical as well as enzymatic ligation methods, as well as rolling circle amplification, can also be used. Reagents for performing SBE will be added and the test chamber will be sealed. For SBE (and other) assays the SBE reaction will be performed after optimizing (other methods such as hybridization, ligation, and RCA can also be used). The test sample will then be washed with a large volume of SSC or other aqueous washing solutions. This will also remove non-specific binding from the surface of the array device, e.g., biochips.

If non-fluorescent nucleotides were used in the SBE reaction, they will be developed using a secondary molecule labeled with a fluorophore (for example, a fluorescent streptavidin/antibody, or an HRP-streptavidin/antibody conjugate or an EFL-utilizing molecule-antibody conjugate or gold-antibody conjugate with subsequent silver treatment etc.). In a preferred detection method, DNA/RNA will be labeled with biotinylated nucleotides during PCR/IVT. TSA protocol will be used for detection (from NEN). RCAT (Molecular staging/Amersham) can be used in place of TSA for signal amplification. Such techniques and reagents are widely known and commercially available. A final washing step with an aqueous solution will follow to remove unused fluorophores etc. (detection can be primary or secondary).

ProScreen3 assays will include modified Western blot, ELISA and related methods, primarily for protein, peptides, nucleic acids and other biological moieties (competition assays and others can also be used). Samples will be put on the multiplexed test sites and incubated for a few minutes to several hours for binding to occur. Concentration of the probes on the biochip will be optimized according to the binding affinity of various biomolecules to their corresponding probes. Nucleic acid component of the test sample can be amplified and labeled (with fluorophores etc.) separately prior to the biochip assay. Amplified and labeled nucleic acid fraction can be combined with the non-nucleic acid fraction and then applied to the microarray. Subsequent to the binding reaction, the test sample will be washed away with a large volume of phosphate buffered saline (PBS) or another aqueous washing solution. This will also remove non-specific binder from the surface of the chip.

Binding reactions will be developed using secondary molecules labeled with a reporter group, such as a fluorophore (for example, a fluorescent antibody, or an HRP-antibody conjugate) or an EFL-utilizing molecule-antibody conjugate or gold-antibody conjugate with subsequent silver treatment. In one useful method, sandwich ELISA coupled to biotin/HRP will be used. A TSA step can be used as signal amplification method. RCAT (Molecular staging/Amersham) can be used in place of TSA for signal amplification. Alternatively, a chemiluminescent or radioactive or electroactive or redox active or IR-active agent etc. can be used. Such techniques and reagents are widely known and commercially available. A final washing step with an aqueous solution will follow to remove unused fluorophores etc.

UniScreen3 assays are similar to ProScreen3 assays, but are more comprehensive and inclusive of a greater variety of target analytes.

The results are monitored by detection and/or imaging of the diagnostic kit, such as a biochip for the association (binding/hybridization/extension) of the target molecules/agents on specific sites in the arrays (within each device) can be achieved by scanning/imaging. Such methods are widely used and the devices to perform these operations are commercially available. There are a number of commercially available devices that can be used with no or minor modifications. Examples include the GenePix3 system (Axon Instruments, Union City, Calif.), Scanarray (Packard BioSciences, MA), and Arrayworx (Applied Precision, WA).

The results are determined by processing the images to determine information about the target biological sample such as the presence and amount of specific molecular/other constituents that leads to the screening output. Software tools will be used to obtain diagnosis from the read-out of any test slide. Commercially available softwares such as GenePix Pro (Axon Instruments), Scanarray (Packard), Microsoft® Excel® (Microsoft), and Adobe® Photoshop® (Adobe) can be used, e.g., with minor modifications.

Specific Types of Kits

Human Diagnostic Kits

A wide variety of human diagnostic kits can be created using the methods and probes described herein. These kits provide information to a clinician or physician about the causes for specific symptoms, or clusters of symptoms, presented by a patient.

Specific examples of human diagnostic kits are in the Examples section below and include: Headache/fever/meningismus (Meningitis) Kit, Cough/fever/chest discomfort/dyspnea (Pneumonia) Kit, Jaundice (Liver failure) Kit, Recurrent Infection (Immunodeficiency) Kit, Joint Pain Kit, and many others.

Human Detection Kits

Kits of this type provide information about the current state of a patient's condition, such as the patient's immunization or immunocompetance state or the presence of a tropical disease in the body (e.g., a disease not yet showing symptoms), or the condition of a medical product, such as a blood supply or a donated organ.

Specific examples of human detection kits are in the Examples section below.

Animal Diagnostic and Screening Kits

These kits will allow comprehensive, cost-effective, rapid diagnosis of numerous congenital and acquired diseases based on animal's clinical presentation of the specific symptoms and/or conditions. In addition, animal exposure to different pathogens or products of pathogens (e.g., toxins, or the result of immunization) can be evaluated, as well as specific genes and/or diseases linked to improved breeding (e.g., the size of the litter, and the meat/milk production). These kits will be species-specific. Examples include: Laboratory Mouse Kit, Sheep Kit, Laboratory Rat Kit, Dog Kit, Simian Kit, Racing Horse Kit, Cattle Kit, Chicken Kit, Porcine Kit, Lamb Kit, Fish Kit.

Agriculture Kits

These kits will allow comprehensive, cost-effective, rapid diagnosis of numerous congenital and acquired diseases based on plant's clinical presentation of the specific symptom. In addition, plant exposure to different pathogens will be evaluated, as well as specific genes and/or diseases linked to improved plant growth (e.g. the size of the plant, the corn/rice production etc). These kits will be species specific. Some of these are listed below: Corn Kit, Cotton Kit, Tobacco Kit, and Rice Kit.

Other Kits

The invention covers additional, more specific kits as follows: Forensic Kits; Food-borne pathogens (viral and microbial) and antibiotic resistance Kit; Inspection of imported goods—agricultural and livestock Kit; Pesticide Kit; Inspection of Cosmetics (e.g., Mad Cow Disease) Kit; Bioterrorism Kit (such as smallpox, anthrax, plague, botulism, tularemia, and hazardous chemical agents); and Influenza Surveillance Kit (screens all known strains of influenza).

EXAMPLES

The invention is further described in the following examples, which do not limit the scope of the invention described in the claims.

Example 1

Preparation of Clustered Probe Arrays on Various Solid Supports

A blank 3D-Link3 slide (Surmodics), which contains NHS-ester groups at the surface of the slides, is used in this example. The slide is placed in a chamber for arraying of probes onto the slide surface. Probe molecules (ZFPs and other polypeptides) are dissolved in a bicarbonate buffer at pH 8.3, and are spotted onto the glass slides using an arrayer. All the probe molecules contain an amine group for reaction with the slide surface. The spotting solution can also contain chemicals that have low vapor pressure (high boiling point) and that preserve the activity of probe molecules (such as glycerol, trehalose, and polyethylene glycol). The spotting is done under controlled conditions (such as humidity, in one instance around 70% relative humidity, temperature, for example around 4° C., pressure, and air-flow).

After the probes are spotted, the slides are put in the development chamber for 1-12 hours. The chamber is kept under controlled conditions (such as humidity, temperature, pressure, and air-flow) as well. The slides are then treated with a blocking buffer (aqueous buffer, pH 8.3 containing BSA or other blocking reagents) for an appropriate amount of time. The slides are then washed and stored.

A blank EZ-Ray® slide (Mosaic Technologies) is treated with an aqueous buffer containing reducing agents (such as DTT or TCEP) to activate the slide surface into free thiol form. The reducing agents are then washed away with water and the activated slide can be stored under inert atmosphere in a cool, dark place. Activated thiol-surface is next converted to an amine reactive surface. The slide is treated with a heterobifunctional cross-linkers, such as N-succinimidyl-3-maleimidopropionate (SMP), N-(11-Maleimido-undecanoyloxy)-sulfo-succinimide (Sulfo-KMUS) (or similar agents that contain a thiol-reactive maleimide group on one end and an amine-reactive NHS-ester group at the other), in aqueous buffer and at neutral pH (other reaction conditions, such as a different pH, can also be used). Thiols react with the maleimide moieties of the cross-linker, thus converting thiol-groups into amine-reactive NHS-ester groups. The slide is placed in a chamber for arraying of probes onto the slide surface.

Probe molecules (proteins, such as antibodies, antigens and ZFPs, peptides, such as antigens, haptens and MGBs, glycoproteins, polysaccharides, amine-labeled nucleic acids and other probe molecules) are dissolved in buffers at slightly basic pH (for example, bicarbonate buffer at pH 8.3) and are spotted onto the glass slides using an arrayer. All the probe molecules contain an amine group for reaction with the slide surface. Spotting solution can also contain chemicals (such as glycerol, trehalose, and polyethylene glycol) that have low vapor pressure (high boiling point) and that preserve the activity of probe molecules. Spotting is done under controlled conditions (about 70% relative humidity and about 4° C., at normal pressure).

After the probes are spotted, the slides are put into a development chamber for 1-12 hours. Conditions in the chamber (humidity, temperature, pressure, air-flow etc.) are controlled as well. The slides are then treated with a blocking buffer (aqueous buffer, pH 8.3 containing BSA) for an appropriate amount of time, washed, and stored.

Xenoslide A3 (aminosilane slides from Xenopore) slides are silanated and ready to use as received. They can be stored at room temperature. A solution of the probes is prepared for spotting. For nucleic acid probes, the concentration is in the range of 1 ng to 1 ug per ml. Spot size can be controlled by use of solvent mixtures. Correct choice of co-solvent will result in lower surface tension of the mixture compared to water and controlled spreading of the spot. Volatility of the solvent mixture and thus the drying time can also be controlled by solvent composition. Use of a lower volatility co-solvent will increase the drying time.

DMSO can be used because it is a good solvent for nucleic acids, is miscible with water in all proportions, and has lower surface tension and lower volatility than water. Typically, up to 50% DMSO is used. Alternatively, glycerol can be used in place of DMSO. The solution is spotted onto the slide. If using only water, it is helpful to maintain a humidity of 75-80% for a few minutes to allow binding to take place. DNA can be cross-linked to the slide by exposing the slide to UV light with up to about 200 millijoules of radiation. The slide is now ready for hybridization.

Xenoslide N3 (nickel chelate surface) slides and nickel chelate cover slips can be used with cobalt chelate surfaces (as per manufacturer). The slides are coated with the chelating agent and are charged with either nickel or cobalt ions. They are ready to use as received. They can be stored at room temperature. A solution of His-tagged probes (e.g., protein, peptide, or nucleic acid) in a neutral pH buffer or a slightly basic buffer is prepared. Tris buffer is a good choice. The solution concentration should be in the range of 1-3 ug/ml. The solution is spotted onto the slide or cover slip, and kept wet for 5-10 minutes by putting into a humid chamber. This allows the binding to take place. The slides are air dried. They are now ready for use in capture experiments.

Xenoslide D3 (aldehyde surface) slides are chemically modified to have a high density of aldehyde groups on the surface. These groups immobilize aminolabeled DNA, proteins, and peptides by Schiff base chemistry. A solution of probes (such as amino-labeled oligos) is prepared in a neutral pH buffer at a concentration of 1 to 3 Tg/ml. Tris buffers should not be used because they contain free amine groups that can react with the plate surface and prevent oligo binding. The oligos are spotted onto the slide, and the slide is kept wet for 5-10 minutes by insertion into a humid chamber at a relative humidity of 50-70%. The Schiff base reaction is reversible at acid pH. For greater stability, the Schiff base can be reduced with sodium borohydride. A 1% solution in water, 30 minutes at room temperature is usually adequate. This also blocks unreacted groups. If the reducing step is omitted, the unreacted aldehyde groups should be blocked with a solution of ethanolamine in water (1% by volume). The slides can be air-dried, and are now ready to use in hybridization tests.

Xenoslide E3 (epoxy surface) slides are chemically modified to have a high density of epoxy groups on the surface. The epoxy groups are highly reactive to primary amino groups and hydroxy groups at high pH. A solution of the probes, e.g., oligos or polypeptides to be bound, are prepared in a solution at pH 10.5-11 at a concentration of 1-3 Tg/ml (proteins can be spotted at a lower pH with a longer incubation time). The probe solution is spotted onto the slide, and the slide is kept wet for 5-10 minutes by putting it into a humid chamber at relative humidity of 50-70%. Blocking of the slide is usually not necessary because the reaction of the epoxy group at neutral pH is quite slow. Therefore, DNA and oligos will only bind by hybridization. The slide is air-dried and is now ready for hybridization experiments.

Xenoslide S3 (streptavidin surface) slides have a high density of streptavidin immobilized on the surface. The binding capacity is approximately 5 picomoles of biotin binding sites per square cm. The slides are ready to use as received. Unused slides can be stored in their container under refrigeration. A solution of biotinylated probes (proteins or oligo at a concentration of 1 to 3 Tg/ml) is prepared in a neutral pH buffer such as 1×SSC or phosphate buffer. The probe solution is spotted onto the slide, and the slide is kept wet for 5-10 minutes by putting it into a humid chamber at a relative humidity of 50-70%. The slides are air-dried and are then ready for hybridization experiments.

UniScreen3 Biochips can be prepared as follows. Microscope glass slides with thiols on the surface (such as EZ-Ray3 slides from Mosaic, or Thiol slides from Xenopore) are activated to a free thiol form, and are then washed with water and stored under nitrogen atmosphere in a cool, dark place. The slides are treated with hetero-bifunctional cross-linkers, such as N-succinimidyl-3-maleimidopropionate (SMP), N-(11-Maleimido-undecanoyloxy)-sulfo-succinimide (Sulfo-KMUS) etc., dissolved in aqueous buffers at neutral pH. The thiols react with the maleimide moieties of the cross-linker, converting them into amine-reactive compounds. Probe molecules are dissolved in buffers with slightly basic pH (for example, bicarbonate buffer at pH 8.3) and are spotted onto the glass slides using an arrayer. The spotting is done under controlled humidity (around 70% relative humidity) and temperature (around 16° C.) conditions.

After the probes are spotted, the slides are put into the development chamber for 1-12 hours. The chamber is kept under controlled conditions (such as 70% RH, 16° C.). The slides are then treated with a blocking buffer (aqueous buffer, pH 8.3 containing BSA and other reagents) for an appropriate amount of time, and are then washed and stored.

Example 2

Jaundice (Liver Failure) Kit

This kit allows comprehensive, cost-effective, rapid diagnosis of numerous diseases/conditions based on a patient's clinical presentation of jaundice/liver failure. Diagnosis of genetic, autoimmune, and infectious diseases is based on the precise detection of specific gene mutations or other markers (such as microbial-specific sequences, or autoreactive antibodies) using DNA, RNA, and protein (spotted antigenic proteins and specific mAbs) chips. Jaundice kits are focused on the etiologic considerations of jaundice. In addition, therapeutic markers may be included to test for different potential therapeutic options. Briefly, one or more of three groups of etiological conditions are evaluated: A) autoimmune hepatitis, B) viral-induced hepatitis, and C) genetic diseases causing jaundice and/or liver enlargement. See, e.g., Feldman: Sleisenger & Fordtran's Gastrointestinal and Liver Disease, 6th ed. (W. B. Saunders Company 1998); McFarlane, "IG: The Relationship between autoimmune markers and different clinical syndromes in autoimmune hepatitis," Gut 42:599-602, 1998; Manns, M P, "Liver/Kidney Microsomal Autoantigens," in Autoantibodies (ed: Peter J B and Y. Shoenfeld, Elsevier, 1996), pp 462-466; and Lee: Wintrobe's Clinical Hematology, 10th ed. (Lippincott Williams & Wilkins, 1999).

The kits may include probes that detect targets for potential therapeutics.

The kits will include probes that detect at least five or more of the following targets:

1) Anti-LKM-1 antibodies (IgG and IgM)—the major target antigen of LKM-1 antibodies has been identified as cytochrome P450 2D6, a microsomal protein found in the endoplasmic reticulum.

2) Anti-mitochondrial M2 antibody—M2 antigens can be used as probes. M2 antigens have been located in the inner mitochondrial membrane and have been found to be part of the pyruvate dehydrogenase complex and have molecular weights of 50 and 70 kD.

3) Hepatitis A infection—this virus can be detected indirectly by detecting IgG Anti-HAV antibodies using purified recombinant human hepatitis A antigens as probes.

4) Hepatitis B infection—purified recombinant human hepatitis B antigens (HBcAg, HBsAg, HbeAg) can be used as probes.

5) Hepatitis C infection—purified recombinant human hepatitis C antigen (NS3, NS4, NS5, and core regions antigens) can be used as probes.

6) Hepatitis D infection—purified recombinant human hepatitis D antigen can be used as probes.

7) Hepatitis E infection—purified recombinant human hepatitis E antigen can be used as probes.

8) CMV infection—CMV immediate-early antigens (pp 65) or DNA in peripheral-blood leukocytes can be used as probes to hasten the diagnosis of CMV disease in certain populations, including organ transplant recipients and persons with AIDS.

In addition, the kits will include probes that detect gene mutations and/or allelic variations that can cause the elevation of bilirubin/liver injury. For example, some probes in the jaundice kits will be designed to detect the following mutations/allelic variations:

Dubin-Johnson Syndrome; Hyperbilirubinemia Type I; Acute Hepatic Porphyria; Delta-Aminolevulinate Dehydratase Deficiency; Porphobilinogen Synthase Deficiency; Alagille Syndrome; Arteriohepatic Dysplasia; Cholestasis with Peripheral Pulmonary Stenosis; Alpha-1-Antitrypsin Deficiency; Carbamoylphosphate Synthetase I Deficiency; Carbamyl Phosphatase Deficiency; Carbamyl Phosphate Synthetase Deficiency; Carnitine-Acylcarnitine Translocase Deficiency; Citrullinemia; Ferrochelatase Deficiency; Heme Synthetase Deficiency; Fatty Acid Oxidation Disorder, Unspecified; Fructose 1,6 Bisphosphatase Deficiency; Galactosemia; Galactose Epimerase Deficiency; Galactose-1-Phosphate Uridyltransferase Deficiency; NGlutaricacidemia Type II; Glutaricaciduria Type II; Glycogen Storage Disease Type I/Ia; Glucose-6-Phosphatase Deficiency; Von Gierke Disease; Glycogen Storage Disease Type III; Cori Disease; Debrancher Deficiency; Forbe Disease; Glycogen Storage Disease Type IV; Brancher Deficiency; Glycogen Storage Disease Type IX; Glycogen Storage Disease Type VIII; Phosphorylase Kinase Deficiency of Liver; Glycogen Storage Disease Type Ib; Glucose-6-Phosphate Translocase Defect; Glycogen Storage Disease Type VI; HERS Disease; Hereditary Coproporphyria; Coproporphyrinogen Oxidase Deficiency; Harderoporphyria; Hereditary Fructose Intolerance; Fructosemia; Hereditary Hemochromatosis; Long Chain 3-Hydroxyacyl-CoA Dehydrogenase Deficiency; Acute Fatty Liver; Disease of Pregnancy; HELLP; Hemolysis; Enzymes, and Low Platelets; LCHAD Deficiency; Trifunctional Protein Deficiency; Long Chain Acyl-CoA Dehydrogenase Deficiency; LCAD Deficiency; Medium Chain 3-Ketothiolase Deficiency; MCKAT Deficiency; Medium Chain Acyl-Coenzyme A Dehydrogenase Deficiency; MCAD Deficiency; Mucopolysaccharidosis Type II; Hunter Syndrome; MPS II; Mucopolysaccharidosis Type IIIB; MPS IIIB; Sanfilippo Syndrome Type B; Mucopolysaccharidosis Type IIIC; MPS IIIC; Sanfilippo Syndrome Type C; Mucopolysaccharidosis Type IVB; MPS IVB; Morquio Syndrome Type B; Mucopolysaccharidosis Type VI; Arylsulfatase B Deficiency; MPS VI; Maroteaux; Lamy Syndrome; Mucopolysaccharidosis Type VII; Glucuronidase Deficiency MPS; MPS VII; Sly Syndrome; Niemann-Pick Disease Without Sphingomyelinase Deficiency; Niemann-Pick Disease Type C; Niemann-Pick Disease Type D; Niemann-Pick Disease, Nova Scotian Type; Ornithine Transcarbamylase Deficiency; OTC Deficiency; Phosphorylase Kinase Deficiency of Liver and Muscle; Polycystic Kidney Disease, Recessive; ARPKD; PKD, Infantile; PKD, Recessive; Salla Disease; Sialic Acid Storage Disease; Sialidosis; Glycoprotein Neuraminidase Deficiency; ML I; ML1; Mucolipidosis; Wilson Disease; Wolman Disease; Cholesterol Ester Storage Disease; and/or Zellweger syndrome; Cerebrohepatorenal Syndrome.

To use a jaundice kit, blood is drawn from the patient. The serum is separated from the nucleated cells. Serum specimens are used for all protein-based procedures performed on a polypeptide-based array or chip. Following collection, the serum is separated from the clot. Serum samples are stored at room temperature no longer than 8 hours. If the assay is not completed within 8 hours, the sample is refrigerated at 2 to 8° C. If the assay will not be completed within 48 hours, or for shipment of the sample, the sample should be frozen at −20° C. or lower. Frozen specimens must be mixed well after thawing and prior to testing. Peripheral blood leukocytes (PBL) are isolated by percoll gradient, counted, and frozen at 20° C. or lower. For DNA and RNA chips, the DNA and RNA is purified from these cells.

The following diagram shows how the blood sample is tested:

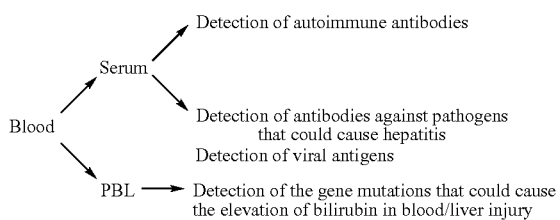

Protein chip technology: A contact-printing robot is used to create a dense array of immobilized proteins on glass slides to create the jaundice kits. Covalent attachment to aldehyde-derivatized glass occurs through a Schiff's base at several protein surface positions. Excess reactivity is quenched with a layer of phospholipids, which also helps to reduce nonspecific binding (peptide and small protein arrays will be made on activated phospholipid monolayers). The proteins/peptides contain a stable structure. Even after they have been attached to the wells of a polystyrene microwell plate, they continue to preserve their antigenicity in their native state (e.g., these probes are fully recognized by autoreactive/and/or anti-viral antibodies from patients sera). After the blood sample is applied to the surface of the probe array, the sample is washed off, leaving only target analytes bound to the probes. Thereafter, standard antibodies, e.g., monoclonal antibodies, or IgG or IgM antibodies, attached to labels or reporter groups, such as fluorescent labels (e.g., FITC and rhodamine), are applied to the array, and bind to any analytes attached to the probes, in the manner of a standard ELISA assay.

As an example, the target analyte LKM-1 antibody is detected using purified full-length recombinant human cytochrome P450 2D6 antigen bound to the surface of a glass slide. Diluted patient sera are added, allowing any LKM-1 antibodies present to bind to the immobilized antigen. Unbound sample is washed away and a FITC (green)-labeled anti-human IgG antibody and a rhodamine (red)-labeled anti-human IgM is added. After washing away any unbound anti-human mAbs, the intensity of the color is measured using standard techniques and instruments. The assay is evaluated by measuring and comparing the color intensity that develops in the patient samples with the color in a control sample.

M2 antibodies can be detected in a similar manner using purified mitochondria M2 antigen (also known as pyruvate dehydrogenase) bound to the support.

Anti-hepatitis A antibodies can be detected using purified recombinant human hepatitis A antigens bound to the surface of a glass slide. Diluted patient sera is added, allowing any Hepatitis A antibodies present to bind to the immobilized antigen. Unbound sample is washed away and a FITC (green)-labeled anti-human IgG antibody and a rhodamine (red)-labeled anti-human IgM is added. After washing away any unbound anti-human mAbs, the intensity of the color is measured. The assay can be evaluated as described above. Similar methods are used to detect other hepatitis antibodies.

CMV infection can be detected by detecting CMV immediate-early antigens (pp65) or DNA in peripheral-blood leukocytes can hasten the diagnosis of CMV disease in certain populations, including organ transplant recipients and persons with AIDS. The detection of CMV DNA in cerebrospinal fluid by the polymerase chain reaction is useful in the diagnosis of CMV encephalitis or polyradiculopathy. On the other hand, detection of CMV viremia is a better predictor of acute infection.

Various genetic causes for jaundice are detected using nucleic acid probes, or protein- or polyamide-based probes, which specifically bind to mutant forms of genes or alleles known to be associated with causes for jaundice as listed above. These probes are prepared using standard techniques, and are then spotted onto a support or substrate along with other jaundice symptom-specific probes described herein.

Example 3

Fever/Skin Rash/Weight Loss (Autoimmune) Kit

This kit allows comprehensive, cost-effective, rapid diagnosis of numerous diseases/conditions based on a patient's clinical presentation of autoimmunity (systemic autoimmune diseases have frequently overlapping clinical pictures consisting of fever, skin rash, skin discoloration, and weight loss). Diagnosis of autoimmune diseases is based on the precise detection of autoreactive antibodies, specific gene mutations or other markers (such as autoimmune prone HLAs) using DNA, RNA, live cells, and protein (spotted antigenic proteins and specific mAbs) chips. Briefly, one or more of three groups of etiological conditions are evaluated: A) Systemic and organ-specific autoimmune diseases, B) HLAs that are associated with specific autoimmune diseases, C) Detection of gene mutations that result in the autoimmune syndrome, D) Deficiencies of early and late complement components associated with autoimmune diseases, and E) Therapeutic markers to test potential therapeutic options. See, e.g., Ruddy: Kelley's Textbook of Rheumatology, 6th ed. (W. B. Saunders Company 2001); Allergy: Principles and Practice, 5th ed. Middleton et al. (eds), (Mosby-Year Book, 1998); and Lee: Wintrobe's Clinical Hematology, 10th ed. (Lippincott Williams & Wilkins 1999).

The autoimmune disease kits will include probes that detect at least five or more of the following targets:

A. Antibodies against the following "self" antigens:

Anticardiolipin—purified cardiolipin antigen is used as the probe; ANA (antinuclear antibodies—antigens); SM; RNP; SS-A; SS-B; Scl-70 (DNA-topoisomerase-1); Jo-1 (histidyl-tRNA synthetase); ASCA's mannose (anti-*Saccharomyces cerevisiae* antibodies); Beta2 glycoprotein (apolipoprotein H); Collagen 3 (IV) collagen chain); Cathepsin G; Cationic protein 57 (CAP-57); Elastase; Histones (H2A- H2B- H3- H4); Gliadin; IgA; IgG; IgM; Lactoferrin; LKM-1 (cytochrome P450 2D6); LKM-2 (cytochrome P450 2C9); LKM-3 (uridine diphosphate glucoronosyl transferases) type 2; Mitochondria M2, M5, or M6; Myeloperoxidase (MPO); PART poly-ADP-ribose polymerase; Phosphoproteins (diagnostics of SLA); P0; P1; P2; Ribosome P (carboxyl-terminal 22 amino acid peptide); Serine protease 3 (PR3); ssDNA; dsDNA; Thyroid M (thyroid microsomal antigen); Thyroid T (thyroglobulin); Thyroid peroxidase (TPO); TM; and/or Tissue transglutaminase (tTG).

B. HLA and autoimmune diseases:

In many autoimmune diseases, there is association of particular HLA antigens in populations of individuals with certain diseases. Probes are designed to detect HLAs such as: HLA B27; HLA B38; HLA DR8; HLA DR5; HLA Dw4/DR4; HLA Dw3; 7HLA DR3; HLA DR4; HLA B5; HLA Cw6; HLA A26; HLA B51; HLA B8; HLA Dw3; HLA B35; HLA DR2; HLA B12; and HLA A3

C. Detection of gene mutations that result in the autoimmune syndrome, such as: Fas; FasL; and the Canale-Smith syndrome.

D. Deficiencies of early and late complement components associated with autoimmune diseases. This list includes known mutations resulting in a lack of function of different components of the complement cascade. These mutations are associated with the autoimmune syndrome: C1 (C1q, C1r, C1s); C4; C2; C1 inhibitor; C3; D; Properdin; I; P; C5, C6, C7, C8, and C9.

These kits may also include the following markers:

E. Therapeutic markers to test potential therapeutic options.

For all of these target analytes, corresponding antigens are known and can be isolated, purified, and used as probes.

To use an autoimmune kit, blood will be drawn from the patient and treated as described in Example 2. The following diagram shows how the blood sample is tested:

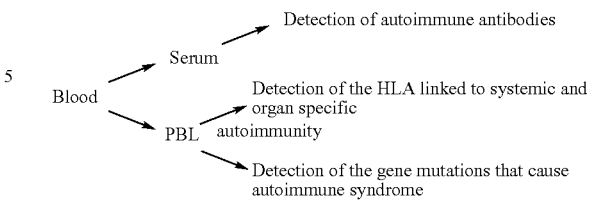

Systemic and organ-specific autoimmune diseases will be assayed using protein, live cells, DNA, or RNA chip technology similar to that described in Example 2 to detect antibodies and antigens in patient sera. Systemic autoimmunity encompasses autoimmune conditions in which autoreactivity is not limited to a single organ or organ system. This definition includes systemic lupus erythematosus (SLE), systemic sclerosis (scleroderma), rheumatoid arthritis (RA), chronic graft-versus-host disease (GVHD), and the various forms of vasculitis. The inference that a disease is autoimmune is made based on the presence of autoantibodies and the localization in diseased tissue of antibody and complement.

Specific antigens and autoantigens (as probes) are spotted onto a support as described in Example 2. Auto-IgG and IgM auto-antibodies against the target analytes are used to visualize the binding or the target analytes to the probes as described herein.

To detect HLA and autoimmune diseases, a protein, live cells, DNA, or RNA chip can be used as described above. All mAbs against different class I and class II HLAs associated with autoimmune diseases are available. Thus, these mAbs against human HLAs are spotted onto a support. These mAbs specifically bind to HLA class I and class II proteins isolated from the surface of nucleated cells (these proteins will be stripped from the cell surface by enzymatic reaction as previously described). The secondary mAbs used for detection will be mAbs anti pan-class I and pan-class II, recognizing all alleles within the class.

Example 4

Recurrent Infection (Immunodeficiency) Kit

This kit allows comprehensive, cost-effective, rapid diagnosis of numerous diseases/conditions based on a patient's clinical presentation of immunodeficiency/recurrent infections. Children with recurrent infections are among the most frequent types of patients seen by primary care physicians. Most patients with recurrent infections do not have an identifiable immunodeficiency disorder. Evaluations of immune function should be initiated for children with clinical manifestations of a specific immune disorder or with unusual, chronic, or recurrent infections such as (1) two or more systemic bacterial infections (e.g., sepsis, osteomyelitis or meningitis), (2) three or more serious respiratory or documented bacterial infections (e.g., cellulitis, draining otitis media, or lymphadenitis within 1 year), (3) infections occurring at unusual sites (e.g., the liver or a brain abscess), (4) infections with unusual pathogens (e.g., *Aspergillus* spp, *Serratia marcescens, Nocardia* spp, or *Pseudomonas cepacia*), and (5) infections with common childhood pathogens but of unusual severity.

The new immunodeficiency kit approach to the diagnosis of immunodeficiency diseases is based on the precise detection of infectious such as anti-viral antibodies and genetic markers such as specific gene mutations, and/or other markers (such as presence of immunoglobulins or complement components). The following etiological conditions are evaluated: A) Detection of viruses causing immunodeficiency, B) detection of immunoglobulin classes, C) Detection of specific immunoglobulins with specificity against common antigens, D) detection of mutations/allelic variations that result in immunodeficiency, E) detection of the gene mutations that result in complement deficiencies, and F) detection of therapeutic markers to test potential therapeutic options. See, e.g., Bone: Pulmonary & Critical Care Medicine (Mosby-Year Book, Inc., 1998); Allergy: Principles and Practice, 5th ed. Middleton et al. (eds.) (Mosby-Year Book, 1998); and Lee: Wintrobe's Clinical Hematology, 10th ed. (Lippincott Williams & Wilkins 1999).

The immunodeficiency kit will include probes that detect at least five of the following targets:

A. Detection of viruses causing immunodeficiency: HIV infection; Epstein-Barr Virus (EBV) infection B. Detection of immunoglobulin classes: IgA; IgG1; IgG2; IgG3; IgG4; and/or IgM.

C. Detection of specific immunoglobulins with specificity against common antigens: Spotted tetanus antigen; Spotted diphtheria antigens; Spotted *Haemophilus influenzae* antigens; and/or Spotted pneumococci's antigens.

D. Detection of mutations/allelic variations that result in immunodeficiency: A) SCID associated with defective cytokine signaling—gammac; Jak3; IL-2; IL-2Ra; and IL-7Ra; B) SCID associated with TCR related defects—CD3g; CD3e; and ZAP70; C) HLA class II deficiency—CIITA; RFX5; and RFXB; D) HLA class I deficiency (bare leukocyte syndrome)—TAP1 and TAP2; E) Immunodeficiency associated with defects in enzymes other than kinases—ADA deficiency and PNP deficiency; F) X-linked hyper-IgM—CD40 ligand; G) X-linked agammaglobulinemia (Bruton)—Btk; H) Non-X-linked agammaglobulinemia—m heavy chain; I) Wiskot-Aldrich Syndrome—WASP; J) Ataxia telangiectasia—ATM; K) DiGeorge anomaly—21q; L) Autoimmune lymphoproliferative syndrome—Fas; M) XLP—SH2D1A/SAP; N) TRAPS—TNFRSF1A; and/or O) Susceptibility to microbacterial infections—IFN-gammaR1; IFN-gammaR2; IL-12p40.

E. Detection of the gene mutations that result in complement deficiencies: C1 (C1q, C1r, C1s); C4; C2; C1 inhibitor; C3; D; Properdin; I; P; C5, C6, C7, and/or C8.

These kits may also include the following markers.

F. Detection of therapeutic markers to test potential therapeutic options

For all of these target analytes, corresponding antigens, antibodies, and/or nucleic acids are known and can be isolated, purified, and used as probes.

To use an recurrent infection kit, blood will be drawn from the patient and treated as described in Example 2. The following diagram shows how the blood sample is tested:

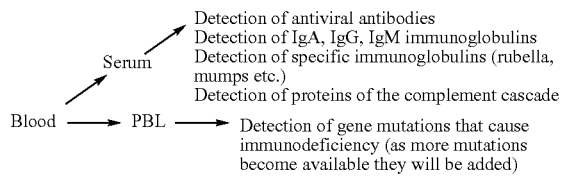

Viruses and genetic mutations causing immunodeficiency are assayed using protein, live cells, DNA, RNA chip technology similar to that described in Example 2 to detect antibodies, antigens, genetic mutations, and allelic variations in patient samples using the techniques described herein.

Example 5

Sore Throat (Pharyngitis) Kit

This kit allows comprehensive, cost-effective, rapid diagnosis based on a patient's clinical presentation of sore throat. This kit tests potential infectious agents including bacteria, viruses and other pathogens. In addition, this kit will test for different therapeutics including such things as bacterial resistance toward some antibiotics. Diagnosis of specific pathogens causing sore throat/pharyngeal pain presentation is based on the precise detection of specific antigens, specific microbial DNA/and or RNA, and specific microbial DNA conferring antimicrobial resistance toward antibiotics. One or more of the following groups of etiological conditions are evaluated: A) Viral diseases resulting in sore throat, B) bacterial and other pathogens resulting in sore throat, and C) therapeutic markers to test potential therapeutic options. See, e.g., Bone: Pulmonary & Critical Care Medicine (Mosby-Year Book, Inc. 1998).

The kits will include probes that detect five or more of the following targets:

A. Viral detection—In most instances, the kits will include family specific reagents (where applicable, types and subtypes will be detected): Rhinovirus; Coronavirus; Adenovirus (types 3, 4, 7, 14); Herpes simplex virus (types 1 and 2); Parainfluenza virus (types 1-4); Influenza virus (types A and B); Coxsackievirus A (types 2, 4-6, 8, 10); Epstein-Barr virus; Cytomegalovirus; and/or HIV-1.

B. Bacterial and other pathogens—In most instances, the kits will include family specific reagents (where applicable, types and subtypes will be detected):

I. Bacterial detection: *Streptococcus pyogenes* (group A beta-hemolytic streptococci); Group C beta-hemolytic streptococci; *Neisseria gonorrhoeae; Corynebacterium diphtheriae; Corynebacterium ulcerans; Arcanobacterium haemolyticum* (*Corynebacterium haemolyticum*); *Yersinia enterocolitica; Treponema pallidum; Chlamydia pneumoniae; Mycoplasma pneumoniae*; and/or *Mycoplasma hominis* (type 1).

II. Detection of antibodies against the beta-hemolytic Lancefield group A *Streptococcus*: Streptozyme; Antideoxyribonuclease-B; and/or Antistreptolysin-O.

These kits may also include the following markers:

C. Therapeutic markers to test potential therapeutic options, such as: Beta-lactamase.

For all of these target analytes, corresponding antigens, antibodies, and/or nucleic acids are known and can be isolated, purified, and used as probes.

To use the new sore throat kits, pharyngeal swab is taken from the patient's tonsils. Also blood can be drawn. Serum will be separated from the nucleated cells. Serum specimens and swab material are used for all protein, DNA, and RNA based procedures performed on protein, DNA, and RNA biochips that include appropriate probes spotted onto supports. Following collection, the serum and nucleic acids are treated as described in Example 2. The following diagram shows how the blood sample is tested:

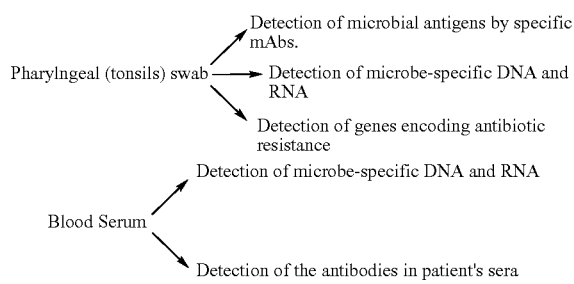

To detect microbial antigens, DNA, RNA, genes, and antibodies, protein, live cells, DNA and RNA biochips as described herein can be used.

Example 6

Cough/Fever/Chest Discomfort/Dyspnea (Pneumonia) Kit

This kit allows comprehensive, cost-effective, rapid diagnosis based on a patient's clinical presentation of lower respiratory tract symptoms. This kit tests both potential infectious (bacteria, viruses and other pathogens) and genetic components that might result in lower respiratory tract symptoms. In addition, this kit will test for different therapeutics including such things as bacterial resistance toward certain antibiotics. Respiratory tract symptoms are among the most common acute problems seen in office practice; the majority are limited to the upper airway. The cough, fever, chest discomfort, and dyspnea that can accompany lower respiratory diseases provoke great concern in the patient. This new kit will contain panels of probes for pathogens known to cause lower respiratory tract symptoms. Briefly, groups causing the following etiological conditions will be evaluated: A) bacterial diseases resulting in Pneumonia/bronchitis, B) viral and other non-bacterial pathogens resulting in Pneumonia/bronchitis, C) autoimmune disease resulting in inflammation of lung tissue, (D) Poisons and Chemicals resulting in inflammation/irritation/destruction of lung tissue, and (E) Therapeutic markers (such as antibiotic resistance genes) to test potential therapeutic options. See, e.g., Bone 1998, and Allergy: Principles and Practice, 5th ed. Middleton et al. (eds) (Mosby-Year Book, 1998).

In particular, pneumonia is an infection of the pulmonary parenchyma. Various bacterial species, mycoplasmas, chlamydiae, rickettsiae, viruses, fungi, and parasites can cause pneumonia. Identification of the etiologic microorganism is of primary importance, since this is the key to appropriate antimicrobial therapy. However, because of the serious nature of the infection, antimicrobial therapy generally needs to be started immediately, often before conventional laboratory confirmation of the causative agent. The new kit can also be used to detect causative agents related to biological warfare or terrorism.

These lower respiratory tract symptom kits will contain probes that detect five or more of the following targets:

A. Bacteria may include (spotted mAbs against these pathogens or DNA or RNA specific probes). In most instances, family specific reagents will be used (where applicable, types and subtypes will be detected): *Streptococcus pneumoniae; Staphylococcus aureus*; Group A streptococci; *Haemophilus influenzae; Klebsiella pneumoniae; Proteus mirabilis; E. Coli; Pseudomonas aeruginosa; Moraxella (Branhamella) catarrhalis; Legionella pneumophila; Porphyromonas gingivalis; Prevotella melaminogenica; Fusobacterium nucleatum; Actinomyces* spp.; Spirochetes; Anaerobic streptococci; Fusobacteria; *Mycoplasma pneumoniae; Mycobacterium tuberculosis; Bacillus anthracis; Yersinia pestis; Francisells tularensis; Coxiella burnetti* (Q fever) and/or *Yersinia enterocolitica*.

B. Viral and other non-bacterial pathogens may include— In most instances, family specific reagents will be used (where applicable, types and subtypes will be detected) Influenza A and B; Adenoviruses; Respiratory Syncytial Virus; Parainfluenza virus; Cytomegalovirus; Varicella (varicella-zoster virus); Variola major (small pox); Rubeola; *Blastomyces* spp.; *Chlamydia psittaci; Coxiella burnetii; Aspergillus; Noccardia; Candida; Pneumocystis Carinii*; Histoplasmosis; and/or Coccidiodomycosis.

C. Detection of Autoimmune diseases resulting in inflammation of lung tissue such as Wegener's Granulomatosis— detection of anti-PR3 antibodies.

D. Detection of Chemicals and Poisons resulting in inflammation/irritation/destruction of lung tissue such as:

I. Poison: such as ricin toxin, and

II. Chemical weapons: such as Distilled Mustard (HD), Lewisite (L), Mustard Gas (H), Nitrogen Mustard (HN-2), Phosgene Oxime (CX), Hydrogen Cyanide, Chlorine (CL), Diphosgene (DP), Nitrogen Oxide (NO), Perfluororisobutylene (PHIB), Phosgene (CG), Red Phosphorous (RP), Sulfur Trioxide-Chlorosulfonic Acid (FS), Teflon and Perfluororisobutylene (PHIB), Titanium Tetrachloride (FM), and/or Zinc Oxide (HC).

These kits may also include the following markers:

E. Therapeutic markers (such as antibiotic resistance genes) to test potential therapeutic options such as: Beta-lactamase For all of these target analytes, corresponding antigens, antibodies, and/or nucleic acids are known and can be isolated, purified, and used as probes.

To use the lower respiratory tract symptom kit, sputum and/or bronchial washings are taken from patients. Also, blood is drawn. Serum will be treated as described in Example 2. Serum specimens and swab material are used for all protein, DNA and RNA based procedures performed on a protein, DNA and RNA chip. Viruses and genetic mutations, as well as bacteria and other agents, causing sore throat, are assayed using protein, DNA, and/or RNA chip technology described herein to detect antibodies, antigens, genetic mutations, and allelic variations in patient samples using the techniques described herein.

Example 7

Joint Pain Kit

This kit allows comprehensive, cost-effective, rapid diagnosis based on a patient's clinical presentation of joint pain symptoms. This kit tests both potential infectious, autoimmune and genetic components that might result in joint pain symptoms. In addition, this kit will test for different therapeutics. The kits will include targets in one or more of the following etiological groups: A) Systemic and organ-specific autoimmune and infectious diseases resulting in joint pain, B) HLAs associated with specific joint diseases/pain, and C) genetic mutation resulting in joint diseases/pain, and D) therapeutic markers to test potential options. See, e.g., Ruddy: Kelley's Textbook of Rheumatology, 6th ed. (W. B. Saunders Company 2001).

In particular, joint pain is often caused by musculoskeletal disorders, which generally classified as inflammatory or noninflammatory. Inflammatory disorders can be infectious (infection with *Neisseria gonorrhoea* or *Mycobacterium tuberculosis*), crystal-induced (gout, pseudogout), immune-related [rheumatoid arthritis (RA), systemic lupus erythematosus (SLE)], reactive (rheumatic fever, Reiter's syndrome), or idiopathic. Noninflammatory disorders can be related to trauma (rotator cuff tear), ineffective repair (osteoarthritis), cellular overgrowth (pigmented villonodular synovitis), or pain amplification (fibromyalgia). Many serologic tests for rheumatoid factor, antinuclear antibodies, complement levels Lyme disease antibodies, antistreptolysin O (ASO) antibodies, or Ig rheumatoid factors are carried out for detection of these diseases.

These kits will include probes designed to detect five or more of the following targets:

A. Systemic and organ-specific autoimmune diseases resulting in joint pain:

1. Detection of antibodies against following "self" antigens: Streptozyme; Antideoxyribonuclease-B; Antistreptolysin-O; human IgA; human IgG; human IgM; Anticardiolipin; ANA (antinuclear antibodies—antigens): SM; RNP; SS-A; SS-B; Scl-70 (DNA—topoisomerase-1); Jo-1 (histidyl—tRNA synthetase); ssDNA; dsDNA; ASCA's mannose (*S. cerevisiae*); LKM-1; LKM-2; LKM-3; and/or Mitochondria M2.

2. Detection of infection with pathogens that could result with joint pain: *Borellia burgdorferi*; *Treponema pallidum*; *Yersinia*; *Campylobacter*; *Salmonella*; *Shigella*; hepatitis A virus; hepatitis B virus; hepatitis C virus; hepatitis D virus; hepatitis E virus; *Haemophilus influenzae*; *Staphylococcus aureus*; gram-negative bacteria (this is a gram-family specific probe); *Streptococccoccus pneumoniae*; *streptococcoccus* (family specific probe); and/or *Neisseria gonorheae*.

B. HLA associated with joint diseases/joint pain: HLA-B27 and/or DRw52.

C. Genetic mutations resulting in joint diseases: HGPT-gene ("Lesch-Nyhan syndrome or Hypoxanthine-Guanine Phosphoribosyltransferase Deficiency); Gene C282Y; and/or Gene H63D.

These kits may also include the following markers:

D. Therapeutic markers to test potential therapeutic options.

For all of these target analytes, corresponding antigens, antibodies, and/or nucleic acids are known and can be isolated, purified, and used as probes.

To use a joint pain kit, blood will be drawn from the patient and treated as described in Example 2. The following diagram shows how the blood sample is tested:

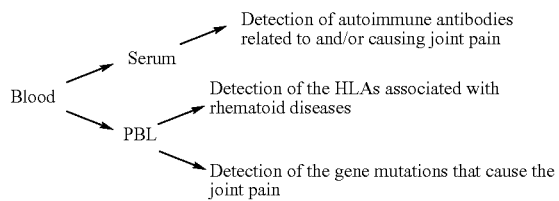

Viruses and genetic mutations, as well as bacteria and other agents causing joint pain, are assayed using protein, live cell, DNA, and/or RNA chip technology described herein to detect antibodies, antigens, genetic mutations, and allelic variations in patient samples using the techniques described herein.

Example 8

Headache/Fever/Meningismus (Meningitis) Kit

This kit allows comprehensive, cost-effective, rapid diagnosis based on a patient's clinical presentation of headache, fever, and meningismus (stiff neck). This kit tests both infectious (viruses, bacteria and other pathogens) and genetic components that might result in the symptom presentation of headache, fever and meningismus. In addition, this kit tests for different therapeutics including such things as antibiotic resistance. The classic clinical presentation of adults with bacterial meningitis includes headache, fever, and meningismus, often with signs of cerebral dysfunction. Nausea, vomiting, rigors, profuse sweating, weakness, myalgias, and photophobia are also common. The kits will include probes for targets in the following etiological groups: A) Infectious markers: Viral, bacterial and other pathogens causing meningitis, B) genetic markers: Diagnosis of the deficiencies in the terminal complement cascade (C5-C9, properidin) C) Therapeutic markers to test potential therapeutics. See, e.g., Goetz: Textbook of Clinical Neurology, 1st ed. (W. B. Saunders Company 1999).

The new headache/fever/meningismus kits will contain probes that detect at least five or more of the following targets:

A. Infectious Markers:

1. Bacteria and Other Pathogens: *Haemophilus influenzae*, *Neisseria meningitidis*, *Streptococcus pneumoniae*, *Listeria monocytogenes*, *Streptococcus agalactiae*, *Propionibacterium acnes*, *Staphylococcus epidermidis*, *Enterococcus faecalis*, *Escherichia coli*, *Klebsiella pneumoniae*, *Pseudomonas aeruginosa*, *Salmonella* spp., *Nocardia* spp., *Mycobacterium tuberculosis*, Spirochetes (such as *Treponema pallidum* (syphilis), *Borrelia Burgdorferi* (Lyme diseases, *Leptospira* spp.), and *Rickettsiae* (such as *Rickettsia rickettsii* (Rocky Mountain spotted fever), *Rickettsia conorii*, *Rickettsia prowazekii* (epidemic or louse-borne typhus), *Rickettsia typhi* (endemic or murine typhus), *Rickettsia tsutsugamushi* (scrub typhus), *Ehrlichia* spp.). 2. Viruses: Non-polio enteroviruses (echovirus 11; echovirus 9; coxsackievirus B5; echoviruses 30, 4, and 6; coxsackieviruses B2, B4, B3, and A9; echoviruses 3, 7, 5, and 21; and coxsackievirus B1, enteroviruses 70 and 71); Mumps virus; Arboviruses (Flaviviridae, The mosquito-borne California enc. Virus, St. Louis enc. Virus, Eastern equine enc. Virus, Western equine enc. Virus, Venezuelan equine encephalitis viruses and Tick-borne Colorado tick fever); Herpesviruses (Primarily herpes simplex virus type 2, but also herpes simplex virus type 1, varicella-zoster virus, cytomegalovirus, Epstein-Barr virus, and human herpesvirus 6); Lymphocytic choriomeningitis virus; Human immunodeficiency virus; Adenovirus; Parainfluenza virus types 2 and 3; Influenza virus; Measles virus; and/or Polio virus.

B: Genetic markers: such as the terminal complement components: C5, C6, C7, C8, C9, and Properidin.

These kits may also include the following markers:

C. Therapeutic markers to test potential therapeutics such as: Beta-lactamase.

For all of these target analytes, corresponding antigens, antibodies, and/or nucleic acids are known and can be isolated, purified, and used as probes.

To use a meningitis kit, cerebrospinal fluid (CSF) and blood will be drawn from the patient. Blood will be treated as described in Example 2, and CSF will be treated using standard techniques. The following diagram shows how the blood sample is tested:

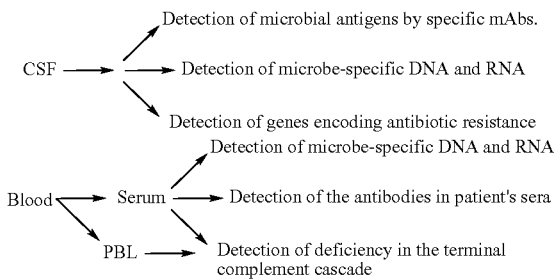

Viruses and genetic mutations, as well as bacteria and other agents, causing headache/meningitis, are assayed using protein, live cell DNA, and/or RNA chip technology described herein to detect antibodies, antigens, genetic mutations, and allelic variations in patient samples using the techniques described herein.

Example 9

Diarrhea Kit

This kit will allow comprehensive, cost-effective, rapid diagnosis based on a patient's clinical presentation of diarrhea. This kit will test infectious agents including bacteria, viruses and other pathogens as well as genetic and autoimmune components that can result in diarrhea. In addition, this kit will test for different therapeutics including such things as bacterial resistance toward some antibiotics. Also, the presence of chemical agents will be evaluated. Probes are selected and used as described herein to detect known targets associated with these symptoms.

The following groups of etiological conditions are evaluated: A) Bacteria resulting in diarrhea, B) viruses and other pathogens resulting in diarrhea, C) genetic factors involved in diarrhea, D) autoimmune diseases resulting in diarrhea, E) chemical agents resulting in diarrhea, F) Therapeutic markers to test potential therapeutic options.

These diarrhea kits will contain probes that detect five or more of the following targets:

A. Bacteria resulting in diarrhea: *Bacillus cereus, Staphylococcus aureus, Clostridium perfingens, Vibrio cholerae,* enterotoxigenic *Escheria coli, Klebsiella pneumoniae, Aeromonas* species, Enteropathogenic and enteroadherent *E. coli* (O157:H7), *Giardia* organisms, *Clostridium difficile*, Hemorrhagic *E. coli, Salmonella, Campylobacter, Aeromonas* species, *Vibrio parahaemolyticus, Yersinia, Shigella* species, enteroinvasive *E. coli, Bacillus anthracis, Clostridium botulinum*

B. Viruses and other pathogens resulting in diarrhea: Cytomegalovirus, Herpes simplex, Enteropathogenic Adenovirus, Rotovirus (Group A, B, C), Calicivirus, Astrovirus, *Cryptosporidium, Septata intestinalis, Microsporidium, Entercytozoon bienusi, Isospora belli, Cyclospora* species, *Giardia lamblia, Entamoeba histolytica, Leishmania donovani, Blastocystic hominis, Pneumocystis carini, Histoplasma, Coccidioides, Candida albicans, Cryptococcus*

C. Genetic diseases involved in diarrhea: Acute Hepatic Porphyria; Delta-Aminolevulinate Dehydratase Deficiency; Porphobilinogen Synthase Deficiency, Amyloidosis Type I; Amyloid Polyneuropathy, Andrade or Portugese Type; Amyloidosis, Portugese Type; Amyloidosis, Swedish Type, Beckwith-Wiedemann Syndrome, Cystic Fibrosis; CF, Dubin-Johnson Syndrome; Hyperbilirubinemia Type II, Epidermolysis Bullosa Letalis with Pyloric Atresia; Aplasia Cutis Congenita with Gastrointestinal Atresia; Carmi Syndrome, Erythropoietic Protoporphyria; Erythrohepatic Protoporphyria; Ferrochelatase Deficiency; Heme Synthetase Deficiency Ethylmalonic Encephalopathy, Familial Adenomatous Polyposis; APC; Adenomatous Polyposis Coli; FAP; Gardner syndrome, Familial Dysautonomia; Riley-Day Syndrome, Familial Gastric Cancer, Familial Hibernia Fever; Familial Periodic Fever; TRAPS, Familial Mediterranean Fever; Recurrent Polyserositis, Hereditary Coproporphyria; Coproporphyrinogen Oxidase Deficiency; Harderoporphyria (Included), Hereditary Non-Polyposis Colon Cancer; HNPCC; Lynch syndrome, Hermansky-Pudlak Syndrome; HPS, Multiple Endocrine Neoplasia Typ; MEN1, Ornithine Transcarbamylase Deficiency; OTC Deficiency, Pearson Syndrome; Sideroblastic Anemia w/Marrow Cell Vacuolization & Exocrine Pancreatic Dysfxn, Peutz-Jeghers Syndrome; Hamartomatous Intestinal Polyposis; PJS, Phosphoglycerate Kinase Deficiency; PGK Deficiency, Pseudoxanthoma Elasticum, Dominant; PXE, Dominant Pseudoxanthoma Elasticum, Recessive; PXE, Recessive Pyruvate Kinase Deficiency, Townes-Brocks Syndrome; TBS, Wolman Disease; Cholesterol Ester Storage Disease von Hippel-Lindau Syndrome; VHL D. Autoimmune diseases resulting in diarrhea: Antibodies against the following "self" antigens that are associated with autoimmune diseases causing diarrhea, such as ASCA's mannose (anti-*Saccharomyces cerevisiae* antibodies);

These kits may also include the following markers:

E: Chemical agents resulting in diarrhea such as: Adamsite (DM), Diphenylchloroarsine (DA), Diphenylcyanoarsine (DC)

F. Therapeutic markers to test potential therapeutic options such as: Beta-lactamase.

Example 10

Vaginal Discharge and/or Bleeding/Abdominal/Pain/ Nausea/Vomiting/Temperature (Vaginitis/PID) Kit This kit will allow comprehensive, cost-effective, rapid diagnosis based on a patient's clinical presentation of vaginitis/pelvic pain. This kit will test potential infectious agents including bacteria, viruses and other pathogens. In addition, this kit will test for different therapeutics including such things as bacterial resistance toward some antibiotics. Diagnosis of specific pathogens causing sore throat/pharyngeal pain presentation is based on the precise detection of specific antigens, specific microbial DNA/and or RNA, and specific microbial DNA conferring antimicrobial resistance toward antibiotics. One or more of the following groups of etiological conditions are evaluated: A) Viral diseases resulting in vaginitis/pelvic pain, B) bacterial and other pathogens resulting in vaginitis/pelvic pain, C) therapeutic markers to test potential therapeutic options.

The kits will include probes that detect five or more of the following targets:

A) Viral detection—In most instances, the kits will include family specific reagents (where applicable, types and subtypes will be detected): Human papilloma virus (HPV); Molluscum contagiosum; Herpes simplex virus (HSV) type 1 and 2; Human immunodeficiency virus (HIV); Hairy leukoplakia (Epstein-Barr virus)

B). Bacterial and other pathogens—In most instances, the kits will include family specific reagents (where applicable, types and subtypes will be detected): *Treponema pallidum; Chlamydia trachomatis; N. gonorrhoeae; Escherichia coli; Bacteroides* species; anaerobic cocci; *Calymmatobacterium granulomatis; H. ducreyi; Mycoplasma hominis; Ureaplasma urealyticum; C. trachomatis; Candida albicans*

These kits may also include the following markers:

C). Therapeutic markers to test potential therapeutic options such as: Beta-lactamase.

Example 11

Skin Discoloration/Pain/Ulcer (Skin) Kit

This kit will allow comprehensive, cost-effective, rapid diagnosis based on a patient's clinical presentation of skin rash. This kit will test infectious agents including bacteria, viruses and other pathogens as well as genetic and autoimmune components that can result in skin rash. In addition, this kit will test for different therapeutics including such things as bacterial resistance toward some antibiotics. Also, the presence of chemical agents will be evaluated. Probes are selected and used as described herein to detect known targets associated with these symptoms.

The following groups of etiological conditions are evaluated: A) Bacteria resulting in skin rash, B) viruses and other pathogens resulting in skin rash, C) genetic factors involved in skin rash, D) autoimmune diseases resulting in skin rash, E) chemical agents resulting in skin rash, F) Therapeutic markers to test potential therapeutic options.

A. Bacteria resulting in skin rash: In most instances, the kits will include family specific reagents (where applicable, types and subtypes will be detected): *Staphylococcus aureus*; Group A streptococci; Anthrax, *Treponema pallidum, Chlamydia trachomatis, N. gonorrhoeae, Escherichia coli, Bacteroides* species, Anaerobic cocci, *Calymmatobacterium granulomatis, H. ducreyi., C. trachomatis, Candida albicans, Yersinia pestis*, Tinea, Candidiasis (moniliasis), Tinea versicolor, Pityrosporum folliculitis.

B. Viruses and other pathogens resulting in skin rash: In most instances, the kits will include family specific reagents (where applicable, types and subtypes will be detected):

Human papilloma virus (HPV), Molluscum contagiosum, Herpes simplex virus (HSV) type 1 and 2, Hairy leukoplakia (Epstein-Barr virus), variola major (smallpox), arenaviruses, filoviruses, bunyaviruses, and flaviviruses C. Genetic diseases involved in skin rash: Hermansky-Pudlak Syndrome*;

Lactate Dehydrogenase Deficiency*; LDH Deficiency

Pseudoxanthoma Elasticum, Recessive*; PXE, Recessive

Peutz-Jeghers Syndrome*; Hamartomatous Intestinal Polyposis; PJS

Pachyonychia Congenita*; Jackson-Lawler Syndrome; Jadassohn-Lewandowsky

Oculocutaneous Albinism Type I (Tyrosinase Related)*; OCA1; Oculocutaneous

Pseudoxanthoma Elasticum, Dominant*; PXE, Dominant

Neurofibromatosis Type I*; NF1; Von Recklinghausen Disease

Neurofibromatosis Type II*; NF2

D. Autoimmune diseases resulting in skin rash:

Antibodies against the following "self" antigens such as: Anticardiolipin—purified cardiolipin antigen is used as the probe; ANA (antinuclear antibodies—antigens); SM; RNP; SS-A; SS-B; Scl-70 (DNA-topoisomerase-1); Jo-1 (histidyl-tRNA synthetase); Beta2 glycoprotein (apolipoprotein H); Collagen 3 (IV) collagen chain) Elastase; Histones (H2A-H2B- H3- H4); Gliadin; IgA; IgG; IgM; Lactoferrin; PART poly-ADP-ribose polymerase; Phosphoproteins (diagnostics of SLA); P0; P1; P2; Ribosome P (carboxyl-terminal 22 amino acid peptide);

These kits may also include the following markers:

E: Chemical agents resulting in skin rash such as: Distilled Mustard (HD), Lewisite (L), Mustard Gas (H), Nitrogen Mustard (HN-2), Phosgene Oxime (CX), Phenodichloroarsine (PD), Sesqui Mustard F. Therapeutic markers to test potential therapeutic options such as: Beta-lactamase.

Example 12

Immunization/Immunocompetence Kits

Immunization represents a remarkably successful and very cost-effective means of preventing infectious diseases. Because of routine childhood immunizations, the occurrence of once common contagious diseases declined markedly in the United States and other countries in the second half of the 20th century. Public health programs based on vaccination have led to global eradication of smallpox, elimination of poliomyelitis from the Americas and possibly from the world in the near future, and greater than 95% reduction in the United States and other countries of invasive *Haemophilus influenzae* type b (Hib) disease. In the United States, immunization has almost eliminated congenital rubella syndrome, tetanus, and diphtheria and has reduced the incidence of rubella and measles to record low rates.

Infants and children in this country routinely receive vaccines against 10 diseases: diphtheria, tetanus, pertussis, poliomyelitis, measles, mumps, rubella, Hib infection, hepatitis B, and varicella. Rotavirus vaccine is also recommended, with the realization that universal immunization may require additional time and resources. Hepatitis A vaccine is recommended for some groups of children. More than 50 immunobiologic products are licensed in the United States. Despite this remarkable success, many people are not adequately immunized. Reasons for this result include, inter alia, (1) lack of appropriate immunization in childhood, (2) low quality of administered vaccines, and (3) immunoincompetence of the host at the time of vaccination.

The new devices and methods can be used to evaluate both the immunocompetence status of patients, and the immune response towards various pathogens. In addition, other parameters of the immune system can be evaluated. Kits for such analyses will contain probes for one or more of: a) antibodies against viral and bacterial pathogens that are administered with vaccine; b) viral and bacterial antigens that are administrated as vaccine; and c) probes for genes related with recurrent infection (see Recurrent infection kit). The probes are selected and used as described herein to detect known targets associated with these symptoms.

Example 13

Blood Assaying Kits (BloodBank/Transfusion) Kits

Clinically intelligent bloodbank screening diagnostic kits are manufactured using the new methods described herein. These kits allow comprehensive, cost-effective, rapid diagnosis/screening of numerous diseases/genetics characterization that preclude blood transfusion/organ donation.

The list of pathogens/genetic markers that need to be tested is strictly regulated/required by the Food and Drug Administration (FDA). The new kits include all tests required and/or recommended by the FDA and by the American Association of Blood Banks. In addition, due to their cost-effectiveness, the kits can include other assays recommended or under investigation for pathogens and genetic markers. Current requirements by the FDA are that each unit of blood must be tested after blood is drawn. The tests include assays for: ABO group (blood type), Rh type (positive or negative), and any unexpected red blood cell antibodies that can cause problems in the recipient. Screening tests are also performed for evidence of donor infection with hepatitis viruses B and C, human immunodeficiency viruses (HIV) 1 and 2, human T-lymphotrophic viruses (HTLV) I and II and syphilis. BloodBank kit will contain panels of all scientifically accepted screening tests for diagnosis of different infectious diseases (HIV, Syphilis, HBV, HCV, CMV), genetic characteristics (HLA, Rh antigens) that could prevent and/or influence blood transfusion/organ transplantation. Kits for these blood analyses contain probes that detect one or more of the following targets: (1) viral and bacterial pathogens that excludes blood/organ transplantation, (2) Characterization of HLAs, blood groups and Rh (and other related) blood groups. All blood tested positive is discarded.

The kits include probes designed to detect five or more of the following targets that are analyzed using either UniScreen, ProScreen, and/or NuScreen chips:

I. Viruses: hepatitis A virus; hepatitis B virus; hepatitis C virus; HIV 1 and 2; Human T-Lymphotrophic Virus, Types I and II (Anti-HTLV-I, -II); *Treponema pallidum; Borrelia burgdorferi*; CMV; Malaria; Epstein-Barr virus (EBV); Babesiosis; and/or Chagas' Disease;

II. Blood groups, Rh types or HLA in donor sera: HLA Typing; ABO Blood Group System; Rh System (Rh d, Rh e, and Rh c); Other blood groups (Kell (K), Duffy (Fy), Kidd OK), MN, P, Lewis (Le), Lutheran (Lu), Vel system, and/or Wright (Wra).

For all of these target analytes, corresponding antigens, antibodies, and/or nucleic acids are known and can be isolated, purified, and used as probes.

To use the new blood screening kits, donated blood will be collected. Serum will be separated from the nucleated cells. Serum specimens will be used for all protein-based procedures performed on a protein chip. Following collection, the serum should be separated from the clot and treated as described in Example 2.

The following diagram shows how the blood sample is tested:

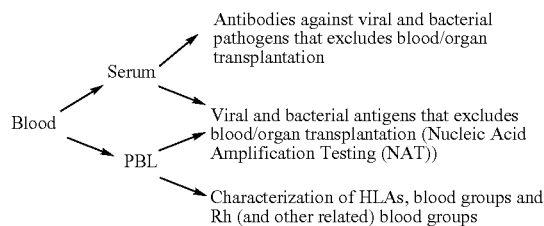

Viral and bacterial pathogens that exclude blood donation/organ transplantation, as well as HLAs, Rh, and other blood groups, are assayed using protein, DNA, and/or RNA chip technology described herein to detect antibodies, antigens, etc. in patient samples using the techniques described herein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

For example, kits for other specific symptom presentations include: Malaise/headache/myalgia/backache (Encephalitis) Kit, Conjunctival hyperemia/lid edema/watery and/or mucopurulent discharge/preauricular lymphadenopathy (Conjunctivitis) Kit, Elevated temperature/tachycardia/increased respirations/leukocytosis/an impaired peripheral leukocyte response/oliguria (Septicemia) Kit, Septicemia after BMT/immunosuppression Kit, Fever/chills/localized bone pain and tenderness/leukocytosis/bone deformation (Osteomyelitis) Kit, Tenderness of the urethra or the suprapubic area/temperature/shaking chills, nausea (Cystitis/pyelonephritis/urethritis) Kit, Tenderness of the pubic area, frequency, urgency, and dysuria in man (Prostatitis/epididimitis) Kit, Infertility, Ambigous Genitalia Kit, Hearing Loss (Hearing) Kit, Loss of sight (Blindness) Kit, Mental Retardation Kit, Muscular weakness/pain/numbness (Neuromuscular) Kit, Muscular weakness/pain/numbness/mental retardation/tremor/(Neurological) Kit, Bone Deformation/pain (Bone) Kit, Cardiac dyspnea (Heart failure) Kit, Uremia (Kidney Failure) Kit, Malabsorption/weight loss (Gastro) Kit, Sinus pain/fever (Sinusitis) Kit, and Tropical Diseases Kit.

What is claimed is:

1. A multiplexed test comprising two or more clusters of a probe or set of probes, wherein at least one probe detects in a biological sample from a subject at least one target that is indicative of a cause of at least one medical symptom, and wherein at least one probe detects a second target in the biological sample, wherein the second target is a genetic target comprising at least one sequence in the subject that makes the subject resistant, tolerant intolerant or susceptible to a therapeutic agent useful for treating the cause of the at least one medical symptom.

2. The multiplex test of claim 1, wherein the cause is selected from the group consisting of a pathogen, an infection, inflammation, autoimmunity, a neoplasm, and a drug.

3. The multiplex test of claim 1, wherein the cause is selected from the group consisting of iatrogenic, congenital, developmental inherited, environmental endocrine, metabolic and a combination thereof.

4. The multiplex test of claim 1, wherein the first target is selected from the group consisting of an antibody, an antigen, an enzyme, a cell, an endogenous genetic marker, a peptide, a polypeptide, a protein, a hapten, a glycoprotein, an aptamer, a small organic molecule, an inorganic molecule, a toxin, and a polysaccharide, or a combination thereof.

5. The multiplex test of claim 1, wherein the subject is an animal selected from the group consisting of a human, a bird, a dog, a cat, a cow, a pig, and a horse.

6. The multiplex test of claim 1, wherein the two or more clusters of a probe or set of probes is attached to a surface selected from the group consisting of: a microfluidic device, a sequencing chip, a biochip, a microarray, a bead and a membrane comprising a material selected from the group consisting of nitrocellulose, nylon, polyethylene, polycarbonate, glass microfiber and gortex.

7. The multiplex test of claim 1, wherein the two or more clusters of a probe or set probes are contained in an array that is deposited on a multiplexed device.

8. A kit comprising
(a) two or more clusters of a probe or set of probes, wherein at least one probe detects in a biological sample from a subject at least one target that is indicative of a cause of at least one medical symptom, and wherein at least one probe for a second target detects in the biological sample at least one genetic sequence in a subject that makes the subject resistant, tolerant, intolerant or susceptible to a therapeutic agent useful for treating the cause of the at least one medical symptom; and
(b) reagents and/or materials necessary for testing the sample.

9. The kit according to claim 8, wherein at least one of the clusters of a probe or set of probes detects at least one target associated with jaundice and/or liver failure.

10. The kit according to claim 9, wherein at least one of the clusters of a probe or set of probes detects at least five targets selected from the group consisting of anti-LKM-1 antibodies, anti-mitochondrial M2 antibodies, Hepatitis A virus, Hepatitis B virus, Hepatitis C virus, Hepatitis D virus, Hepatitis E virus, and CMV virus.

11. The kit according to claim 8, wherein at least one of the clusters of a probe or set of probes detects at least one of a mutation and/or allelic variant of the subject selected from the group consisting of Dubin-Johnson Syndrome, Hyperbilirubinemia Type I, Acute Hepatic Porphyria, Delta-Aminolevulinate Dehydratase Deficiency, Porphobilinogen Synthase Deficiency Alagille Syndrome, Arteriohepatic Dysplasia, Cholestasis with Peripheral Pulmonary Stenosis, Alpha-1-Antitrypsin Deficiency, Carbamoylphosphate Synthetase I Deficiency, Carbamyl Phosphatase Deficiency, Carbamyl Phosphate Synthetase Deficiency, Carnitine-Acylcarnitine Translocase Deficiency, Citrullinemia, Ferrochelatase Deficiency, Heme Synthetase Deficiency, fatty Acid Oxidation Disorder, Unspecified, Fructose 1,6 Bisphosphatase Deficiency, Galactosemia, Galactose Epimerase Deficiency, Galactose-1-Phosphate Uridyltransferase Deficiency, NGlutaricacidemia Type II, Glutaricaciduria Type II, Glycogen Storage Disease Type I/Ia, Glucose-6-Phosphatase Deficiency, Von Gierke Disease, Glycogen Storage Disease Type III, Cori Disease, Debrancher Deficiency, Forbe Disease, Glycogen Storage Disease Type IV, Brancher Deficiency, Glycogen Storage Disease Type IX, Glycogen Storage Disease Type VIII, Phosphorylase Kinase Deficiency of Liver, Glycogen Storage Disease Type Ib, Glucose-6-Phosphate Translocase Defect, Glycogen Storage Disease Type VI, HERS Disease, Hereditary Coproporphyria, Coproporphyrinogen Oxidase Deficiency, Harderoporphyria, Hereditary Fructose Intolerance, Fructosemia, Hereditary Hemochromatosis, Long Chain 3-hydroxyacyl-CoA Dehydrogenase Deficiency, Acute Fatty Liver, Disease of Pregnancy, HELLP, Hemolysis, Enzymes, and Low Platelets, LCHAD Deficiency, Trifunctional Protein Deficiency, Long Chain Acyl-CoA Dehydrogenase Deficiency, LCAD Deficiency, Medium Chain 3-Ketothiolase Deficiency, MCKAT Deficiency, Medium Chain Acyl-Coenzyme A Dehydrogenase Deficiency, MCAD Deficiency, Mucopolysaccharidosis Type II, Hunter Syndrome, MPS II, Mucopolysaccharidosis Type IIIB, MPS IIIB, Sanfilippo Syndrome Type B, Mucopolysaccharidosis Type IIIC, MPS IIIC, Sanfilippo Syndrome Type C, Mucopolysaccharidosis Type IVB, MPS IVB, Morquio Syndrome Type B, Mucopolysaccharidosis Type VI, Arylsulfatase B Deficiency, MPS VI, Maroteaux, Lamy Syndrome, Mucopolysaccharidosis Type VII, Glucuronidase Deficiency MPS, MPS VII, Sly Syndrome, Niemann-Pick Disease Without Sphingomyelinase Deficiency, Niemann-Pick Disease Type C, Niemann-Pick Disease Type D, Niemann-Pick Disease, Nova Scotian Type, Ornithine Transcarbamylase Deficiency, OTC Deficiency, Phosphorylase Kinase Deficiency of Liver and Muscle, Polycystic Kidney Disease, Recessive, ARPKD, PKD, Infantile, PKD, Recessive, Salla Disease, Sialic Acid Storage Disease, Sialidosis, Glycoprotein Neuraminidase Deficiency, ML I, ML1, Mucolipidosis, Wilson Disease, Wolman Disease, Cholesterol Ester Storage Disease, and/or Zellweger syndrome, and Cerebrohepatorenal Syndrome.

12. The kit according to claim 8, wherein at least one of the clusters of a probe or set of probes detects at least one target associated with pharyngitis.

13. The kit according to claim 12, wherein at least one of the clusters of a probe or set of probes detects at least five targets selected from the group consisting of a virus, a bacteria, a mycoplasma, and an antibody to a pathogen.

14. The kit according to claim 13, wherein the virus is selected from the group consisting of Rhinovirus, Coronavirus, Adenovirus types 3, 4, 7, and 14, Herpes simplex virus types 1 and 2, Parainfluenza virus types 1-4, Influenza virus types A and B, Coxsackievirus A types 2, 4-6, 8, and 10, Epstein-Bar virus, Cytomegalovirus, and HIV-1.

15. The kit according to claim 13, wherein the bacteria is selected from the group consisting of *Streptococcus pyogenes* (group A beta-hemolytic streptococci), Group C beta-hemolytic streptococci *Neisseria gonorrhoeae, Corynebacterium diphtheriae, Corynebacterium ulcerans, Arcanobacterium haemolyticum* (*Corynebacterium haemolyticum*), *Yersinia enterocolitica, Treponema pallidum*, and *Chlamydia pneumoniae.*

16. The kit according to claim 13, wherein the mycoplasma is selected from the group consisting of *Mycoplasma pneumoniae* and *Mycoplasma hominis* (type 1).

17. The kit according to claim 8, wherein at least one of the clusters of a probe or set of probes detects at least one target associated with lower respiratory tract symptoms.

18. The kit according to claim 17, wherein the lower respiratory tract symptoms are selected from the group consisting of cough, fever, chest discomfort, dyspnea, pneumonia, and a combination thereof.

19. The kit according to claim 8, wherein at least one of the clusters of a probe or set of probes detects causative agents related to biological warfare or terrorism.

20. The kit according to claim 8, wherein at least one of the clusters of a probe or set of probes detects at least one target associated with headache, fever, meningismus, nausea, vomiting, rigors, profuse sweating, weakness, myalgias, and photophobia.

21. The kit according to claim 20, wherein the second target is a genetic marker selected from the group consisting of C5, C6, C7, C8, C9, and Properidin.

22. The kit according to claim 20, wherein the at least one target is a therapeutic marker selected from the group consisting of beta-lactamase and cytochrome P450.

23. The kit according to claim 8, wherein at least one of the clusters of a probe or set of probes detects at least one target associated with diarrhea.

24. The kit according to claim 8, wherein at least one of the clusters of a probe or set of probes detects at least one target associated with septicemia.

* * * * *